US008431346B2

(12) United States Patent
Beever et al.

(10) Patent No.: US 8,431,346 B2
(45) Date of Patent: Apr. 30, 2013

(54) SCREENING FOR ARTHROGRYPOSIS MULTIPLEX IN BOVINES

(75) Inventors: Jonathan Edward Beever, Mansfield, IL (US); Brandy Michele Marron, Fithian, IL (US)

(73) Assignee: Agrigenomics, Inc., Mansfield, IL (US)

( * ) Notice: Subject to any disclaimer, the term of this patent is extended or adjusted under 35 U.S.C. 154(b) by 521 days.

(21) Appl. No.: 12/642,028

(22) Filed: Dec. 18, 2009

(65) Prior Publication Data

US 2011/0151440 A1 Jun. 23, 2011

(51) Int. Cl.
*C12Q 1/68* (2006.01)
*C12P 19/34* (2006.01)

(52) U.S. Cl.
USPC .......... 435/6.11; 435/6.12; 435/6.1; 435/91.2

(58) Field of Classification Search ........................ None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,683,292 | A | 7/1987 | Hahn |
| 5,498,521 | A | 3/1996 | Dryja et al. |
| 6,013,444 | A | 1/2000 | Dau et al. |
| 6,225,093 | B1 | 5/2001 | Grant et al. |
| 6,306,591 | B1 | 10/2001 | Cockett et al. |
| 6,759,192 | B1 | 7/2004 | Blumenfeld et al. |
| 8,158,356 | B2 | 4/2012 | Beever et al. |
| 2003/0203372 | A1 | 10/2003 | Ward et al. |
| 2005/0260603 | A1 | 11/2005 | Denise et al. |
| 2006/0063191 | A1 | 3/2006 | Sutherland et al. |
| 2009/0239212 | A1 | 9/2009 | Beever et al. |

FOREIGN PATENT DOCUMENTS

| | | |
|---|---|---|
| GB | 0030076 | 1/2001 |
| WO | WO 93/16094 | 8/1993 |
| WO | WO 02/46465 | 6/2002 |

OTHER PUBLICATIONS

GenBank record accession AC220399 (GI: 171186954) Mar. 28, 2009. Obtained form www.ncbi.nlm.gov on Jun. 20, 2012, 44 pages.*
Pfizer release. Dec. 29, 2008, "Pfizer Animal Genetics Now Running Curly Calf Test." obtained from http://beefmagazine.com/genetics/selection-tools/1229-curly-calf-test[May 14, 2012 9:05:03 PM]; three pages.*
Kreidler, Mick. Jan. 1, 2009, Farm Journal. "How to handle a genetic disorder: a popular bloodline of Angus and Angus-influenced cattle is a carrier of a genetic defect" obtained from http://www.highbeam.com/doc/1G1-249607189.html[May 14, 2012 8:44:57 PM], three pages.*
American Angus Association (Nov. 25, 2008) "Arthrogryposis Multiplex—Questions and Answers," http://www.angus.org/aaa _am _faq1.pdf.
Beever (Nov. 10, 2008) "An Update on Arthrogryposis Multiplex in Cattle," httP://www.anguscommunicationstoday.com/page/industry/news.html?inet=aD12YXFoZmdlbC1hcmpmLXlheCZyaD12YXFoZmdlbC1hcm-pmLXlheCZwbHVnaW4tYWN0aW9uPXJlYWQmcnBsdWdpbi-1hY3Rpb249ZGVmYXVsdCZjcGx1Z2luPXF2cWxiaHhhYmom-cmVjaWQ9MTgwMw.
Harvey et al. (Jul. 2007) "Disruption of Glomerular Basement Membrane Charge Through Podocyte-Specific Mutation of Agrin Does not Alter Glomular Permselectivity," *Am. J. Pathol.* 171(1):139-152.
Important Update on the Status of Curly Claf Syndrome (Sep. 2008) http://www.angus.org/pub/AM/aaa_notice.pdf.
International Search Report and Written Opinion, Corresponding to International Application No. PCT/US09/68751, Mailed Jul. 1, 2010.
King, J.P. (Jun. 12, 2009) An Important Message from American Angus Association Presedent Jay King, http://www.anpus.org/Pub/GeneticPolicyLetter.html.
Laughlin, D. (Sep. 5, 2008) "Request for assistance: Reporting Abnormal Calves," American Angus Association, http://www.angus.org/aaa_request.pdf.
Liu et al. (Mar. 28, 2008) "Bos Taurus clone CH240-360A16, Working Draft Sequence, 11 unordered pieces," GenBank Accession No. AC220399.
Vallery, C. (Sep. 25, 2008) "Angus Breed Tackling Curly Calf Syndrome," *Cattle Business Weekly* http://www.cattlebusinessweekly.com/main.asp?SectionID=1&SubSectionID=1&ArticleID=837.

* cited by examiner

*Primary Examiner* — Juliet Switzer
(74) *Attorney, Agent, or Firm* — Lathrop & Gage LLP

(57) ABSTRACT

Provided are methods, materials and kits for analyzing DNA samples from bovine to determine whether the animal is a recessive carrier of a genetic mutation that is associated with arthrogryposis multiplex (AM). DNA-containing samples are analyzed by genetic testing to determine whether or not a deletion mutation is present in one of the alleles that are responsible for the AM genetic mutation. In an aspect the deletion encompasses the entirety of the ISG15 ubiquitin-like modifier (ISG15) gene. In an aspect the deletion further encompasses one or both of the 5' regulatory region of the hairy and enhancer split 4 (HES4) and of the agrin (AGRN) gene and of the first two exons of the AGRN gene.

19 Claims, 1 Drawing Sheet

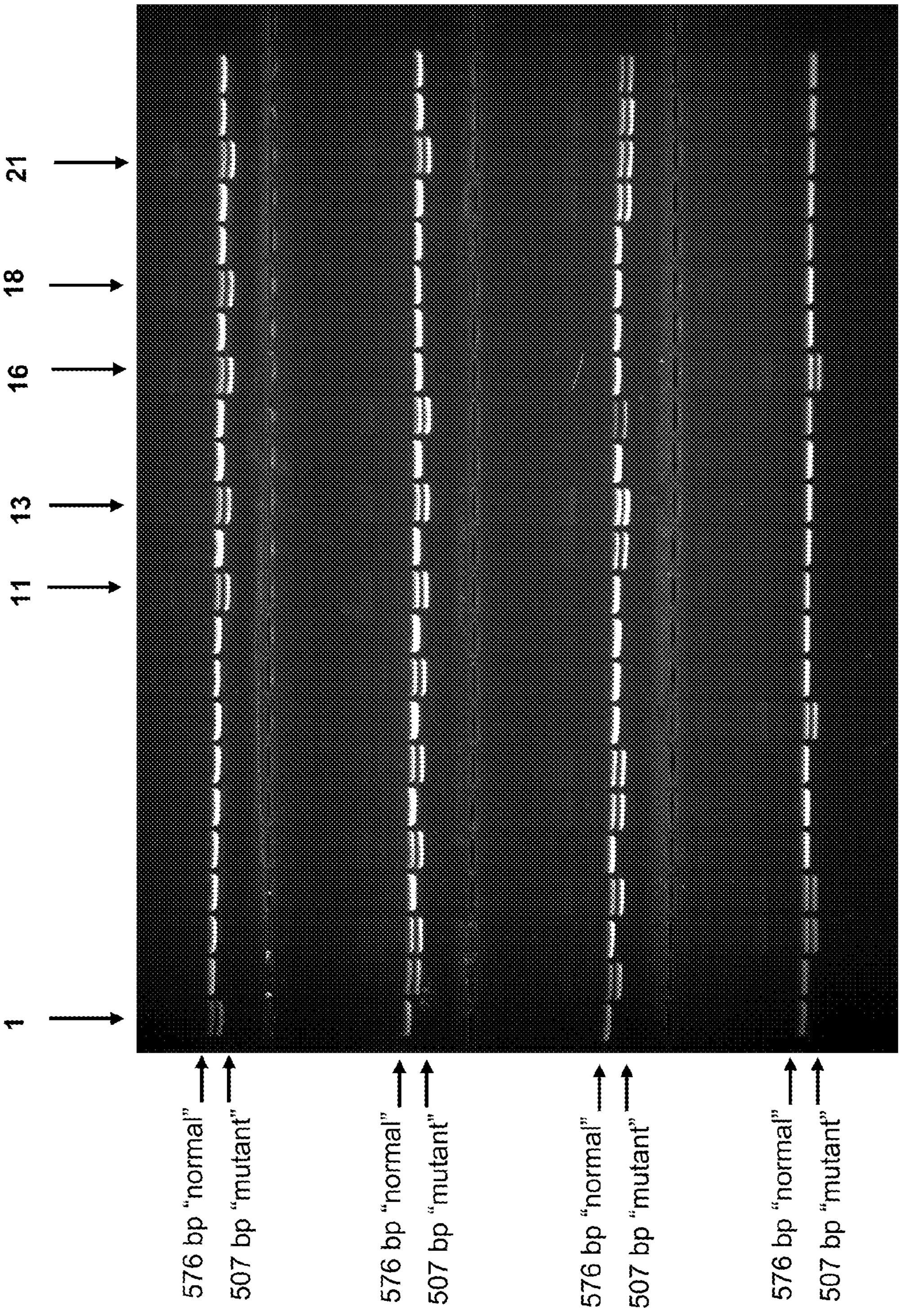
21
18
16
13
11
1
576 bp “normal”
507 bp “mutant”
576 bp “normal”
507 bp “mutant”
576 bp “normal”
507 bp “mutant”
576 bp “normal”
507 bp “mutant”

SCREENING FOR ARTHROGRYPOSIS MULTIPLEX IN BOVINES

STATEMENT REGARDING FEDERALLY SPONSORED RESEARCH OR DEVELOPMENT

This invention was at least in part made with government support under AG 2004-34480-14417 and 58-5438-2-313 awarded by the USDA. The government has certain rights in the invention.

REFERENCE TO A SEQUENCE LISTING

A sequence listing containing SEQ ID NOs:1-19 is submitted herewith and is specifically incorporated by reference.

BACKGROUND OF THE INVENTION

Arthrogryposis Multiplex (AM), commonly referred to as "Curly Calf Syndrome," is a genetic defect that has recently been reported in Angus cattle. Based on pedigree examination of affected calves, this genetic defect is determined to have an autosomal recessive mode of inheritance. Due to this recessive inheritance pattern, only calves that are homozygous (i.e., receiving a chromosome with the mutation from both parents) for the mutation causing AM are affected with multiple abnormalities most often including arthrogryposis (contracted or extended limbs with stiffened joints), scoliosis and kyphosis (abnormal curvature of the spine), and muscular hypoplasia (reduced muscle development). Less commonly, the syndrome is associated with mild hydrocephalus caused by inflammation of the brain. Calves are born dead or fail to thrive and die shortly after birth. Classification of normal appearing individuals (e.g., those that are homozygous for the normal allele or heterozygous or carriers of the mutation) is virtually impossible in the absence of planned breeding studies or test matings. Accordingly, there is a need for a test that can reliably identify whether an animal is a heterozygous or a carrier of the mutation.

The American Angus Association® cattle breeders group recently became aware of a small number of calves born dead with bent and twisted spines. Subsequent monitoring of the situation provided further incidents of such calves being born. Reproductive technologies, where certain parents having beneficial traits are used frequently, can result in the observation of unwanted defects introduced in a breeding program. Good tracking of lineage, however, can provide the ability to breed out certain undesirable genes. In this case, extensive breeding and pedigree studies have revealed that AM has an autosomal recessive mode of inheritance. For the AM to be expressed, a calf must have inherited the defective gene from both parents. A calf that expresses the phenotype is "homozygous" for the mutant AM gene, and the parents of such a calf are "heterozygous carriers" for the mutant AM gene (homozygous animals do not survive to reproduce). It is virtually impossible in the absence of planned breeding studies or test matings to classify whether a normal appearing individual is a heterozygous carrier of the mutant AM gene (AM carrier or "AMC") or is homozygous for the normal allele (AM free or "AMF"). Genetic screening is beneficial in avoiding loss of genetic resources due to culling based only on pedigree.

Because heterozygous individuals appear normal, carriers of the trait cannot be identified by eye, and instead exhaustive and time-consuming familial analysis is required in order to identify potential carrier individuals. There is a need in the art for screens that can identify heterozygous carriers of AM by genetic testing to facilitate a breeding program that eliminates the genetic defect from the population. Such a screen requires an understanding of the genetic basis of the defect, including identification of the causative mutation within the DNA sequence. Disclosed herein is a mutation associated with AM and provided are various genetic tests to determine whether apparently normal individuals carry a defective gene associated with AM. The methods, products and kits provided herein permit testing of individuals to determine whether an individual is a carrier. Individuals that are carriers can be removed from the breeding population, thereby facilitating removal of this genetic defect from the population.

While dramatic culling of suspected carriers would reduce the frequency of the mutation responsible for AM, such culling is long, expensive and can result in unnecessary reduction of beneficial genetic traits, as many of the culled animals would not be carriers of the mutation. Accordingly, there is a need in the art for a diagnostic or genetic screening test to determine whether or not an animal is a carrier of the mutation responsible for AM. Provided herein are materials and methods for screening animals to determine whether an animal is a heterozygous carrier of the mutant allele responsible for AM.

SUMMARY OF THE INVENTION

The invention features screens, methods, kits and associated probes, primers and DNA sequences for diagnosing in an animal, the genetic defect responsible for AM. In particular, provided are accurate DNA-based diagnostic tests used to assess an individual's genotypic status for AM. The methods of the present invention are used to diagnose whether a phenotypically "normal" animal is a recessive carrier of a mutated gene which is associated with AM. In an embodiment, the method is for detecting a genetic defect in bovine genome that affects one or more of the Hairy and enhancer of split 4 (HES4) gene, the ISG15 ubiquitin-like modifier (ISG15) gene, and the agrin (AGRN) gene, and more particularly, a genetic defect that comprises a deletion mutation that affects function or expression of one or more of those gene products. The methods described herein are useful in detecting a deletion mutation in the bovine genome that results in loss of AGRN gene function, loss of HES4 function and/or loss of ISG15 function. In an aspect, the deletion is a sequence that is SEQ ID NO:3, plus SEQ ID NO:10 either contiguously upstream (SEQ ID NO:5) or contiguously downstream (SEQ ID NO:4) to SEQ ID NO:3, wherein about 23,363 base pairs are deleted, as reflected by comparing SEQ ID NO:1 (wild-type gene) to SEQ ID NO:2 (mutant AM gene).

In an aspect, provided are methods, materials and/or kits for detecting a change or mutation in the DNA sequence of specific genes responsible for AM in an animal. The methods of the invention rely on the finding that the mutation associated with AM is a deletion mutation. The deleted portion of the DNA corresponds to a "middle region" of the DNA sequence. The adjacent sequence portions upstream and downstream of this middle region correspond to an "upstream region" and "downstream region", respectively. A normal AM genome (e.g., "non-mutant" or "wildtype") has upstream, middle and downstream regions in a contiguous configuration (SEQ ID NO:1). A mutant AM genome has at least one allele comprising the corresponding upstream and downstream regions in a contiguous configuration (e.g., the middle region is absent; see, e.g., SEQ ID NO:2). In an embodiment of the present invention, each strand of a wild-type DNA molecule to be tested or screened comprises three regions: (i) an upstream region; (ii) a downstream region, and (iii) a sequence between the upstream and downstream regions. In a mutant DNA molecule associated with AM, the sequence between the upstream and downstream regions is deleted.

Accordingly, diagnostic assays and DNA tests provided herein determine whether or not a deletion mutation is within the region of the genome that encodes for (or is at least partially responsible for expression of) one or more of HES4, ISG15 or AGRN. In an aspect, the deletion results in loss-of-function of AGRN. In an aspect, the deletion results in loss-of-function of ISG15. In an aspect, the deletion results in loss-of-function of HES4. In an embodiment, the bovine genome comprises the bovine DNA sequence of SEQ ID NO:1 (wildtype) and/or SEQ ID NO:2 (mutant AM—found in AM-expressing phenotype and heterozygous AM carriers), wherein the middle portion corresponds to a deletion from bases 6508 to 29,854 of SEQ ID NO:1 (cross-referenced as SEQ ID NO:3) plus an additional 16 base pair sequence of SEQ ID NO:10 that is contiguous to either the upstream end (see SEQ ID NO:5) or downstream end (see SEQ ID NO:4) of SEQ ID NO:3.

An example of an upstream region DNA sequence is at least a portion of the sequence upstream of, and contiguous to, base 6,491 or 6,507 of SEQ ID NO:1, such as the upstream contiguous 100, 200, 3500, or between about 100 to 300 bases or any subrange thereof, of SEQ ID NO:1. In an embodiment, the upstream region corresponds to bases 1 to 6491 of SEQ ID NO:1 (e.g., SEQ ID NO:6) or to bases 1 to 6507 of SEQ ID NO:1 (e.g., SEQ ID NO:7). In an embodiment, the upstream region corresponds to bases 1872 to 6491 of SEQ ID NO:1 or to bases 1872 to 6507 of SEQ ID NO:1. In another embodiment, upstream corresponds to bases 1 to 429 of SEQ ID NO:2, or upstream and contiguous to base 429 or 445 of SEQ ID NO:2, such as an upstream region having a length of 100 basepairs, 200 base pairs, or between about 100 and 300 basepairs in length.

An example of a downstream region DNA sequence is at least portion of the sequence downstream of, and contiguous to, base 29,854 or 29,870 of SEQ ID NO:1, such as the downstream contiguous 100, 200, 5,000, or between about 100 to 300 bases or any subrange thereof of SEQ ID NO:1. In an embodiment, the downstream region corresponds to bases 29855 to 35035 of SEQ ID NO:1 (e.g., SEQ ID NO:9) or to bases 29871 to 35035 of SEQ ID NO:1 (e.g., SEQ ID NO:8). In another embodiment, downstream corresponds to bases 429 to 751 or bases 445 to 751 of SEQ ID NO:2, or downstream and contiguous to base 429 or 445 of SEQ ID NO:2, such as a downstream region having a length of 100 basepairs, 200 base pairs, or between about 100 and 350 basepairs.

The DNA analysis optionally comprises PCR to amplify specific DNA sequences, thereby providing for accurate and reliable diagnostic and screening methods of the present invention. Primers are selected that flank regions of interest, including potential breakpoints or portions of the DNA sequence corresponding to the middle region. In an embodiment, a forward primer is selected that is capable of specific binding to the upstream region and a reverse primer is selected that is capable of specific binding to the downstream region. Such a primer pair cannot amplify DNA if the middle region of about 23 kb of DNA is present (e.g., wildtype), because the primers are sufficiently separated that amplification cannot efficiently occur. In the presence of the specifically exemplified deletion mutation, however, the two primers are close enough, for example less than about 5,000 base pairs, or less than 1,000 base pairs, or less than about 500 base pairs, for efficient amplification. In an exemplified embodiment, the primers are 22 bases in length and separated by 463 (or 532) bases, providing an amplified DNA product that is 507 (or 576) bases or basepairs in length. The amplified DNA product is detected by any means known in the art, including with a probe (radioactive, fluorescent, luminescent or colored, for example), nuclease assay, by a DNA sequencer, or by running the sample on an electrophoretic gel and detecting the DNA of an expected size.

Various forward and reverse primers (as well as probes) useful in the present invention are described herein and are shown in the SEQ ID NOs:1 and 2 provided in Tables 1 and 2, respectively, in bold and in bold and underline. The probes and primers of the present invention comprise those having sequences corresponding to, or a reverse complement of, the bold or the bold and underlined sequences outlined in the Tables 1-2, and any other probes or primers useful in classifying genotype for the AM mutation as a person of ordinary skill in the art can design and make based on hybridization requirements, binding specificity, and sequence homology. Reverse primers correspond to reverse complementary sequences of the DNA sequences in bold or in bold underline. The invention includes the reverse complement sequences to obtain primer and probe sequences that specifically bind to targets, including specific targets within or spanning each of one or more of the upstream, middle and downstream regions provided in SEQ ID NOs:1-10, or potential breakpoint regions. A reverse primer is paired with a forward primer having a sequence with a region identical to at least a portion of the DNA sequences of any of SEQ ID NOs:1-10, including a region identical to at least a portion of the upstream region DNA sequence. Each of the indicated primers are capable of specific binding in that they do not span a DNA repeating sequence and do not have significant homology with any other DNA sequence of similar length that could introduce uncertainty into the assay. For example, the probes or primers may have up to seven adjacent nucleotides in common and have approximately 70% homology, including 70% and greater, with the corresponding target sequence given by a portion of any of SEQ ID NOs:1-10, or reverse complement thereof. Accordingly, the probes and primers are not limited to those explicitly exemplified, but encompass other probes and primers that one of ordinary skill in the art identifies as capable of specific binding. In addition, probes and primers specific to the breakpoint regions, (shown by the triangles in Table 2 and corresponding to between bases 429 and 430 of SEQ ID NO:2 or between bases 445 and 446 of SEQ ID NO:2); upstream breakpoint between bases 6491 and 6492 or 6507 and 6508 of SEQ ID NO:1; downstream breakpoint between bases 29854 and 29855 or 29870 and 29871 of SEQ ID NO:1 are particularly useful in DNA-based analysis for determining AM deletion mutation status.

A two primer system that distinguishes between a (deleted) mutant gene and a normal gene relies simply on the presence or absence of an amplified DNA product, for example. If the primer pair flanks the potential deletion region, an amplified DNA product only occurs for the mutant and the animal is classified as “normal” if there is no amplified DNA product. Similarly, if the primer pair spans the breakpoint region (e.g., one primer specifically binds only if upstream and middle (or middle and downstream)), absence of amplified product indicates the animal has a mutant allele. Accordingly, for quality control, addition of a third primer to the forward and reverse primer pair may be desirable so that two distinguishable DNA products are generated which can then be further distinguished based on a signal, such as by size or differentially-labeled probes. Preferably, the third primer is capable of specific binding to at least a portion of the middle region so that a DNA product corresponding to the third primer and the forward primer (or the third primer and the second primer, depending on the third primer location with respect to the location of the first and third primers), is amplified. In this manner, every sample processed will have at least one amplified DNA product, and in the case of AMC two, where the amplified product can be differentially detected and can serve as an internal control on PCR. Such a three-or-more primer system addresses a concern about whether lack of signal can be attributed to deficient PCR processing/procedures for an individual sample instead of whether or not there is a AM mutation. The third primer may be a reverse primer that is paired to the first primer, or alternatively may be a forward primer that is paired to the second reverse primer.

In an aspect, primer pairs for PCR amplification are selected so as to obtain, under appropriate conditions of "no deletion mutation" or "deletion mutation", amplification product. With current reagents and PCR processing conditions, such primer pairs may be separated by up to about 6-7 kb, although most techniques are within about 600 bp, 500 bp or 200 bp. Accordingly, the methods described herein do not require an exact relative separation distance between primer pairs, so long as primers used in tests relying on detecting a difference in DNA length of two or more amplification products provide amplification products of experimentally detectable different lengths. In an aspect, primer pairs are selected to be separated, under conditions where an amplification product is desired, by less than 6000 base pairs and more than 15 base pairs.

In a particular embodiment, the DNA analysis further comprises providing one or more of a forward primer having the sequence of SEQ ID NO:11 (to specifically hybridize to the upstream region complementary strand corresponding to bases 6328 to 6349 of SEQ ID NO:1 or to bases 266 to 287 of SEQ ID NO:2), a reverse primer having the sequence of SEQ ID NO:13 (corresponding to the reverse complement of SEQ ID NO:12) (to specifically hybridize to the downstream region of bases 30,176 to 30,197 of SEQ ID NO:1 or to bases 751 to 772 of SEQ ID NO:2). Optionally, a third primer is directed to specific hybridization with a portion of the middle region and positioned to provide generation of an amplification DNA product with either of a corresponding forward primer (to the upstream region) or a corresponding reverse primer (to the downstream region). In an aspect, the third primer corresponds to a middle region target sequence corresponding to SEQ ID NO:14 (corresponding to bases 6882 to 6903 of SEQ ID NO:1; no corresponding sequence in SEQ ID NO:2, as that sequence has this middle portion deleted), and specifically a reverse complement thereof (e.g., SEQ ID NO:15). Accordingly, in the embodiment where the primers are SEQ ID NOs:11, 13 and 14, a normal allele will provide one amplified DNA product that is 576 bp in length and a mutant AM allele will provide one amplified DNA product that is 507 bp in length. An AMC will produce both size amplified DNA products.

Various methods may be used to provide classification of the sample genotype as AMF or AMC. The amplified PCR product or the DNA from the sample can be analyzed directly by providing a DNA probe (or a primer for extension) that is capable of specific binding to a region that identifies the DNA as normal (e.g., a portion of the middle region is present, or one or both of the contiguous ends of the middle and upstream or middle and downstream regions are present) or is capable of binding to a region that identifies the DNA as a mutant (e.g., the breakpoint region). Alternatively, the DNA can be analyzed by DNA sequencing and comparing the sequences to those provided herein to determine whether there is a mutation. The amplified DNA products may be further analyzed to characterize the length of the products, such as by being run on a size-separating gel. Any of these techniques may be optionally combined together to generate an improved signal or additional information, as desired.

Oligonucleotide probes or primers of the present invention can be used with any of the methods disclosed herein. Probe or primer sequences are designed based on the DNA sequences provided herein, and specifically hybridize or bind to DNA regions so as to provide information about whether or not a deletion mutation associated with AM is present, such as deletion affecting one or more of the HES4, ISG15 ubiquitin-like modifier and/or the AGRN gene. In an embodiment, the probes or primers comprise a purified oligonucleotide having a length of about 15 to about 50 nucleotides. Particular specific binding sites include those encompassing bases T429 and G430, 445A and 446C of SEQ ID NO:2 (e.g., breakpoints), by the middle region defined by SEQ ID NO:3 (or, alternatively one of SEQ ID NOs:4 or 5) and contiguously associated upstream and downstream flanking regions.

The methods and materials provided herein can be used on any animal, and is preferably used in bovine to detect the presence or absence of a AM mutation, and is particularly useful in testing animals characterized as an Angus breed, for example Angus and their composites that are susceptible to AM. The tests and materials can be used with the DNA obtained from any animal tissue or fluid. Convenient samples are obtained from hair, blood or semen.

Provided are isolated and purified nucleic acid molecules of any of the sequences disclosed herein (e.g., those of Tables 1-3, and any of the SEQ ID NOs), or including at least a functional fragment thereof. Useful primers and probes include those that specifically bind a target sequence that resides in at least a portion of a particular DNA region such as an upstream region, downstream region or a middle region. Other useful oligonucleotide primers or probes include those that specifically bind a breakpoint or those that specifically bind two adjacent regions, such as an isolated and purified nucleic acid molecule comprising at least a functional fragment of a deletion breakpoint that is the causative agent of AM. The probes or primers can be of any length and homology, so long as the length and homology is sufficient to result in specific binding to a specified target region, or any non-specific binding is confined to a region that does not adversely impact the assay. In an embodiment, the probe or primer is an oligonucleotide or a DNA sequence that ranges in size from about 15 to 80 bases, or about 18 to 60 bases, or about 20 to 25 bases. Desirably, at least 12, at least 15, or preferably at least 20 bases are homologous to the target sequence. In an embodiment, all the primer or probe base are homologous (e.g., complementary) to the target sequence. Exemplary probe or primer sequences are provided in Tables 1 and 2 in bold, and also in bold and underline.

Kits comprising any of the oligonucleotide probes or primers disclosed herein are within the scope of the invention. The kits can further comprise instructions for appropriate DNA processing, hybridization and/or PCR conditions, and for visualizing or detecting amplified DNA products.

For quality control, the kit optionally comprises DNA test samples that are a positive control (e.g., a mutant DNA sample comprising the breakpoint indicated in Table 2) and/or test samples that are a negative control comprising the middle region and associated flanking upstream and downstream regions, as summarized in Table 1 and SEQ ID NO:1. These controls can comprise DNA sequences corresponding to expected DNA-amplified products from the primers of the kit, or can be isolated and purified DNA sequences corresponding to wildtype or to normal and/or AM mutation that can be used by the probes or primers of the kit.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful. For example, there is tolerance in the specific sequence and breakpoints, and such variation may be accommodated by one or more of the materials and methods provided herein such that an operative and useful invention remains.

BRIEF DESCRIPTION OF THE DRAWINGS

FIG. 1: Photograph of a gel image demonstrating the diagnostic for identifying Arthrogryposis Multiplex (AM) in cattle. Each row represents the results from amplification of genomic DNA corresponding to 23 different animals (a total of 92 animals are shown). In the gel, the smaller amplified DNA (507 bp fragment identifies a deletion mutation) runs further than the larger amplified DNA (576 bp fragment identifies a normal allele). Thirty-one animals are tested as heterozygous for the mutation causing AM (AMC) as revealed by the presence of two bands: a 507 bp fragment and a 576 bp fragment that corresponds to the normal DNA sequence.

DETAILED DESCRIPTION OF THE INVENTION

As used herein, "diagnosing" refers to classifying an animal whose DNA is being tested into a specific genotype status related to AM. For example, an animal that is homozygous for the normal variant are referred to as AM-Free (AMF), indicating the animal has been tested for the causative mutation and has been found to be "free" of the causative mutation responsible for AM. If the individual tested is found to be heterozygous or "carriers" for the mutation, meaning that the individual possesses one normal allele and one mutant allele, they are classified as AM-Carrier (AMC). An AMC individual can pass on the mutation, and due to the manner of passage of genetic information to off-spring, the frequency of passage to offspring is about 50%. Generally, an individual homozygous for the AM mutation is an animal expressing the AM phenotype, meaning that the affected calf can be diagnosed or classified simply by observing the calf's phenotype, meaning testing is unnecessary in order to identify the animal as AM-Affected (AMA). As discussed AM is a lethal mutation so that AMA individuals do not survive to breed, and so the test, in and of itself is not necessary to remove the affected individual from the breeding pool. In various embodiments, however, testing of the genetic materials from AMA animals is provided as a positive control, such as in methods and kits for diagnosing AM. In addition, testing of such individuals can be beneficial to confirm the underlying basis of the mutation and to confirm the mutation remains conserved with respect to the deletion mutation provided herein.

EXAMPLE 1

Characterization of the Genetic Basis of the Mutation

The accurate identification and subsequent selection against carriers of the AM mutation is the only method that can be used to eliminate this genetic defect from the population, without concurrent loss of genetic resources due to culling based only on pedigree. The development of a method to accurately and efficiently determine the genotype status of an individual is dependent on understanding the molecular basis of the defect (i.e., identification of the causative mutation within the DNA sequence). The mutation causing AM is identified as a deletion of about 23,363 base pairs. This deletion encompasses the 5' regulatory region of the hairy and enhancer of split 4 (HES4) gene, the entirety of the ISG15 ubiquitin-like modifier (ISG15) gene, and the 5' regulatory region and first two exons of the agrin (AGRN) gene. The role of HES4 and ISG15 in disease pathology is unclear, however based on the functional role of AGRN in development of the neuromuscular junction it is the most likely causative gene for the pathology. The mutation results in a complete loss-of-function of AGRN thus producing the disease phenotype when an animal is homozygous for the deletion-containing chromosome. Gene "knock-out" models of AGRN in mice result in similar pathologies (Harvey et al., 2007). Using the DNA sequence information that has been generated, various DNA-based diagnostic tests are provided to accurately determine an individual's genotype with respect to AM (particularly AMC or AMF). Thus, the genotype of an animal can be obtained by analysis of any DNA containing sample such as blood, semen or hair follicles.

Table 1 summarizes relevant technical data corresponding to the identification of the causative mutation for AM. SEQ ID NO: 1 (also provided in Table 1) corresponds to the bovine DNA sequence that encompasses the region affected by the deletion mutation. Exons corresponding to the protein coding sequence of HES4 (red—labeled "R"), ISG15 (green—labeled "G"), and AGRN (yellow—labeled "Y"), are highlighted. The deletion mutation causing AM is highlighted in grey (corresponding to bases 6508 to 29854 of SEQ ID NO:1; cross-referenced as SEQ ID NO:3). Note that exons 1 and 2 of the AGRN gene is contained within the deleted segment as well as the entirety of the ISG15 gene.

Exemplary primer sequences used for sequencing, defining the deletion breakpoint, and diagnostic testing are in bold and bold/underline with forward primers in green and reverse primers in red. Various specific SEQ ID NOs and descriptions thereof are summarized in Table 3.

Table 2 and SEQ ID NO: 2 is generated by PCR amplification across the deletion breakpoint boundaries in affected calves and heterozygotes. Triangles in the sequence of Table 2 indicate the position of the deletion breakpoint that corresponds to the joining at a simple 16 bp sequence motif (highlighted in orange). Alignment between SEQ ID NO:1 and SEQ ID NO:2 demonstrates that SEQ ID NO:2 represents flanking DNA sequences separated by 23,363 bp on the normal chromosome.

AM is observed in Angus cattle and Angus influence cattle. In particular, any animal that can be traced back to a particular individual by breeding records as the probable source of the mutation (e.g., Rito 149 of J845 7T26 Registration 9238034) is potentially a carrier of the defective gene responsible for AM. Analysis of lineage lines indicates that AM is an autosomal recessive disease. Accordingly, many animals in the breeding population are potential "heterozygous carriers", e.g., animals that have one copy of the gene responsible for AM (AMC). This number is estimated to be as high as 10%. The methods and compositions of matter presented and claimed herein are particularly useful for diagnosing whether or not an animal is a recessive carrier of the defective gene responsible for AM. Animals identified as AMC can be removed from the breeding population so as to breed out the gene responsible for AM, or alternatively, bred with AMF with the offspring then tested for the AM mutation. The tests and materials provided herein, however, are compatible with different breeds such as breeds wherein this mutation may arise in the future.

As used herein, "DNA sample" includes the part of the bovine genome that is a locus for AM. In particular, it is that part of the genome associated with expression of one or more of AGRN, HES4 and ISG15 genes or gene products. Methods provided herein are, accordingly, useful for detecting whether or not there is a deletion mutation that when inherited from both parents results in phenotypic expression of AM. An animal that is a heterozygous carrier of this deletion mutation is said to have a mutation that is associated with AM or is an AMC.

"Obtaining" is used broadly to refer to any method of obtaining a biological sample that contains DNA, and specifically a sample that contains at least a portion of the genome spanning a region associated with the mutation that is a causative agent of AM. The sample can be from any tissue, so long as the sample contains DNA that is not significantly degraded, and can be fresh, frozen or otherwise preserved. For example, blood, semen or hair are relatively easily obtained and can be processed for immediate analysis or stored for later transport, processing and analysis. Although DNA may be obtained from other types of tissue containing DNA such as skin or muscle, those types of tissue may not be preferred as they are more difficult to obtain, store, transport and process compared to blood or semen.

As used herein, "analyzing" broadly refers to any technique that reveals genetic information, particularly whether or not a DNA sample contains an allele comprising a mutation associated with AM. In a preferred embodiment, the technique comprises PCR processing to amplify selected DNA sequences to yield information about the status of the sample. Other techniques, including DNA hybridization with probes, DNA sequencing, DNA separation by gel electrophoresis and others known in the art can be optionally combined with PCR to generate improved signals.

The portion of the bovine genome that is involved with AM, including those portions useful for determining whether an animal is normal or a heterozygous carrier of AM, can be divided into three regions: (i) an upstream region; (ii) a downstream region; and (iii) a middle region, wherein the middle region forms a contiguous configuration with the upstream region at one end and the downstream region at the other end. "Contiguous configuration" refers to two or more DNA sequences forming a continuous DNA strand, wherein there are no additional DNA sequences between adjacent strands. Processes and materials provided herein for identifying carriers of AM is based on the discovery that the AM mutation is associated with deletion of the middle region, such that the upstream region and downstream region form a contiguous configuration. DNA analysis of known AM mutant genes reveals that the mutant gene has a deletion, whose size and location tends to be conserved among different animals. With this information; methods and related compositions of matter are presented herein that are useful in determining whether or not an animal is a recessive carrier of a AM mutant gene by determining the presence or absence of this middle region, either directly (such as by probing) or indirectly (such as measuring length of an amplified product, with one unique length indicating no mutation and another unique length that is different indicating mutation).

Polymerase Chain Reaction ("PCR") is a technique in which cycles of denaturation, annealing with primer, and extension with DNA polymerase are repeatedly used to amplify the number of copies of a DNA segment, up to and greater than $10^6$ times. PCR and associated PCR conditions are known in the art and are described more fully in U.S. Pat. Nos. 4,683,195 and 4,683,292, which are herein incorporated by reference. A "primer" is a single stranded oligonucleotide or DNA fragment which hybridizes to a DNA strand. In PCR, primers are generally paired, with a 5' forward primer that hybridizes with the 5' end of the DNA sequence to be amplified, and a 3' reverse primer which hybridizes with the complement of the 3' end of the sequence to be amplified. The amplified DNA sequence encompasses the target sequence hybridized by both primers, as well as the intervening sequence between both primer target sequences. Any portion of the DNA sequences provided herein can be used as a probe or primer, so long as the probe or primer sequence specifically binds one target. Such specific binding improves the reliability of DNA-based screens useful for identifying carriers of the AM mutation.

The oligonucleotide primers and probes are generally selected for their ability to specifically bind to at least a portion of the upstream, downstream or middle DNA region. "At least a portion" refers to the embodiment where the target DNA sequence spans adjacent regions, including upstream-downstream (e.g., AM mutant), upstream-middle (e.g., no AM mutant) or middle-downstream regions (e.g., no AM mutant). In an aspect, the oligonucleotide is isolated and purified DNA.

As used herein, "Angus" refers to any bovine animal with any Angus ancestry.

Analyzing DNA encompasses any means known in the art: cleavage, where cleavage is dependent on whether or not there is a deletion mutation; hybridizing of probes, where probe binding is dependent on whether or not there is a deletion mutation; PCR amplification, where the presence of amplification products, or the size of the amplification products where the size depends on whether the deletion mutation is present; DNA sequencing; etc. The invention can be practiced with any DNA detection methods known in the art, including any future-arising detection methods. Analysis methods rely on the discovery of a deletion mutation that is associated with AM, as reflected in the difference between the wildtype genetic sequence (SEQ ID NO:1) and the AM mutant genetic sequence (SEQ ID NO:2), and more specifically, the recognition that a large deletion mutation that is located within a defined location in the genome is associated with the disease (SEQ ID NO:3, corresponding to breakpoint between bases 6491 and 29855 or 6507 and 29871 of SEQ ID NO:1). Some examples of methodology that can be useful in detecting whether or not a large deletion is present include U.S. Pat. No. 4,683,202 (Process for Amplifying Nucleic Acid Sequences), U.S. Pat. Nos. 6,013,444, 6,225,093 US Pat. Pub Nos. 2006/0063191 (Detecting Nucleic Acid Deletion Sequences) and 2009/0239212.

The typical DNA deletion of the AM gene is greater than about 23 kb (e.g., the difference between the central portions of SEQ ID NO:1 and SEQ ID NO:2 is a 23363 length deletion in SEQ ID NO:2 corresponding to the sequence of SEQ ID NO:3 plus the sequence of SEQ ID NO:10 that is either contiguously upstream or downstream of SEQ ID NO:3, such as SEQ ID NO:4 or SEQ ID NO:5). Accordingly, if one of SEQ ID NOs:4 or 5 is present (e.g., the genome is from wildtype), under typical PCR conditions (e.g., "short PCR conditions"), a primer pair located on either side of this deletion sequence will not generate any amplified product (the primers are spaced too far apart). If, however, the mutation is present and one of SEQ ID NO:4 or SEQ ID NO:5 is deleted from SEQ ID NO:1, the primer pair is then sufficiently close to result in generation of an amplified DNA product that is then detected. Accordingly, a person of ordinary skill in the art will recognize that any number of probes/primes may be designed and constructed for use with the DNA tests described herein, so long as the probes or primers exhibit specific binding to the target of interest.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The present invention contemplates nucleic acid sequences which hybridize under low, moderate or high stringency hybridization conditions to the exemplified nucleic acid sequences set forth herein. Duplex formation and stability depend on substantial complementarity between the two strands of a hybrid, and a certain degree of mismatch can be tolerated. The more stringent the hybridization conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak (1987) *DNA Probes*, Stockton Press, New York, N.Y., pp. 169-170, hereby incorporated by reference. For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5 times Denhardt's solution, sonicated salmon sperm DNA (50 μg/ml), 0.1% sodium dodecylsulfate (SDS), and 10% dextran sulfate at 4° C., with washes at 42° C. in 0.2×SSC and 0.1% SDS.

An example of high stringency conditions is hybridizing at 68° C. in 5×SSC/5×Denhardt's solution/0.1% SDS, and washing in 0.2×SSC/0.1% SDS at room temperature. An example of conditions of moderate stringency is hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) supra or Ausubel et al. (1995) *Current Protocols in Molecular Biology*, John Wiley & Sons, NY, NY, for further guidance on hybridization conditions.

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'. This invention encompasses complementary sequences to any of the nucleotide sequences described or claimed herein.

A "functional fragment" of a nucleic acid is a partial sequence of the nucleic acid molecule such that the functional fragment has utility as a probe, primer or a target sequence for specific binding to a complementary probe or primer in the present invention, for example. A functional fragment that is a probe or a primer is useful for diagnosis, sequencing or cloning of the portion of the DNA genome that is associated with AM, including the portion of the genome that encodes or regulates expression of one or more of HES4, ISG15 or AGRN genes or gene products thereof, and that portion of the genome that comprises a deletion mutation associated with AM.

In accordance with the processes provided herein, there is provided a purified and isolated nucleic acid molecule which regulates and encodes for AGRN protein. Desirably, the nucleic acid molecule is a DNA isolated from Angus, Angus composites or other bovine suspected of having the AM mutation. Further encompassed are nucleotide sequences for probes and primers to various portions of the genome associated with the AGRN gene, and in particular probes and primers that bind specifically to an upstream region, downstream region, or a middle region, wherein the middle region corresponds to a mutation deletion associated with AM. Given a particular sequence, the generation of primers to that sequence is well known in the art. Sequencing and diagnostic primers are typically 20 to 28 base pairs, more preferably 22 base pairs in length, and generally match the sequence of interest between approximately 90% to 100%, most preferably approximately 100%. Primers are typically approximately 20 to 34 base pairs in length, more preferably 21 to 24 base pairs in length, with annealing temperatures in the 50 to 70° C. range. Gene probes are preferably approximately 1 kb in length comprising the gene of interest to be probed.

Particular probe or primer sequences are selected for their ability to bind a single specific region of the DNA sequence in one or more of (or regions thereof) SEQ ID NOs:1-10, 16-19 (e.g., "specific binding"), but not to other genomic loci. As used herein, "specific binding" or "binds specifically" refers to an oligonucleotide (e.g., a primer or probe) that is sufficiently selective in hybridizing the target sequence so as to result in DNA analysis that is reliable and accurate in identifying DNA having an AM mutant allele. A probe or primer that is capable of specific binding to a DNA target sequence does not hybridize in significant amounts (e.g., measurable) amounts to a non-target sequence. To ensure specific binding, a number of different considerations are employed. For example, none of the target sequences should be located in DNA repetitive elements. In addition, potential target sequences can be analyzed against the remainder of the sequence to determine whether there are other regions with significant homology. "Homology" or "sequence identity" means the proportion of base matches between two nucleic acid sequences. When sequence homology is expressed as a percentage, e.g., 50%, the percentage denotes the fraction of matches over the length of sequence that is compared to some other sequence. Gaps (in either of the two sequences) are permitted to maximize matching. When using oligonucleotides as probes, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%). A primer or probe sequence of the present invention is considered capable of specific binding if there is less than 80% homology, less than 70%, and preferably less than 50% homology (corresponding, to a 20 base pair probe or primer having less than 16, less than 14, or less than 10 identically aligned bases) to other "non-target" sequences.

Hybridizing the probes or primers with the DNA sample under stringent conditions also reduces the likelihood of binding to regions other than the target region. In general, probes or primers having higher homology to other sequences besides the target sequence can be hybridized under more stringent conditions than probes or primers having lower homology.

For regular PCR conditions, the location of primer pairs are preferably separated by less than about 6,000 base pairs, less than about 2,000 base pairs, less than about 500 base pairs, or separated by a range that is less than or equal to about 700 base pairs and greater than or equal to about 400 base pairs, thereby ensuring efficient amplification. Processes provided herein are not, however, limited to a specific primer separation distance; the constraint is the ability of the primers to generate amplified DNA. In an aspect, the method for identifying AM carriers relates to a PCR method and primers that, when expressed, provide an indication of whether the sample is from an animal that is a carrier of AM. In an aspect, the identification is by determining a length of the expressed fragment, with one length indicating a normal sequence and another length indicating a mutated sequence. In an aspect, the primers are selected so that the normal chromosome amplification fragment is longer than the fragment amplified from a mutant chromosome corresponding to the deletion mutation. In an aspect, the lengths are reversed.

As used herein, the terms "isolated and/or purified" refer to in vitro isolation of a DNA molecule from its natural cellular environment and from association with other components of the cell, such as nucleic acid, so that it can be sequenced, replicated, amplified and/or expressed. An "isolated and purified nucleic acid molecule" is a nucleic acid the structure of which is not identical to that of any naturally occurring nucleic acid. This term covers, for example, DNA which has part of the sequence of a naturally occurring genomic DNA, but does not have the flanking portions of DNA found in the naturally occurring genome. The term also includes, for example, a nucleic acid incorporated in a vector or into the genome of a cell such that the resulting molecule is not identical to any naturally occurring vector or genomic DNA.

EXAMPLE 2

DNA-Based Tests to Detect AM

Those of ordinary skill in the art will recognize that any number of DNA-based diagnostic tests can be developed that detect the presence or absence of a deletion on the order of greater than about 15,000 base pairs, or greater than about 20,000 base pairs, or about 23,363 base pairs (see, e.g., U.S. Pat. Pub. No. 20090239212). Given the length of the DNA sequence of SEQ ID NOs:1 and 2, the invention tolerates variation in both the precise breakpoint location and breakpoint sequence. For example, primers and probes can be designed so that the breakpoints (e.g., between bases 429-430 and bases 445-446 of SEQ ID NO:2) can vary, for example by plus or minus 20 base pairs, or plus or minus 10 base pairs, or plus or minus 5 base pairs or less, without affecting the ability of the probe or primer to specifically bind the target sequence and generate an output signal that can be used to determine the presence or absence of a deletion. One example of such designing is to ensure the probe/primer sequence is of adequate length, and also to target sequences that are greater than 5, greater than 10 or greater than 20 base pairs away from the potential breakpoint location.

Any DNA test that detects, directly or indirectly, the breakpoint of the sequence that is associated with AM (e.g., between about bases 6,507 to 29,870 of SEQ ID NO:1 with the 16 base pair sequence of SEQ ID NO:10 contiguously either upstream or downstream of that deletion) of SEQ ID. NO:1 (wildtype) and corresponding mutant carrier (SEQ ID NO:2) may be used with the claimed methods, processes and kits. In particular, various methods may be used to detect corresponding breakpoint between about base T429 and G430 or A445 and C446 of SEQ ID NO:2 (as indicated by the triangles at these positions in the SEQ ID NO:2 shown in TABLE 2), whether directly (e.g., presence or absence of a signal or an amplification product) or indirectly (e.g., comparing a detected signal to a reference or another detected signal to classify the signal as arising from a mutation or a normal sequence) can be used as the basis of an assay for testing whether a subject is a carrier of the AM mutation. Such tests include but are not limited to DNA sequencing, hybridization and allele-specific extension. Any one or more tests may be used as desired, including primer extension, 5' to 3' exonuclease assays, or PCR, so long as a signal is generated that can be detected or measured either quantitatively or qualitatively.

For example, PCR can be used to amplify appropriate DNA portions, and the amplified DNA run on a gel that separates DNA by size or other means for identifying DNA length. In this example, such a PCR test uses three different primer sequences, a first (forward) primer (primer 1) that binds upstream of the breakpoint, a second (reverse) primer (primer 2) that binds downstream of the breakpoint, and a third (reverse) primer (primer 3) that specifically binds to the middle region, corresponding to the deleted portion of DNA associated with the mutation responsible for AM. In this manner, as summarized in TABLE 4, primer pair 1-2 will generate an amplification product "I" if the deletion mutation is present. Similarly, primer pair 1-3 will generate amplification product "II" only if the middle region is present (e.g., no deletion mutation). Accordingly, if all three primers are used there will either be one amplified product (for AMF or AMA, but the AMF and AMA samples produce different length products) or two amplified products (for AMC—one allele "normal" the other allele having the deletion mutation for AM). Alternatively, if only primer pair 1-2 is used, a generated amplified product that is detected will indicate an animal that is at least AMC.

The actual location of the target sequence to which the primer specifically binds is not critical, although under "normal" PCR conditions (e.g., not long range PCR conditions, see U.S. Pat. No. 6,225,093) it is preferable if the target sequence is within about 5 kb, or within 1 kb, or within about 400 to 600 bases of a potential breakpoint site and the other end of the to-be-amplified DNA sequence. Although the exact position of the primer is not critical, in one embodiment where the test is based on differences in amplified DNA length indicating the condition (e.g. AM carrier animal versus a normal animal), it is important that the difference in DNA amplification lengths be detectable or observable. In an aspect, the difference in DNA length between an AM carrier and a normal is 10% or greater (e.g., 576 bp in normal animal and 507 bp in an AM mutant). Of course, the required difference in length to be detectable or observable depends on the assay used to characterize length. For example, to reliably detect difference in lengths by running the DNA on a gel, an about 10% or greater length is desired. Alternatively, if the amplified products are sequenced, no difference in length is required.

In one embodiment, the primers used with respect to a test that provides genotyping based on length of amplified product are as follows:

First (forward) primer binding upstream region (SEQ ID NO:11): corresponding to bases 6328 to 6349 of SEQ ID NO:1.

Second (reverse) primer binding downstream region (SEQ ID NO:13): reverse complement of SEQ ID NO: 12; corresponding to bases 30176 to 30197 of SEQ ID NO:1.

Third (reverse) primer binding to middle region (SEQ ID NO:15): reverse complement of SEQ ID NO:14 (corresponding to bases 30176 to 30,197 of SEQ ID NO:1.

As discussed, this combination of primers is used under standard PCR conditions to generate successful test results.

DNA tests provided herein may be broadly characterized as "direct tests" or "indirect tests". In a direct test, the detection or absence of a signal by itself is sufficient to identify the sample as at least AMC or as AMF. One example of a direct test is a method using only the two primers of SEQ ID NO:11 (bind upstream region) and SEQ ID NO:13 (bind downstream region) in that if a signal is generated, that is an indication of a mutant allele (see Table 4). If no signal is generated, the sample is AMF. In contrast, if all three primers are used, it is necessary to examine another parameter associated with the amplified products to assess the genotype (e.g., amplified product length), and such a test would be considered "indirect". Other examples of direct tests include a probe that only binds if the deletion mutation is present, or primer extension where the primer only hybridizes to bovine DNA having the middle region deleted.

EXAMPLE 3

Assay Characterization

The first and second primers provided above (e.g., SEQ ID NOs:11,13) are each located on a separate side of the breakpoint. Accordingly, in a normal allele there is no amplification product attributed to the first (SEQ ID NO:11) and second (SEQ ID NO:13) primers as the intervening about 23 kb sequence between the first and second primers prevent generation of PCR-amplified DNA product. If there is, however, an allele for the AM disease (e.g., the intervening about 23 kb sequence is deleted), a first DNA product is amplified, wherein the DNA corresponds to the region encompassed by the first and second primers. The resultant length of this first DNA product is $L_{12}$. Alternatively, the first (SEQ ID NO:11) and third (SEQ ID NO:15) primers may be used to generate a DNA amplified fragment having length $L_{13}$ and indicating a normal allele. The third primer resides in the deleted portion, and so a DNA product is not amplified for those alleles carrying the AM mutation. DNA of length $L_{13}$ is generated only if the DNA sequence does not have the AM mutation. By selecting precise target sequences, the size of the amplification products generated by primers 1 and 3 ($L_{13}$) can be different than the size generated by primers 1 and 2 ($L_{12}$). The amplified DNA can be run on a gel to separate DNA by size, with the observed pattern dependent on whether or not the DNA from the subject to be tested is a carrier of an AM gene, as summarized in Table 4.

FIG. 1 shows that two bands in a lane indicates a chromosome having one allele that has the mutation and another allele that is normal (e.g., see the top row, lanes: 1, 11, 13, 16, 18 and 21), thereby identifying the subject as a heterozygous carrier (AMC) of the AM gene. If only one band is observed, the subject is either normal (AMF) or the sample is from an individual that expresses the AM phenotype (AMA) (e.g., both alleles have the AM mutation). In this example, the single amplification product indicated by those lanes having only one band indicate AMF based on the 576 by size compared to the smaller 507 bp size for deletion mutation allele.

FIG. 1 demonstrates one embodiment of a working diagnostic assay for both chromosomes. The exemplified primer sequences used for simultaneous amplification of fragments corresponding to either the normal (Table 1) or mutated (Table 2) sequence are highlighted in blue (indicated by "B") in Table 1 (all three primers) and Table 2 (two primers—the third primer that would bind the middle region does not bind the mutant allele). The DNA fragment amplified from the normal chromosome is 576 bp in length and the fragment amplified from the deleted DNA sequence is 507 bp in length.

The diagnostic assay is supported by two independent validation experiments including blind analysis of 91 samples of known genotype status based on progeny testing and analysis of phenotypically normal individuals of suspect pedigree. Results of the blind sample analysis are 100% concordant with the known genotypic status of the individuals. Among all phenotypically normal individuals of suspect pedigree no individual was genotyped as homozygous for the deletion mutation, indicating the association of the disease phenotype with only homozygous individuals (Chi-square=26.23, $p<0.0001$). Twenty-eight of 28 affected calves are genotyped as homozygous for the deletion. Frequency of the mutated allele is estimated at 10.52% by genotyping of 1,896 individuals.

As summarized in Table 4, the third primer is not technically required in order to distinguish a normal animal from a heterozygous AM carrier. For quality control reasons, however, the third primer is optionally present and ensures that the DNA has been appropriately amplified and detected. As known in the art, the DNA need not be run on a gel, rather probes specific to each of the amplification products can be used, including radiolabeled, fluorescently labeled or any other detection substances and associated means for detecting the substance. Size separation and DNA labeling with, for example ethidium bromide is, however, a low-cost and easily performed assay for detecting AM heterozygous carriers.

In an aspect, the amplified DNA products are detected, thereby identifying heterozygous carriers of a gene that is associated with AM. In an embodiment the DNA product is detected by running the DNA on a size-separation gel, wherein the expected sizes of each DNA product is known. Isolated and purified DNA sequences of the present invention corresponding to (1) normal, and (2) mutant can be used to ensure PCR conditions and DNA analysis is functioning appropriately.

A unique, DNA-based diagnostic test that accurately determines the (AM) genotype status within cattle populations, including the Angus breed, through analysis of DNA containing samples i.e. blood, semen or hair follicles is important for eliminating this genetic defect from the population. Such a test eliminates the need for parental validation. FIG. 1 is an example of one such test where PCR amplification of the DNA from each individual is used to determine AM status.

As understood in the art, genomic DNA comprises a sense strand and an antisense strand that is complementary to the sense strand. Unless expressly indicated otherwise, the sequences listed herein, are to the sense strand, running 5' to 3'. Accordingly, the invention comprises the corresponding antisense sequences that are complementary to the listed sequences, and further include the reverse complementary sequences of all the primers and probes disclosed herein.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a temperature range, a size or separation base-pair range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art. All tables attached hereto (e.g., Tables 1-4) are part of the specification.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

U.S. Pat. Nos. 6,759,192, 5,498,521, 6,013,444, 4,683,202, 6,225,093, 6,306,591; U.S. Pub. Nos. 2006/0063191; 20030203372; 20090239212; WO0246465, GB012566; GB0103156; GB0030076; AU0220920.

TABLE 1

| SEQID NO: 1 |
|---|

AGGACCATGGAGCCTCCCCACACCTGGAGCTGCTGAGCCCTATCCCACGTGCTAGACAGAG
TAAGGGGTGCTGGGGGATCCTAGCGAAGGGAAGTCCTCCTCTTCACCAGCCTCTGGCCCAC
TTGTGGGTAAAGACGGGAAGGCAGGAATTGGCCCCCACGTCCCCACACAGACATGCAGACT
TTTTGTTTGAAGCAGGAGCCCAGGAGGTGAGCCCAAAGTCACCAGGTGGGTGTCAGGGTCA
GGCAGGACACCAAGAAGAGACCTCTGAAGCAGCATCAGCCAGTTGCCTCTTGGTCACCATG
GACACCAGGCTGCAAAGAAGGTTGATGTGCCCACTGGGGACAGGTCAGTGTGGCCCTGGGG

GCAGGTTGCAGGGTTTGTGCTGGGAATGGCAGGGCTGATGGGAACAGGCCTCTCTGGGCAG
GGCAGTCAGCTCTGTGGTTCCCAGCACGGAGCATTGCCCATGCCTGTTTTTGTTTGAAATC
TGGGGCCCCAGAACCCCCAACACCATGTTCTGATACAGTGTGCCCCCTCAGTTACTGAAAC
AGAAATGGCCCTAAGCCCTGCCCACAAGCCACAGGGATGGGGCCTGGGCTGTGGCTGGTCA
GCCCAGGATGGGAATGGAAGGGGACAGGGGGCTGGCCTGTCCCTGCACCCGCAGCTGGCAC
TCACAGGGGAACTGCTTCCCAATGGACATGAGTCCAGTCTGCTCTGCTCATCACCACCACT
GCAAGGGCTGTTTCTGGGCCTTGCTCCACCCATCCTCTTCCACAACCCCATCATCAAGTGG
GCACGTGATGCTGGAGGCCCTGGGTGACCATGGGCACATTAGTTGTATATTGCTATTGTTA
CTTACAATAACTTTAATTTTACATAAAACATTGTTAATTATAGCTGTACAACAAATTAACC
TACAATTTATCCGTTTAAAACAACAAACACATTATCTCACACAATTTCTGAGGGATAGGAG

TCCTGGAACTGCTCAGCTGGGTGGTCCCGGCTCTCAGTCTCTTCGGATTGCTACTGAGATG
TCGGCAGCAGCTGGGGTCCCAGCTGAAGGCTGGAGACCAGCTTATAAACCCCACACTCTGT
TGGCCGCTCCATAGCAAAGGACAGCTGGCCTCCTCCAAGTGGAGGATGTTAGAGACAGAGA
GAGACAGGCCAGGATGCCCCTGCGACCTCATCTTCTACAGGACCTTACTGCTGATGCAGGT
CAACCTCAGTACATTCAGAGGTAGAGTACCAGGTCGGGGCTCTTGGGGGGGCTGCCTCCTG
GGAGGCTGTCAACCCCAGGGCCTGTTTCCTTGCCCAGTGGTGCCTCCCAGGATAGGTATGG
CCCCTAGAGCTTCAAGGGGCAGAGAGCAGCCAGACACGGCTCCAGAACCCTCTGGGCTCAG
CTTCTTTCTTGGGGGAAAGGGGAGCAGGTCCTGGAGCCTAGAGGAGGCTGTTGGGGCCTGG
AGATAATCAGGTGATCACAGGAGCTCTGGTTGGGAAGCTAAGGGCTCACCTTTCAAAAGTC
AAGGCTCCCAGGAGCCCCAGGTCCTACCCCATTTCAAACTCCCAAGTACCTGGAGTTTTCT
GGGCCTGGCGAGGCCGACTGCTGTCACCGTTAGGACCAACTCTTTCTCCAGATTTCAAACA

TABLE 1-continued

| SEQID NO: 1 |
|---|

CCTATGATTTGCTGTCATTGTTAGTCCCCAAGCCCTGACCTCACAGGCAAGAAAGAGGGAC
CCAGAGTCACAGGGTTCCACAGGGCGAGACACCCACAGAGGCAGGCAGAGCACCTGACTAC
ACACAGGAATTCAGCAAACACTCATTGACCCTTGGTCCCCACCAGGAACTGGNNNNNNNNN
NNNNNNNNNNNNNNNNNNNNNNNNNNNNNNNNNNNNNNNNNNGGATTGCGGTGCAGAGGAAT
TCCCCAGAGCCCCTCTGAGGCAGGGGAGGGACAGGCAATGGGTGGAAGAGTGGGGAGGGTG
GGAGGAAGAAGAGTCCACCCCAGCTCTCCACAGACCAGGCAGGGGTCCAGGCTGAGTGTGG
AAAGGGCCATGGCTCCACCCCCAGCAGACGCCAGGATACTGCCCTCAGCTGCCCAGGGGCA
GCCTGGGGAGGGGCCCAGCCTCAGCTGTGCTTCCTCAGACTCCCCTAATCTAATCAAGGGT
GACACTCCTTTCACCCAAGCTAATTAATGAGGCCTGTATGGCCTGAGCGTCTTTCTGTTCC
AAGCAGGTACTGGGGATAGGAGTGAGTGACACAGACAGGGCCCTGGCTTCCAGAGCCCTTG
GAGCCTGGGGTGGCTATCTCAGGTGGGAAAGTGGGGAGAGAACCTCGGGGGGCAGGGAGGG
GGCTGAGTAGGGAAGGGCCAAAGGGGGCAGGGAAGGGACAGAGACACGAGGAACTTGCCTG
TCTGAGGAACAGTGTGGTTCCCTCAGAGCCGGAGAGGTCCCTGGAGGGCTGACAGGGGCCT

CAGCACAAACACCTCTTTGGCGACAGCGTCTTGAGGACAGATGACCAGGAACAGGAAGTAA
GGAAGTAAAGGGAAGCACAGCCCAGGAACAGGGGGATCTGGTTTGACACTGTGATTGCCCC
CTCCCTGAGGAGTGATGACCCGAGCTCCATGTGACCTTCCTGGGCAGCCCTCCTCCCTCTG
GCCACCAGGTGGGGAGATCCCTCTTATTCTTTCAGGCCACGTGGAACCCAGCTCTGAGGAG
GCCTTGTCCACCCCTCTACCCACCCAACCACCTGGCTTCATATCCCAAAGTCCCTTGCCTT
CCCCTCCTGCACTGAGCCTCCACCCCAAACAGCTCCCCTTTCCCAAAAAAGCTGAACTTCT
GGCTCCTGAAATGGACCCTCTGCAACTCTTCTGCTGGGAGGGCTCCCAGGCTGGTCAGCAG
TAATGCCCCCACAGTCCTGCTGGTGACCCAGCTCTCTGAGCCTCCCCAGGGCCTGGACCAG
TGAGTGTGTGCAGGTCCCAGGGTGTGGCTCCCGGCCCACATGGCTGCCACTGCCCCAAACC
ACTGGCCCAGACCCTGGACACCCAGGGAGATGGGCCAGGCAGCCAGAGAGCAGGAGGGGAC
TGGCTTGGTGGGACTTGGAGGGCCCTGCTTGGTGTGCACGGCTGAGTCCTGGAGGGCAGAT
GAACCTTGGTCAGGAACTGTTGGGGTCATTGGAGGAGGAGATAAGCCTCTAGCAGTGACTA
ACCCTCCTCCTCCCTGATGCTCCCTGGCCAGGCAGGTAGCTGGCAACCATCTGATGAAATT
GGCTGTGGGTGGGAAACCCATCTTGCCTTGACCTCAGAGGGCTCAGGATGAGACACTGCAG
TGTCAGCCACATGACTCAACCACCTCCTCACTGCCCCTGGAGCACAGCGTCCAGCAGCAGC

CTGAGGAGACCTAGGACCACAGGACAGTGGCTCCCCGGCCAATGCCCCACGCTGGCTAGGA
TCACTGTATTGTGGGGTCAGCATAAAGCCAGTGTTCAAGACAGGAGCATAGGCCTGCCAAT
GAACCCCCAATTCCTTCCTACTGTCGGGGGACTCCCTCTCAGGGGAGGACTGGGCTCTGGC
GGGAGGTGAGCCCCAGTACAAAGTGCCCTTTGTCAGGCCGGTTGGGGGCCCTGCCTCTAGG
ACTCAGATGCCCTCTTCTGCTGGCCCCCATCTGCTGGGCAGAGACTGGCTTGGGGCAGGCT
TGACCCACAGGTGCCAAGAGTAGTTCTGTGCTCCCCCGGGAGAAGGCAGGCGGTGCACCAG
GCCAGAACCCAAGCTTCAGCCCACCTCAGCCCCAGAGACAACAGCGTGCACACGTCTCTGC
CTTCCAGGGGCCTCAGGAGGGGTTGCGGGGAGAGAACTGTGCCCCAGGAGGATGCACGACC
TCTTCTCAGCACTGGGAGACGCTCTGGGAAAGTGGTAACTGTTCCAGTCCTGCCTGAGCCC
CCCAGGGACATCTCACACACACCCTCCTCCCTCGAGGCGGTCGGCTTCAGCGCAGAGGGAC
ACAGCCAAACTCAAGGCCGGGCGAACCCCTGCGCGGCGCACCGGCCGGCCCAGGTGGGAGC
TGAATAAATCCCCACGGCCCGGCCCGGCCCGGCCCGCCCCGCCCGTTCATGAGAAGACATC
AACCGACCCCGGCGCTGGGCCTCGGCCAAACTGGACCCTTCACGAAGACGACAAAACAAAA

TTCCCTACCCGATCTCTGGAAATAACCATTTTCTGGCACAGTCTCAGTCGGTTGTAGGGCC
GCGGTCTCACCGCAGCCACGGCCTCCAGGGCCGCCCTGGCCCTGAGCCCCGGTCCCGGGG
GCGGCCAGGGCCAGCCCGGGCAGGAACATGGGTGCCAAGGCCGCCCCGGGCCGGCAAGG
GGCAACGGCCGTCAAAGGCTGGCGGCCGCGGCCGGCCTGCGTAGATCTCGGGCTCCTGGGC
TTCAGTGGCTGGGCCAGTGGAAGCGGGCGGCGCGGCGCCCCAGCCGGGCCAGGCAGGCT R
GCCAGATGGCAGAGCAGACGAGACCGCACCTCCGCAGGGACGCCCTCGCAGCCAGCCAGGA
AGCGATTCACTTCGGCCAGACACTCATGGAAGCCGGCGGGATACTTGCCCAGGATAGCGGG
GTCCGAGCGGAGGGCAGCTGCGGGGGTGGCAGGGACAGGCGGTCGGCGCCCGCGGCCTCAG

CCCCGGCCCCTGAGCCCTCGCCGCCGCCCTCGCCTCACCTGTCACCTGCACGGCCGCAGG R
CTCTGCAGGTGCCTCAGGGTCAGCTCCAGGATGTCCGCCTTCTCCAGCTTCGAGGCGCGGG
CTGCGGGCGGGGCCGGTGAGGGCGGCGGGCCGCCCAGGAAGGCCGGGATTCCAGACT
CCCCAGTCTTCTCCCTACCCCCAACTCACCTCTTTCCTGAGGGCGTCCAGCAGGAGGCTCT R
GCAGCTGAGCCAGACTCTCGTTGATGCGGCGCTCGGCGCCGCTTCTCCATGACCGGCTTGGA
GGACTGTGGAGCCGGCAGCCACTGAGTCCTGCAGGCATCATCTCCCCTCTCCCCTTCGCGC
CCCCCCCCCCCCCCCCGCCCCGCTCCTGCCAACCCACGCCCGGCCAGGTCCCCACCTTCCG R
GTGCTCGGCCACGCTCCGGGGCTGGTCTGGGGTCCGGCTGGCGCCGGCCGCGCTCCCCGC
CGCGGCGAGGCCCTCGGCTTCCCGGGATGTCCGCAGGCATGGTGCGCCCCTTCGCCACCC

CCAGCCGAGGGCAGGCTGGGCGCGCGGTTTCCCAGGCACTTCTCCCGCGGGTCCCAGGCTC
AGCTACCAAGCGCGTGTCTGCAGCAGCCCGGCTATTTAAGGCAGCGCGGCTGCGGGGCGTG
GGAATCCCTCTCCGCGTTCTTTCCCACACTCGAGCCAGCCAATGAGCCGCCGGCGCCGGGC
AGCCCGCCCCCGGCCGCTGCCCCCGCCGGCTGTCAGTCACGAGTCAGCTCCCGGCCCACAG
ACCCCGCTGGCAACAAAGGCTAGCCGGGGCACCCCGCCCGCGCCTGCCTCGGACCACGCCG
GCCAGGCGGGAAAATCGCCGCGCCCCGGTCCCCAGTTCCGAGCGATGCGCCGGGAGGGGGC
CTCTCCGGGAGGGCGGAGGCGCGAGGCTCACCTTCAGGCCGAGCGGAGACCGCGAGAAGTC
TGAAAGGAAAATTCGCGAGGGGCCCTTATGCGCTCACGAAGAACCGGCGAGCCTCCGCCTT

CCGCGGATCCCGCGGGGGCCTTGGACCTCCGCGCAGCCTGCGCATCTGACCCTCGCCGCCA
GCAGCACCTGCACGATGCCGGGGACACAGTGAACATGGAACACCAGCCGCTGGACAGGAGA
GAAGCTGACTGGCCAAGGTCGTGAGGGAAGCAGGGTGGCATCACAGGGCCAAAGAAAGTAA
TGCCGCAGAGCAGATAGTGACGTCATCACAGGCAGGATGTTGTCATGGTATGGAATGTAAG
GATGTTACTGGTCAGGCTGGTGATGTCTCCAAGCAATCATAGGTGATATCTCAGGGTTAAG
GTAGATGATGACACAAGCCAGATGTAATGATGTATGGTCACTGGTGATGTCACTCTCTTCT
GGATTACCCAAAAGTGATGAGCCAAGCACCAGCCAAGAAAGTAGAACTCACAAAAAATGAA B
GGATAATTGTTACATTTCTGTTTGTTATTTCAAAGAAGCACGTGGAGGAAAGAGGGCTAAG
CTTATTTTCGTGTTTGATGTTGTTTTCACTTTGAATTCCCTTGTGGGGCACAATCATGTTT
TGAGTTTTGGGGATGCCAGCCCATGGTGGCCTGGGCAGTCTTGTCTGCATCCCACAAACCT

TABLE 1-continued

SEQID NO: 1

CTCTGGAGGCTCACTGTAGGCCTGACTGTTCTTGGGGCTGGGGAGGCCTCTCCTGAACTCT
GAACTGATGTGGGAGGAAAAGGCAAATGAGCAAAATAAATAATGACATGGTTTCCAGAGAC
AGAAAGAAATGTGTAGGTTTTGGGGGGAGCCGAAAGCCTTCTTTCCACTGAGTGGTCTGGA
TGGTATTTTTGCAGTGAGCTCTGCTGGAGAAGGCAATGGCAACCCACTCCAGTACACTCGC
CTGGAAAATCCCATGGATGGAGGAACCTGGTAGGCTGCAGTCCATGGGGTCATTGAGAGTT
GGACAAGACTGAGCGACTTCACTTTCACTTTTCACTTTCATCCATTGGAGAAGGAAATGGC
AACCCACTCCAGTGTTCTTGCCTGGAGAATCCTACGGACCGGGAACCTAGCAGGCGGCCA
TTTATGGAGTCGCACAGAGTCGGACATGACTGAATCGACTTAGCAGCAGCTAGTTGCAAGT
CCAGAGGAGGAAGTGGCATTCCCAGAATGGAAAGGAACCACAGGGCCAAGGGAGGAGGGGC
CGGGACAGGTGGGAACCAGGCTCTAGTGGCTTCAGGTCCCCAGAGGGGTCTAAGAGAGTCA
TGCTTGGCTTTTCTGAGCAGCAGAGTGGCCCAACTGGCAGCTCGGAAGGGCCACCTCCCAC B
ACTACATTCTACCTGGTGGGTGGCGATGCTGGCTGGCCCCCACCTCAATACCCTTTCCCAG

GGGTCCAGTCTGGGGCCCAGTGCAGACGCCTGTGATGCAGGTTTGATCACTGGGTGGGGA
AGACACCCTGCCCCCTCCCCGGAGGAGGAAATGGCAACCCACTCCAGTATTCTTGCCTGGG
AAATCTTATGGACAGCCTGGAGGGCTACAGCCAAAAGGGTCACAAAGAGTCAGACACAACT
GAGCAACTGAAGGAAGGACCCTCCTGTACCTGTTTCCTCACCTGTAAAATGGGCTACCTTT
TCATTTAGCCCTGGACTATAGTCCATGGGGTCGCAAAGAGTCGAACATGACTGAGCAACTA
ACACTTTCACACTTTGACTGAGAAGATAAATGAGATCTGATTTTGAAAGCACCCAGCACAT
GCAAGCGGGACAGAGTCACCTG [illegible] CCCACTGTATCCTCTACCC
TCTGAGACACCCTCTCCCTACCTGGGGTCTTCAGAAGCCTGTTTCTTGGCCTCTTCCAGCCC
CAACAAGGAGCCTTCTCTCACCCAGAGCAGAGTGAGTCCCAGGGGTGTCATCTACATCCCT
GTGTCCTTCCCACTGGGCTGCACCCCCACTCTCTCTCTGGGCCCTCCTACCTCTGGCTGTC
CCCTCCCTGCCTTTTACATCTGGATTTGATCTCTGGTAGGACCTGGGACTCCTGGGGACCG
TAGGGGCTCCCTTGCTCTGACTAGAGAGGGAGAGTCCTAGGCTGCAGGGGGGAAACTGTGC TGAGAAATAC [illegible] TCCAAAGATGGCTACAATACATCCACCCCAA
ATACTCTACCTGTGTGTCCTTGGTGAGATTTTGTGATGACATTAACCAGCAAAGACAGGGC
CAGTGGTGATCTATGAATTCTGAGGCTTGACTTGAAAAACGTGCACCTTGCTGTCCTGGGA
AACTCACTCCTGGAAACCACTGACCCCTCTGTGAGGAAACCCGAACTGGTCTCATGGAAAG
GCCTCATGGAGAGGCCTTGTATAAGTGTTGAGCTAGGAACCTAGAAATCTCAGCTTCCAGA
CAGGTGATCCCAACCTGCCGCTTCAGAGCCCCCACTCACACTTTCCCAGCCAGCTCTGTGT
GCTCTGTTCCACTCTTGATTCACATGACTGGTGTTACTGTGACACTTTGGGGTCATTCCTT
ACGAAACAATAGTAACTGGAACAGCTAAGATGGCCCAAGCCCTGGACCCACCCCCCTCCCC
AGCCCCACCCCCCAAACCTTGTTCCTTCCTTTCTCTGGCATTCACAGAGTCACAGGAGCTT
CCCGCACTGGCTGTCCATCTGACGAGGTGACTTTTGCAGCTATCCAAGGCCAACTATCTGT
CCTCCTAGATCCAGGCTTGAGTTGGCCAAGTCCCAGTAGGCTGATGGTCCCAGGGGCATCT CTAGGGACCACTGTTGGCCACTGGGCAGGAAAAGTAGTGGGGGACTCTGTGTGGGAAGATA
AGTGTATTTTCCAGTCCAGACACTGGGCTGCAGCCTTGGTGGGGGTGGGGGATGGTCTT
TCTCACGTCTGGCTCCCATGACAGCATTCCACAACATTCAGACAGTGTCCCTCCGGGGCCT
GCCAGGTGCTGTCTGTGCACAGGCCCCTCCCAACCTCTGACAGGCGGGTGGCACCTGCACT
TGCACCCTGCCCCTCAGCATTCCACAGGCACATGGGTCCCTGAATATCAGAGACACCATAG
ACCATGACCAGCAACCCCATCCTCCTGTTCCCTCCTCTTCTGCCAAGGGACAACAGGCTGT
GGACTCAGGCAGCCAGGACCAGAGTTGCCATGTGACCAGGCTAGAGTCATTGCAGGGTCTC
TCCTGGAGCATGGGACTTGGGTCCTGAGATGATAAAGTGGCAGAGGCTAGGGCTGGAGGAA CCCAGGATTCAGTATAGAGAAGAAGGAACCAGATGACCAGGACCCTAATCTTAACCCTGAG
GGGGCATCTTTCATTTTTACAGGCCAGCGGACCAAGACACCTTCCTTCGGCTCTTCGTGCT
GGGCAGTTGGAGCATCCCCCCAACACCTGATGCATGACAGCACCTCCCCCGAGGTCTGGGC
ATTGTCAACATCTTTCTCCATTATTGAATGTTGACACCTCTCCACGCTGGGGAAGCCATGT
CTCCCCAATTCTGTGTGGTAACAGAGCTTCCCACCCTGTCTGCCTGTGATGCCACCTCCCT
GTGGGCTTCCATGGGTGCTTCTCTCTCCAGTCTCCTTGGACCACTACTCTCTGGAGAGGTA
TGCTTTGCTCTCCTGCTGGTCACATCCAGACTAGTTTCTTCTTCACCAAAAAAAGTCCCAG CTTTGAACCTCATCTTATTAACAGATCTCATCTTGTGAAGTCCACTGCAACCCTGCGGGGC
GGGGGCCTCCCCATACCTTCTGAAGGTTCACTCCTGATTCCCTGTCACTTTCTCCAGCGGC
TCCTGTCACAGTCCTTGTTGACTTCCAAATTCACACGGTTGATCTTCTGGACTTCCTGGCC
TCCATGGGGCATCCTAGTGTAGAGTTGGCAACTAAGCTTCCAATCCTAAGTGCTGGGTGTA
GACTGTAGCCCTAATATTCCCATCCACCCTGCAGGACACGCCCACCAGGAAGCCCCGCCCA
CAGGCCACAGGTCAGCATCTCCAGTACAATATCCTGCTGCTTTCCCAGTGTAACCTGGGGT
CCTGCCTCCTCCCTCCACACTCTCAGCCTCTTGTCTCAGGTTCTGCCTCCCGCTTCTCCTT
GTGCCTTTCAGTCCTGTGGAACTTGGGGAACAAGTCTTCACTCTAATCTTTCTATCCACAC AACTGGAGCACTCTCTGCCCAGTGGTGGAGCCTGACTGAGGCACCAGCCTCCTCTGAATCT
GACTATTCTCAGTTCTCAGACCAGATTCTGCCATCGTCCTCGACCCTCAGAGTTCACTCCC
AGTGCTGCTCTGGCAGGTCCTACAGTGGCTCTATCTCCCTGATGTATACAAACACCTACTT
CTGACCTATTGCTTTTCCACCACTGGCTGCAAGCCGCCACCAGCTTCGGCCTGGAATTTG
TAGTTCTTTGCCATGGCAAGGCAGCCAGTCTTGGAGCCGAGTGCTCAATGGGGGCAGGTGG
ACAGGAGAGGAGATTAGAGGGTCAGCAGACTGGTCAGAAGAACAAGCCTAAGCTCCTATCT
TCTCTCGGAAGCTTATGGGAAGCCATGGCAGAGAAGGTTGTGTGTAGATCACTCTGGCCCT
TGGCTCCACCACAGATTATGGGGTCAGGATAGAAGCACAGCCCACTCGGCTGTATCCATAGC AGCCTCAGTGGACGAGGGGCATAGATATAAGTGAGGTCATGGATATTCTTGGGAGTTTTT
TGTTGTTGCTACTGCTGTTAGATGGCTGAAGCGCTTAAAAATAAAACCAAGTGTATTAAAC
GATATAGATACTGTTTTAAAAGTTTTAGGAAGTTTAAGTTAGTTTGTAAATGAAACCAAAT
ATTAACCAAAGACCCCTTTATAAGTAGCCATTGTAACTTCATAAATAGGATATTCAGGTTT
TTGTCTAGAACATATGTATTTTGTGATCATGTTGTTAGGTGCATACAAATTAAAATAATT
TCATTTTTATCAGTGAGCTCAACCTTTTATTGTTATGCAACCTTCTGTATCTAGTAATGCTT
TGACTATAAGGTTTCTTTGTTAATCTGTTAGTGAAACTGTTAATACGGTCACATCTGCTTC
CCTTTAGTTAACATTACGCAGTAGGTTTCTTTTCTCCTTTTACTTTCAGTTTCCTGTACCT TABLE 1-continued

| SEQID NO: 1 |
| --- |
| TTATATTTCATATTATTTATGTCTTCTGTAACCTGTGTAAAATCAGATTATTTTTAATCAG<br>GCTGACAATCCTGGTCATTTAGTCCCCCTGGATTTCAGACCTCTGCTCTTTAGAACTGTGA<br>GGGAATACATTTCTGTTGTTTTAAGCCACCCAGTTTGTGGTGGCTTAAAAGCCTCCAAGAC<br>ACAGAGACATGCTTCCAGGGCTATCGTTTTGCCTGCCGAAAGCCTTTGCATCTAGTTCCTC<br>TTGTCCAAAGCAGGTGATATTCAATAAAGTAATAAAAGAAAATAAAGGTTCTATTACTATA<br>TATACCATATTTTTGTTATCTTTTTAAAATTTTTTATTACTTAAAATTTTTTTGAATTGTT<br>GTTTCATTCCCTTATCTTTGTGCCATATTTAATAATGGTCACCTAGGGACTTTCCTGGTGC<br>TCCAGTGGTTAAGACTTAGTGCTTCCAATGCAAGGGGCATGGGTTTGACCCCTAATCAGGC |
| AACTAAGATCCTGCTGGCTGCATGCCATGCCCGAAAAAAACAAAACAAAACAAAACAAAA<br>ACAGAATCAAAATAATGGTTTTTTGAAGAAGACAGGGATTTTCACATTCTGTAATATTTGT<br>TTTGTTTGTGGCTTTCTTTTTATAATACTAATATTATTTATGCAAGGAATGAGTCAAGTTA<br>GAAATTTAGAATAATATAAACAATATTTAAACTGTTTTATGGATGTTAACAACTTTGGTGC<br>CTTATGATTATTTGGGGGAATTGATaTAATGATTAATTCATATGAAAACAATTTGGTTTT<br>CCCCATTCCTTTTATTTATTTAAAATTTGTTTATTTAGTTTAAAATTTATTTTTAAAATAT<br>TTAATTATTTTTAGGTATTTATTTTTATTTTTATTTATTTATTTTGGCTCCATCTTGTGGGA<br>TCTTAGTTTCCCAACCAGGGATGGAACCTGTGCTCCTGAAGTGAAAGTATGAAGTCCTAAC |
| CACTGGACTGCCAGGGAATTCCCTAAGTATTTATTTTTATTTTTAGCTAACATATGCCTGA<br>GATGTGCTGTTTGTAATACTAAAAATGTGGAACAACCAATATTTATTTAAAAATATGAGA<br>CTGGTTAACTAAATTACACTTTATTCTATAATGGACTTTGTTGCTATGGGCAACAAATGCA<br>CATATGCAGCCATTAAAACAACTTGCATAAAAATATGAGGCTTACAAATAGCTGAGAAAA<br>GAAGAGAAGCTAAAGGCAAAGGAGAAAAGGAAAGATATACCCATCTGAATGCAGAGTTCCA<br>GCGACTATCAAGGAGAGATAAGAAAGCCTTCCTCAGTGATCAATGCAAAGAAAACAATAGA<br>ATAAGAAAGACTAGACATCTCTTCAAGAAAATTAGACATATCAAGGGAATATGTCATGCAA<br>AGATGGGCACAATAAAGGGCAGAAATGGTATGGATCTAACAGAAGCACCAAAAGAGGTGGC |
| AAGAATACAGAGAAGAACTATATAAAAAAGATCTTCATGACCCAGATAACCACGATGATGG<br>TGTGATCACTCACTTAGAGCCAGAGATCCTGGAATGCAAAGTCAAGTGGGCCTTAGGAAGC<br>ATCACTATGAACAAAGCTAGTGTAGGCGATGGAATTCCACTTCACCTATTTCAAATCCTAA<br>GACATGATGCTGTGAAAGTGCTGCACTCAATATGCCAGCAAATTTGGAAAACTCAGTAGTG<br>GCCACAAAACTGGAAAAGGTCAGTTTTCATTCCAATCCCAAAGAAAGGCAATGCCAAAGAA<br>CGCTCAAACTACCACACATTTGCACTCATTTTCTCACACACTAGCAAAGGAATGGTCAAAA<br>TTCTCCAAGCCAGGCATCTACAGTACAGGAATCAAGAACTTCCAGATGTTCCAGGAGTTGG<br>TGATGGACAGGGAGGCCTGGCGTGGTGCAGTCTTTGAGTCATGGGGTCTCAAAGAGTCCAA |
| CACGACTGAGCGACTGAACTGAACTGTGAATGAAGCAGGGTACAAAATGTTGAGAGTAGCA<br>GGAGGATTTTTTTTTTCAATTTTCTTTTTTATTGAGGTGAACCTCATGTAACATAAACTTA<br>ACCATTTTATAGTATATAATCCAGTGGCATTTAGTATATTTAGTCCAACCATCACCTCTAT<br>CTAGTTATGAAACATTTTTATTATTCCCAAAGGAGGCCTTAGCTCCATGAAGTGTCTCTCC<br>TCATGCCTCCTCCCGGCAGCTCTTGGCAATTACTAAGGTATTTTCAGTCTCTATGGACTTG<br>CCTCTTGTGGACATTTCATATCAGTCGAATCACATGCTTTGTGTCCTGTGTCTGTTATTTG<br>TCACTGACCTCCATTCACACCGCAGCCTGTGTCAGTGCTCCATCCTTGGTTATGCCTGAGG<br>AGCATTCTACTATAAGGAGGCACCACACTTTGTGCCTCCAGCTGCTGATGGGTTTGGTTCC |
| ACCCCCATTTCAACCATTCTATGACTAGAGCTGCTGTTAACATTTGGGTGTGAGCATTTG<br>TTTGAACACCTGTTGTCAGTTCTGTGGGCATACCCTAGTTGTGGAATTGCTGGGTCATATG<br>AAAATTCTATTTAACCTTTTGAGGAATGACTAGACTGTTTTCCGCAGTGGCTACATCATTT<br>CACAATCCCATCAGCAATGTATGAAGATTCCATTTTTTTGACATCTTCACCAACACTTATT<br>ATTCACTTTTTAATTATTATTATATTCATGCTAGGGGTGTGACACAGTACATCTGGTTTT<br>GATTTGCATTTCCCTGGTTCCCATCATTTCCAAAGATGTTGAACATCTTTTCATGTGGCTC<br>TTGGCCATTTATGTATTTTCTATTTTAAAATGTCTATTTAAGTCATTTGCCCAACTTTTAA<br>TTGAGTTGCTTATCTTTTAGTTGTTAAGTTGTAAAAGTTCCTTATATGTTGCAGATACTAC |
| ACTCTTATCTGACACATGGATTGCAAATATTTTCCCCCATTTGTGTAGTATTTTCACTTT<br>CTCAAGACTGTCCATGAGTTCATTTTTATAGAAAAGATACATTCTTTTTCATTAAAACAAT<br>CTGAACATATATTGTCATAAACACAAAGTGATTATCTCTGAATAGATTGTCAATGTTTTGT<br>TATTTTGGAATTAACCCTGGCAATATTTTTCAAGGTTAGTAATTTCACAAATTGGTAAATG<br>GAAAGTGAAAGTTTCTAATTCTTAGCTCATGTTATTATGATGTGTGTGCATCTTGGAAAGG<br>ACCCAAGGTGTGGAACATGCAGGGATTTCTGAACACTCAATCCTAGAGGTGGCAGTGCTAT<br>CACAGTCCCAGACCCAGCTGGTCAGGTGGAAAGCCCCCTGCCCAGCCCACCTCAGTTCCT |
| CGGGTCATCATCATCGGCATTGTTTTGTTTCTGTTTCTCACTCTGGGGCTGTCCTGGGAAA<br>AGGAAACCGAAACTGAAGCTGAATTAGCCTATGTAACTCTGACGTGGTTTGCTCAGGCTAT<br>TAAAGGGCTGAGCTGCCAGGGCTGAAGAGAGCCGAGAGCAGAGAGGCAGCCGCAGCCAACC<br>AGTGTCTGCAGAGAGCCTGGCACCAGAACCCACGGCCATGGTGAGTGGTGAGGCCGGTTTG |
| ACAGGTGGGGCTCTGTATTCCCCTGCCTGGTGGCATCTCCCAGGGAAGAATGCCTACTAT<br>GCACAGGCAGGTAGAGCTACTCAAAGCATCCGGTTCCCTAAGTGTGAGGGAGGCACAGCG<br>CTCTTTCTAAAATCAGGTCTGGGTCCTGAAAGTGGCTTCTGCCCAGCCGCCAACTCTGA<br>GATCCCTTGGGATCAGCACAGGCAGGGGGTATTTTATTGGAGAGTTGACATGAAGATTG<br>TGGCTAGTAGCTCTTCTGCTCCCTTGCACTCTCCAGTGCCTGGGGTCCCCATCTCCGTGGG<br>TGGCAAGGGTGGAGAGGAGGGAGCTGCATCCCCGGGGTCTGACACTCGTCCCACTGCCAGT |
| GCTACACGTGCAGTAGTCCCAGCACTTCTGAATCTGTGTGATGCCCACAGGCGGGGACCT<br>GACGGTGAAGATGCTAGGGGGCCAGGAGATCCTGGTGCCTCTGAGGGACTCCATGACGGTA<br>TCCGAGCTGAAGCAGTTCATCGCCCAGAAGATCAATGTGCCTGCTTTCCAGCAGCGCCTGG<br>CCCACCTTGACAGCAGGGAGGTGCTGCAGGAAGGGGTGCCCCTTGTCCTCCAGGGCCTGAG G<br>AGCTGGCAGCACCGTCCTGCTGGTGGTCCAGAACTGCATCTCCATCCTGGTGAGGAACGAC<br>AAGGGTCGCAGCAGCCCCTATGAGGTCCAGCTGAAGCAGACTGTGGCTGAGCTCAAGCAGC<br>AGGTGTGCCAAAAGGAGCGTGTACAAGCGGACCAGTTCTGGCTGTCTTTTGAAGGGAGGCC<br>CATGGATGATGAGCACCCGCTGGAGGAATACGGCCTCATGAAGGGGTGCACCGTGTTCATG<br>AATCTACGTCTTCGGGGTGGCGTAGGGGAAGGCCCAGGAGGGCCTTAGGGAGGCTCCCCATG |

TABLE 1-continued

SEQID NO: 1

CAGCGCAGTGAATAAAGTTGTAGCAAAGCCAAATGTGAAGTGTTCATTCCACCCTGGCCAG
CACCCCATGTCATCAGCCCTCCATTCGGCACCCTTCTGGTGAGATTGGGGAAGGGTGGAG
GAGGGACTGGGTGAGGGGACTCAGGGTCACTGAGTGGTCACCAGGCTAGGGTGGCCAAGTT
AAGGGACAAACCCTGTGGGATCAAAATGGTGACCCTCTGGAGAAACTGAAGATGTGTCCCC
ACCTCTTTGGGAAATTAACTTCTAGAGAAATAAAAAGAGGCAGGTCTGTTGAAGCCCATCC
CTGTCTTCCGGTTGAGCCTCAGTCAGCCCTGCACAACTGGTCTCCACCTTCACAGCTGGGT

CAGCAGATAGCAGAGGGAGGGAAAAGGCCTGGCTGGGTCCCAAAGCCCACACAGTGACTGT
CCCTGGAACCGGTGAGGGGCTGAGTCCCTAGGGCCTGCCTTGGCCAGTGGTAAGGGAGGTT
CCCCCACACCAGCTGGAGGCTGAGGGCCTCCAGGACCCATCAGAATACACTGTCCAGCCTT
CATTGGTCTGGAGGGAATTGGGGACTGGGCCTTGGGCACACACATCACCATTAGGGTGACC
TGCTCCTTCAGAGTTCACATCATGGAAGGGCCATAGCCAGCAGGTGAGGGGGCACCCAGGA
TGGGGGTTCCTGTTGTTCACATCGATGGGAGGGGAACAAACTACACCTGCTTCCACACTAG

ATGCTTCTTTCTGTGCCAGTTTCCCAAGTGAGTCAGCCTTGGACAGAATGCGGTGGGCAGG
GAGGGGGACACAGAACCTATACCTCTTGGGCCAAAGTCCATGACTCTGGGGACACTCAGAT
CTCAGCTTTCGGACTCTTCAGGGGCATTTGGCTGGAGACCCAGACCCCTTCTTTCTGATCT
GTGGGAGTTTGCATCTGAGCTGGGGCACCCCCAGGTCTTGGCTTGCCTGTGACACTTATGTA
GACACGCAGGTGTGTGTGTGTGTGTGTGTGTGTGTGTGTGTGTGTGTGTAGGGGACTCCT
GGCTCTAGCCTCATTTCCTGGGCCCCCACCCTCACCTCTTTGTCATACTGTAACTTAACAA
GTGTGAGCACGCCCTCTCGGTGACACCCTCCTTTCTTGAATCCCCTCAGCAGGGTCTGGGC
GAGGTAGGGTCCTTCTCCAAGATGCCTCTGGGCTGCTCACCCTTCATGGCCTCTGGCTCAG

AGATCTGTGGTTGGCTTGGATGAGGGGTGTGCAGCAGACTCAGCCCTGGAGGAACAGAAG
GGATCTCCTCTCCTCCCATTCCCACCATCTTCAGCTAAGTCGGGCTCTAATTTGCACACTG
TGGATCTCAGTTTACCCCCTGGACCCAGCGGGAATGGTTGGAGAACTAGCGGGAATGGTTG
GAGAAGAGCTTGGGGGAGCTGGGAAGGGGGCGTGGCTGGCCGTCCATCGCTGCTGCTATT
CCCACCTCAGTCAACAGGGGGAGCCCGCAGCCCTGCAGAGGGCCGGGAGCCCACCCGGGAT
CGCGAGGTGGGCGGGGCTGCGCTTCGCTGCGACCAATCGCCGCAGCTCCCAGCCCGCATTG
GTCCCCGGTGGCCGGTGGTCCCGGGCGGCCGAGCTTCCCGTCCCCAGTTCCTGTGAGGGCT
AGGATCCCCCGGTCAGGTTCCTCTCGCCCGGGGAGGGGCCCAGCCCTTTAGGGCCGAGGGG

CCGCAGGGCCTCGGATCTGGCAGCCCCTTCTTGCGGCCAGGGAGCCCCCGCCGCCCCAGCC
CTGGCCCAGCCTGGAGCCCCTTGGAAGTCCCGTCACGTCGTCTCCAGATTATGCATTAACC
CGATTTCAGCCGCATTTCCTGGCGGGCGGCGGGGCTGGAACGTCCCGCGCGAACGGCGG
AGGGGCGTCCCTGGGACTGCGCCACACCAGGGAGAGCACCCTCGAGCCCGCCCCAACCCCG
CCCCTCGGCCTGGCCAGGCCCACCACCCACCTTGGCCAAACCTAGACCGGCCCCCTCCCTC
CCCCAGCCAGGCCTCCGCCCGGCGCCGCTTTCCCGGCGCTTTGTTCGCGGCTGCCGCGGT
CGCAGGACGCCGGGAGGGCCGGGGCGGGCGGGCCGGGGGGTGGGGGTGGGGCTGGAA
GGGGGTGGTGCTGCCCCAAGGCCCGCCCCCGCACCGCCCGCGCTCCCGCCACCTCCCCCGA

CTGCGTCCCGTCCTGTCCAGTCCAGTCCCCGGCGCGGCCCGGTCCGTGCGCTTGCTCCGGG
CCGCCTTCCGCCGTCCTCTGCCCGCGCCATGGCCAGCTTTCGGCCGTTCAGCCGGGCCCTG
CTGCAGCCTTTGCTGCTGCTCCTGGTGGTGGCCGTGCGCGCCCTGCCCAGCGCCGACGGGA Y
CGTGCCCCGAACGCGCGCTGGAGCGGCGCGAGGAGGAGGCGAACGTGGTGCTCACCGGCAC
CGTGGAGGAGATCCTCAACGTGGACCCGGTGCAGCACACATACTCGTGCAAGGTGGGCCCC
CTGGGGACCCCCGGGACCCTGAGCCCCTTCAGACCCTTCTAGAAGCCCTGGTTGGGGGCCC
TTCCCCCGCGATCCCGGACCCCTAGCCCGGAGGTCTTCCCCGTCGCGATGCCGGCCGCGCGC

TGAGACCCCCGTCCCGGGACGTGGGAACGAGCCCCAGACGTTCCGCAGCACCAGCTCCGGC
TCCTGCTCCCTTAGCGACCGCCGACCCCCGGTGGAGGGTGGGGGCGGGTGCGGTCTG
AGAAAACTCGCCGAGCGCCGGAGGGAAACTTCCTGCGGTGCCGCTGCAGTCGCGCTCGCGCT
GCCCGGCCCTGGAGACCCGATAGTGTCTGCTCCTTCACCCCAAACCCACTCCCTTACTGG
AAACAAGTGCCGCCCCCGCTCCCCGGAGAATGTTCGGCTACCGCGCCGCCATCCCCACCGGCCA
AAGGAAAGGGGACGAGGGGAGGTGACGCTTTCTGCTTGGGATGGAGCTGGTGATTTGGCCT
GTGGTCAGTGCTGTCGCCCTCTCCCCAGAGGTGAGAATGGGTGGTCCGGAGAGAGAGGAGG
GGTCCACACCTAATCTCCCAACCGCCGGGGCTCCTGCTGGGCCTTGCTGCAGTGATGGCTGT

GGGCCCAGAGCAGAGAAGTGGGCGGGGCCGTTGCTGAGCCTCAAGTGCGGGGGTGCAGGG
CAGGTGCCCCATCCGCTCCTGGGACAGCTGTATCTCCCCTGGCCTTAGGCAGAGGGCCTT
GCCTGGCCTCTCCTTCAGTTGAATCTGGGAGCTCCCGGGGTAGGTCTGGTGGTTTTTTCC
CACAATCTGTTCCTAGGGAGGACTGAAGGGACCCAGGCCCCTGCCCCTCTCTGGCCCCTAA
AACCACCTCCCTGACCAGAAATCGGATCATTCCTCTTCCTTGGAGATGGGGAGGGGTGGCA
GCTCCTTTCAGACTGGCCTGTCCTGACTACAGCTGGGATCCCCCGCCAGGCCCCCTCCCCT
CCACCACAGCCAGGGCACTTTGCCAAGTCCCTGCAGGATTTTCCGACTTCCTCCCCGCTG
CTCCTGGGTGTGGCTGGGGTGGGGGAGGCCGATGAAAGCCGCCCAGCTCTCCCCTGCTGGT

TATTGGCCTTCCAGAGCCTACTCTGTATCTAGGCATGGGGGCGGGGAAGAGCTGCCAGC
CCCACCATCCCTGGGCCACTGGAGGGTGGAGGGAGTCCCCTCTAGATTTTGCAGACCCAAGG
CTCCCAGCAGGGGTGGCCAGGTGGACGGGCCACTCTTGTCTTTCACTCCTCTTTCCAGAAG
TCCCGGCCCCCATAGATCCTGAAGAAAGGGGTGTTTTTTCTCAGGGACAGCATTCCCGGGC
AGTCCCCATGGGCCTATTCCTTTAGGGCAGCTCATTCTGCCTGCAGTGCCTGTGGCCCTCC
TGCCCCCACTGCCAGTAGTCTGTGGGCACCCCCAGGGCTTGGTTTGTCTGAGCAGGTGCCC
TCAGGGCCCCAAGAGCAGAGTGTGGAGGGTGGGGCTGCCCTGTGCTGCCCAAACTTGATTT
TGTGGTTCACAGGCTGCCTTGGCAGCACTCACTGTAGGAGCCTTGCAGGAGGAGGGGTCTT

TCACCTCCTGGCTGGACCCGTGTCTTAGCCCACCCACAGGGCTGCATGGAGCCAAGCTGGAC
AGGAGCCTTGAGCTCAGAGCCCGTCACCTTGAAACTTCATCATCCATGTTAGTTGCTTCCTG
ACTCTTTCCAGAGGTGGGCCCAAGTACTGGGTGGGTTGACAGGGAGAGTAAGGTGTGGAAG
GCTGTGAGGTGTGACATTTAGAACTGGGGTGGCTGGGGTCATCTAAACCTGAGGGTTAGGG
AGCTGCTTCTTGAGGGAAGGGGTGTGTTCTCAGGCCAGGTATCCTGGAGTATAACAAGGGC
AGTGGCGTCTGTCATGTGTGTGTGCTTCCCTGCAGCTTCCTCCTGGGGGTTGGGGCACTG
ACTCCACATATCTGCCCAGGGTTTGGGTATACTCCGGACATCTGGCCTGAGCAAATGAGGT
GGGAAAAGAAGGAAAAGTCCAGGCACCAGTCTGGTGTCTGCCCTCTGGCCTCTGTGGCCATC

TABLE 1-continued

SEQID NO: 1

TCCCCCGCTCCACCCAGTTAGAAGAGAACCGCCGACAATTGAACACCCCCTCATGTCCACC
CTAGGTTCGGGTCTGGCGGTACCTGAAGGGCAAAGATGTGGTGGCCCAGGAAAGCCTGCTG
GACGGAGGCAACAAAGTGGTGATTGGCGGCTTCGGAGACCCCCTCATCTGTGACAACCAGG Y
TGTCCACTGGAGACACCAGGATCTTCTTTGTGAACCCTGCCCCGCCATACCTGTGGCCCGC
CCACAAGAATGAGCTGATGCTAAACTCCAGCCTCATGCGCATCACCCTGCGGAACCTGGAG
GAGGTCGAGCACTGTGTGGAAGGTGTGTGTGGGGCCGAGCAGAGCAGGTGCCTTGGGGCCA
GAAGGGAGCTTGTCCTAGCCTAGGCACATGGCATCTTGTGGTCCCACCTCCTTTTCTGGC
TCCTGGCTCCCTGCTTTCCTGGCCACCTCAGCTCCAGACTCTTAACATAAGCAGCACTCCC
CACCCTGGCCCTAGTGTTGCCACTATCTGTCATCTTGGACTCTCAGACCTGCAAAGGGATA
GGCTTCCCATTCTTCCCTCCGCCTCCCCAGCTCTGCACGCCCCTTCCTGGAGTTCCCTGTT
CTAGGAAAGAGGCTGGAACCAGGTGAACGAACACCAGTTGTTTGTGTTCTGCAGAAGCCCG
AACACATGTCTAGACCGGGCCCAGATGTTGACCCTTTCGGGTCGGGCTTAAAGATTGTCCT
GGAGGCGAGGCTACCCTGTTATGTGTTCCCAGAGGCCTGCCATTTCTGGGAAGGGACAGTT
ATGTGGAGTGAGCTGCTTCTAGGAGTTTGAGCGGTTGTGGGATCCCCTGACAGAGGTGGAG
CATCTTTCCTTGTCTGCTGTCCCCATGTGTCTATTCTGAATGGCTCAAGAGCAACCCTCCC
TCACATGATGGCCTCACCCATCCCCTTCACCCCAGGAGAATCCCAGTTGGGGCTGAGATCC
TTGGCTGAGGAATGTAGCAGGCAGAACTAGGAACTGCCTGTCCCCCTCACATCCTGTCTGT
CCCCTCATGGCTGCCTGGGGACGGATGTATGCGAGGACGTGGAGAGATTGCTTCCTCCCAG
GGCAGCAGGAAGGGTCCCTGACTTCCTGTCCTGGGAAGGCGACCCTGTCCCTGTGACTTGC
TCTGTTGGCCGGTAGGGAAGTTCCATCTTCTACCCAACTTAACTCCTGTGGTGCTGGCTTG
CTTTTGTGGGATCCTGGATGGTGGACTCATCTGGCCTGGGGCAGACTGTGTGTGTGTGTGG
CGAGGTGTGGAACCTGAAGTGGAGAGCCCTGTAGCATCCTGCTCGGCCCTGCAGTCATTTGC
TCCTGGGATTGCATCTATGGTCCTGATGCAACATCGGCACAGAGATGCCAGCAGGCTGTGT
CCCTGGTCCCTTCCCAGCACTAGCATAGCTGAGGGGTCCCAGCATAGCCCTCCCACCAGGT
GAGGACTGGAGACCCTGACTGTGCTTTGGAAGCTTTACTCTAGGGGAAATATGGGAGAGTG
GCATGGAGAGGAGCCAGGTTGTAGGGTGTGATCCCCAGTTTTGGAGGATGAGTTGGAGACT
AATGAGAGGTGGGAAGAGGGGTCAGGCTGCAGAAAATCTGTTTCTGCAAGATCAAGAAGAC
AAGTCATTAACTCCATAGCTGGAAGGGTCTAGTTCGAGGGTCTGTGGGGTCAGAGGGCATG
TGGCAGGGGGGCCACCCTAGGCAGAAGAGGGTCTGCCATCTTGCCAGGTCCTATTCTACCC
AGGCCAGGCCCTGGCTCTGGATATGTCAGCCTGGGCACAGGACCCCTGGAAAGGAGGGTCT
GCAGAGAGAGCCCCCAGTGAGACTTCATCTGCTGTCTGCTGGCTACCCGGGATAGGGACCA
GTCTAGGCCCCCAGCTCCAGCTGGCCACTGTGGCATGGTGGTGGAGGGCAGGCCCCCAG
GGAGGGAGGGACCCAGAATGAGAAGCTTGGGGTCCACTGTAAGGCTCTGGGGAGCCCTGGA
AGTTTTGAGCCAGTGACACCGGATCCCTTCTTTGGAAGGAAAGCAGTGCCATAAGGGCAGG
GGGCCAGGGAGAGGGTAGATTAGATGGGGTGCCTCCCCTCTAAGGATCCCCAAAGCCTGAA
GACAAGGCTCCCAGGAGTTGGTGCCAGGCTTGAGGAACACACAGCCCTCTTCCCACCTCCC
ACAGCAGGGACCAGGCAGGACAAGGGCCTGCCTCCCATTCTGTAAGGCATACCTCCCATTC
TGTAAGAGATAAAGACCTCTGACCCCACCCCAGGCTCTCCAGGAGCCAAGCCTCACCTTA
GCATGGGGGTAGGGTTAGGGATGGGCCGAGCTTGAGCTACAATGACCTCTCATCTGACCC
TGACCCTTTTCTCTTCCTTGGGGCCCCATAGCTGCCCCCGTCCCTCAGGGCCCCGAGTGAA
GGCTGTGAAGCTACTGATTGTGGAGGTCACCCCAAGACCTGTGTCTCTATCACAAATGTCC
CCTGCCCCTAAAGGCCCACAGGAGCCAAGGTCAGGGACACATCCTGGAGGCCCACCCC
CTAGATGCCCCACCTCATCCCACCTGGACCCTGCTTCCTGCAGGGGTACCTGTTGCTGG
GAGGCATACCTGGTCCCAGCTCCACTGGGCTCGCCTTCCTCAGTTTCTCCCTTAGGCCCT
GCAGGCTCTTCCTGGCTCTGGCCCCTTCCCCAACCTCCAGTCCCCAGGAAGCTCCTCCCC
AATCCTCTGCCTGGGGAGCCACATTCCGAGCATAACTGAGACAGGTATGTGTCCCTCCCTC
TGCACCACTTGTGGGTGAAGGAGACTGCGGGTTTGCTCCAGGAAGGAAGGAGACCCTCACG
CCCTGCTTTGTCAGGGAAGTGGCCTGGCCTCTTCCAGTGCCAGCTGCCCACGCATCATGAG
CTGGCCAGGCTGGCACCTGAGCGGGCATCTCTTCCAGCCTTTGGCCACTATACCCTGGTCT
GGACTTGTACACTTGTACACTCCACCACCCTCCTCTCCCCACCTAATAAACACTGGTCC
TTGGGCCCCCCTGAATTCCCTAGGAGGGATGCAGGCTTGGGTCCTTCCCCAGGCCTTTCC
CTCCCGAACTCCGAGCCAAGAGCAGACAAAGGAAGTGTTGTCTGCCCTCTCCGGGCCTGGC
ACAGGAACAGGGTCGGAGAGTCTGGCATTAGTCCAGCCCAGCCCTGCCCAGTCCTGAAGCC
GGCGGTCCTGGTGGCCACAGCCTAGACTGGCCTGCCTGATTCCAGTGAGCACCCTCCCTTC
CTCCCTGCCCACGGCTAGCCTTTGGGCCCTTCACGCCAGTCTTGGGCCTTTGGGGAAGGTAGTC
CTAGGCTATATCTCAGGCTAGAGAGATGCTGGGTCCCGGGCCCCGGCCTTGGCCTTGCTG
GAGGCCCTGTCGCCTGGAGCCGGATGTGGACACAGACACCCCCAGACAGGGACTGGCTCC
GCAGAGCAAAGCGGGGCAGGTAGGAGCCCAGGGCAGGTTCCAGGGCTGGCTTCCTCAGGGC
TAGAGCTGGCTCCCTCTGCTGTCTGGCATTTAGCTTCTGTACCCCCAAGTCCTGAGCCTGC
CCTACTCCCCCACATTCCTCCCTGCCGAGGGGGGAGGTGCCTTCTTCCTGTCCCTGTTTCC
CTCTTCCAGACGTAAGTTCTCACCCCACCCCCTCCAGACCCGCCCCAGTGCCGTCCTCAGC
CCCTCCCCCAGGCAGGTCCTTGGAGCTGGGGCAGCCCCAGGCTGGAGGCTCCGGCCCTGGG
CTTTCTCCTTCCTTCCAGCCACTGGGGCGGGGCATCTGCTCAGGTGGACCGTGGCCTGCT
CCTGCACTGTCCTCTCTCACCTAGGGTCCCCCGTAGGAAGTCTCCGACAGCATGGCTTGT
GGGACCACAGCGGGCTGGCTGATACCCTCACTGGGGCGGCCCCAGGAGCTTGGGCGTGGT
GGGGGCTGGGCAGGGGTTGCTGCTGAAATCAAAGGGCATTGGATCCATCACTTCAAGGCA
GTGCGCTCCTTTCCCGCAGGCCTGAGCTGGTGGAAACAGCTCCTGACTTTTTCCAGACCCC
ACCCCATCACCCTGCTCCCCACCCAGAGAAGAGCCCCCCGCCTCCATACTCCCCAGCAGATT
GGAAATGCAAAAAAAAAAAAGTTGTTTTGAAACTCTCCTCTCCCCTGCTGTCTGTACCTGC
CTTCCGCAGGGCTCTGGACAGAGTAGATTCCAGTGGGGCCTGCCTGTGGAAGGAAGGCAGA
GCCATGGAGGTGCTCGCAGCCTCTCTTGGGTGCTGGGAAGAACTGGATCGCCTGGTCAGGG
CTAGCTGGTCTGGATCTGGGCCTCTAGCCCCCTGCCCCACCAATCCTTTCAGACTGAGGTA
GGGAGAGTGCCAGAGGCTGGGATGGGGCTGCCCCTAGGTAAGGTTAGCAGGGGCGTGAGCCCA
GACTTTCAGGGTTGTAGATCTAGCCAACTGTTGCTTGCCCTGCACAGCCTCCTCCAGCCTGT
TTTGCTTCCTTCTTAAAGGTTAATCCCCCAATCCCCTGAGAATCAAAGCCTGCTCCCACC
CCATCACCACAGTGGGGTGGAAGACAGCTGCTGAAATTGACCTCTCTCCTGCCCCTGCCC
CCAAGTCCTTTGCCTTCACCAGAAGGCCCAGGCCAGCTGCCCTCCCTCCCAGCCCAGAGGC
CTGAACTGCTCTGCTGGCCCCAGCAACCCCCTCAGCATTGGATAGGGGAACTGTGGCTCC
CCACACAGGCCCCTGAGGCCCAGCCCAGCAAGCTGGGGGCTGCAGGCACAATCCCTGAAGT

TABLE 1-continued

| SEQID NO: 1 |
| --- |

AGCCCCAATAGCACTTAACACTCCAGAGTCCCAGGAAGCGCCCACCTCTCACAAAGAGAAA
AAGGGATCTCAGAAATGAGACTTAGTGACAGCTACCCTGATGAGATTCACCCAGCTCATCA
GAGAGTACTGTGTCCCCATAGGCTACAGGGCCTCAGGAGGCATCTGGCCCCTATTCTAGG
CTCTGGCTGGGAACCGGGGAGGGGTGACCTGGCCTCTGGTGGAGCTTCCAATGGGCAGGGA
AGCTCCCCTCAAAGGGCTCTCCCTCCAGAGCAGATCCTGAGAACTTCCTCTGAGGAAGG
CCCCCTCCTAGGGCTGCTTACAGCTGGACCTGGCAAGGGAAGATGGTCCCTCCCACCTC
CCCTCCCACTGACCCATGCGAGGGCAACCTCTCTTTCCTCACAGCAGCCGGCTCTTTCC

AGCTGTGTGGCCTGCACATGTGTGTGTGTGTACATTTGTATGCAGTGTGCCTGCAACCTC
AGGTGTACCAACCACCACACAACAGTTCTGGTTGAAACTCCAGCTGGTGGCCTGTGGTTCC
TGCCACCCTTGTATCCAGGACTCAGCCTGGGGAGGGCACCCTGCAGATGCTCTGCCAATG
GGATGGTAGCTGGCAACCTTCGCTTGTGCCCAGAGTTCTGGGAACAGGGCTGTGGGCCCT
CTGTGGGTGCCGTCTCCTGCCTGCTCCCCCAGTGTCCAGCTGTGCTCCCCTCCCACCACCC
CATCCCCAGCAGAGACCTGGCCCCTGCTCCTGTGGCTCTCCCGCTGGGTTT
GGCTGCATTGAACAGGAAGAGTCCCTGGGATCACTTGGCTTCCCTGTCC
CCTCACGCCTGCTGACCCTGTGTCTGGCTAAGTTAGGGAGCAGGGCAGGTCAGGAGAGGT

GGGTCTGCATTGATGTGACGTGGCCCTGAAGCTCCCTACCTCTCCTCTTAGCAACTTCCT
CTGCACTGCCCCCTCTGCATACCAGGCCCAGAAGCAGGCAACCTGTTGTGGCTCCCTGAGG
CACCTGTCCCTCTGCAACAGGTACTGATTTCTATCTACATTGGCAGAAATAAAGGCAC
AACATCTGGGCCAGATTATGGCCTGTCCTGACCCACAGTGGGGAAAGGATGTATGTCCAC
CCCTGTTCCTAGAGGGGGGAAGTGAAGCTTCCTAGAGTCCACTC
CTTCCTCACCCACCCGTCCACGCAGGACCTAGCAGCAGCCCCTCACAGGACCACTAG
AAGGGCTGCTGCAGCTACCCACGGGCTCTCTCCCTGTCTGGTCGGTCTTTCTGTCCCTTG
TTCCCAGCTTCTCTTGGTTCCAATGTTGTAGCCATGCGTTCTGGGAAACACACTCACTCAG

AAGCACAATGCAAATAACGGAGTGCAGTTTATTACACCGCGGGCCCAGGCCAGAGTCTCC
TCTTAGCCAAGGACCCCGACCAGTTTTTCTGAAAACCTTATATACCCTAAGTGTACGTGCC
CAAACCCACCTCCCAAATTCCCTGAAACTTGTCTGAACAGAGGAAAAGAAAGATACAGTC
AAAGTTAACCTGTGATTCATATGCCTTAAGCCTAGGTAGTTAACAGTGGACCATTATTAAT
AGCCCTGTGATCATACCCCAATAAGCATAATGAGAATTTATGATTCTATGCCCTTACACAGA
TAATTAGGGTATTCTTTAGGTAACAGAGAGTCTAGGAACGAGCCCTGGGGCTCTTCCATCC
GGAGGGGTCTGGTTTTCCAGTTGGTGTGTCGTTTCCATAGATACTGGCATATAGCTCAAA
GTCCACAGTCCGGCCCAAGATGGAGTCCTGCTTTCAAGATGGAGCCTGGTCTGTCTGTTTC

CTCCTTCATCC ATAGTATGAGCATCATTCATAGGGATTT
ATTGCACCCTGACTCTCCCACCTCCAATTTGGAGAACGACATCAACCTTTGGTTACAGA
GTTCATAATACATTGTAAAATAAAGGCTCCACAAAGCAGAACTATGAAGGCAACTATAACA
ATGGTAAATATAGTTTTCCACCAATCACCCTTCACCCAACATAGGACTGAAGTCCAAAAAG
GAAGATGTATCAGACATAACTTTTACCTGACCTTTCATGTCATCTAGGCTAGCTGATCTAT
AGCCAGATAAATCAGGAATATACACACAACATTCAACTTTAATTATAGCACAGGTCCCTCT
TTGTACTGAAACTGTCGTCAATCTCAAGATGATAGCAGCAAGTCCTT
CTTCATCTCTGTTTCTTCTTTAAGATGATCTTGGTTTCATGGGCATCAGAGG

GTCCCTCTGCACAGTCCACTCGGCGTCCTCGGGTCTGCATGGTATGCTCTCTTCAGCCTC
ATGTGGAGCATCCAGGGACTGACACCTGCAACTTTAACTGCAGTAGGGCTGGTTAGAACAA
CAGCATATGGACCCTTCCAATGTGGGCCAAGGACTCGTGTTTCCAGTCCTTGACCACACC
CGATCCCTGGGCACAAATTCGTGAATCTGTTCCCCAAGGCGGAACGGCACCTTTTCTTGTA
CAAACTTAGTTACCTGATTTATTACCTTACCCAGTTGTTCCATCTGCTGTGAAATCTCATC
TCCCCTTACCTGAGGCAAATTTGTTGACACCTGTTTTATTATGGGAGGGGCCTCCCATAC
ACAATTTTGTACAGAGACGATTCATGGGACTCTGGGGTCATCCTGAGTCTGAGCAGA
CCAGGAACCGTCAGTCTCCAACATCCACTTGGAGAGTGTCTCTAA

GTGTCCGGCTGGTTCCTTCCACCATCCCAGAACTCTGGGGCCTATATGCTGTATGTAATTT
CCACTTGATGTTTAAAGTTTTGCTTACTTGGTTATACTAAAACAGCTACAAAAGCCGGCTC
ATTGTCCGATCCAATGCTGGTAGGAAATCCAAATCTGGGAACTATCTCCCTAAGCAGGCAC
CGGGCTACTTTTGATGCTCTTTCAGTGAGGGTAGGAAAAGCTTCTACCCATCCTGAGAACG
TACATACTGTGACCAGCACGTAATGGTAGTGTCCCTGAGGTTTCATTTCAGGAAGTCCAC
TTCCAGGTGTTCAAAGGGCAGCCGTGCCTTTTACCTGAATCCCTGCAGGTTTCTGTCTGTGC
CAACAGGCAGGCATTGGCCTGTAAGCAGGCAGTGCAGTTCTGAGATTTTGTCCTGCATGGGG

AAGAGAGGAGGGGAACAAAGAAATAGTTTCAAATTATCTCTTCCAGTTTATCATG
GTGTTTGGCTTACCAGAGTGGGTGCCAGCTCCTCCGGTACCCATAAT
TTGCCACTTGGCAATTCCCACTATCCCTTTTCAGTCTTGATGGCCCCTTCTGCTTTGGCTA
GTTGGTTTTGAGCTTCAGTGTATTTTGGAGAGTCTAGTGTTAGCTCAGGTAGCTCCGCCAA
TATGAAAGCTTTAACAGGGGCTTCACTTGTCACCCCCAAGCCCTTGGCTGCTTGTTTAGCG
GTCTTATCTGCCAGTCTGTTCCCTGAGCCCGGGGAGTATCCTCTTTTTGACGTTCTCAGCA
GTGTATGACTGCAATCCTTTCTGGTTCCCAGGCAGCATCTAATAGGGTCTTAATTTCTTCC
TTATTTTTTATCTTTTTCACTAGCTGTCAAAGGCCTCTCTCCTTATACAGAGCCCTGTAGT

GTGGCAAAAGCATACCTGGAGTCTGTGTCAAGGTTTGTCTTCTTACCTTTTGACAGCTGGA
GGGCCTGGATTAGAGCATATAGTTCAGCCTGTTGAATGGAGCAGTGTGCTGGCAGAGAGGG
AGCCTCAACAATGGTTTCTTCTGTGACCACTGCATATCCTGACAGTCATTGTCCTTGTTTC
ACCAGGCTGGTGCTATTGGTGTACACGACCGAATCTGGGTCCGGGATTGGCTGGTCTCTCA
AGT CTTGCGATCATGTGAGGGCCCACCTTCTCCCACAGGAA
GGAGAGTGGCCAGATTCAGGGCCTGACAAGGCTCAGTAGTAACATGGGGGTTCTCACATAA
CAGTCCCTGGTACTGAGTAATCTGGGATGTTGACAGCCATTTATGGAGGTCCCCTTGCAGG

AGAGTGTTGACCTCATGTGGGACTTTTACAAACAAATCTTGGCCCAAAGTCAGCTTGGTTG
CATCCTGGACCAGTAAGGCAACTGCCTGTAAGCATCCCAGCCACCCAGTAGCAACACTGTC
CAGCTGATTAGAGGTAAGTCACAGCTCTGTCCCATGTCCCCATAGTCTGGGACAACACTCC
TATAGCCACCTTGTCCTTTTCAGTCATGTAAAGACTAAATGGCTTAGCAAGGTCTGGCAGG
CCCAAGGCGGGTGCTGATGTAACTGTACTGGGTTTGAGTTTTATTACCACTGGGACTTGTT

TABLE 1-continued

SEQID NO: 1

TTGCAAGCCTCGGGGGGTTGTCTTCTGCC AGTTAACTCTCT
CTCTTGACCATTGAGCCTGTCCGGTTTCCCTTCTGGGAGATCGTGCAATCTCCCTTCATCT
TGAGGGTTACTGAGACGAAGAGTAAATAGGTCGTTAAGCCCACTCGAACAGTCGGTCTTT
CTTGGGGAGACAGTGACTTGTTCCCCCAATTTAGACAGCAAGTCTCTTCCTAACAAAGGTA
CTGGGCATTCAGGGATGTATAAAAACTCATGAGTCACTTGGTGTCCCCCCATCTGACATTT
TCAGGGTAGGCTAGAGACACAAGGCTGCATTTATCACCATCTGAGACCCAGCAGCCTCTGG

CTGGGTCTATTGGCGTATAAAGTCTATAGGCCTCGCATAGTCTTTCGCAGAACTCAGGCTG
ATTCGCTTTCCCTTTGAATCACTTCAGAGGGTTTTGTGATACTTATAGCTTTTCGGCCCC
CCTCTTGAGACCTTGTAAAATAGCCACCCGATAACTCTCCAGGTGGC
CAGTCCCAGTTGGCCCTCTCATCCGGGGTGGCTAGTTCTGCCCACCGCTGCGGGT
TTGCGGTACCCTCAGGTGCCATTTCGGAGAAGGCAATGGCACCCCACTCCAGTACTCTTGC
CTGGAAAATCCCATGGACGGAGGAGCCTGGTGGGCTACAGTCCATGGGGTCGCTAAGAGTC
GGACACGACTGAGCGACTTCACTTTCACTTTTCACTTTCATGCATTGGAGAAGGAAATGGC
AACCCACTCCAGTGTTCTTGCCTGCAGAATCCCAGGGACGGGGGAGCCTGGTGGGCTGCCG

TCTCTGGGGTCGCACAGAGTTGGACACGACTGAAGCGACTTAGCAGCAGTAGCAGCAGCAG
CAGGTGCTATTTTTCTTAACCATTTTCTGGCCTCAGTTAGGATCCTGTGTCTTTCCTCAGT
GCTGAAAAGGGAGACTAGTAGTTGGATTATGTCATCCTATGTAGGGCCGGGGTTCGAAAA B
ATAGTCTCTAATAGCCTAATCACGGCTTGTGCTCCCCGGAGTATGGTGGAGTGTGTCTCTG
CCAGTTTAATATATTCGTAGAGGAAAATGGCTAGTAATAATAGGCTACAGGGGCTGATGGT
AGTGCCCCATGTGTCCTGAACTGGAGGCTGTTGTAGCTTTCTAAGGGGCATCTGTAGTGGG
GTTCTTTCCCCCTGTTCCTTGGTGGAGTGCAGCCTCTGTCTAATTGCTGTGTTTTGTTCCC

CCTTCCCATCAGTACTCACCGGGAGAGGTGGATACAATCTAGGAGGTCCAGCTGAGGTGGA
ATTCTGGGGACATTGACCAGAGGTCTCCATTGCTGGGATTGGAGCCTGCCGAAACGGCAGC
TCTACGAACTCCGGGAGAGCTGGTGGAAGAGCAGTGGCTGCTGCAGGAACTTCACCTGGCC
CTGGATGGGGCAGTAAGGTGGCCTCCGGTCCTGGTGGAGCACTGGGAGGCAGGCGTGTCAT
TATCCAGTATGGGGGAGGGGTCAGGTCATTTCCGTCCAAATCCTGTAAAATTTCCTTTTTT
ATCATCAGTCAATTTTTGTGCCATTAATATTTTCCCCTTTCCCTTCTGGATACAGAACCTT
GTCCAAGTAGGAGGGTCTTGAGCTAACCCTACCCATGAGTCAATATATGGATATTGATCCA
GGTGTCCGGGCTCTCCTGTGATTACTGTATAGACGGCTTCCACTATTTTTAAGTTCATGGT

GTTCTCTGGTGGCCATCCTACTCCCATAGGGGGCCATTCGACCTCACAGAGTATGTGGAGG
CGGTTAGGCTTCATCTTCACCCCGTTCAGTTCAGTTCAGTTGCTCAGTCGTGTCCAACTCT
TTGCGACCCCATGAATTGCAGCATGCCAGGCCTCCCTGTCCATCACCAACTCCTGGAGTTC
ACTCAAACTCACCTCCATCAAGTTGGTGATGCCATCCAGCCATCTCATCCTCTGTCATCCC
CTTCTCCTCCTGCCCCCAGTCCCTCCCAGCATCAGAGTCTTTTCCAGTGAGTGAACTCTTT
GCATGAGGTGGCCAGTCTCCTCCAAATCCCTTCTTTAAATTTTTAATCATGCACTCCAATA

CAGTTGCCTTAGATTCACTTCCCCTCATCTTGCTTACCTTCTCGGACCTTCTACTTTTCCT
TTCGTTCTGTCTACGAAGTTCTCAGTACCCTATGTACTTCTGATATTTCCACTCAATGACA
CTTAAATTGCCATTCTGCCACCTTCCTAATAGGGGTGAGAAAAGCCTTACCTGCCAGATCC
CAGAGGGAGAAGGGGGATTGGCATGTCTTCACCTGCCGGTCAGCACAACCAAACCAGACCA
CCACGTGATCCAAGATTGTTTCTCCCTTAACTTTTAAAGTCCATTCTGCCTCGGTGGGCTT
GATCAGGTGCGGATGAAAATACAGATGGGTTAAATATCCCATGTCCCAGGCCATCTCTGGA

AAAGCCAATTCGTACTCACTTATGTATCCCCCTCCTATCCTGAGAATTCCGAGGGGGTCAA
GAATTTCATAGCAGATGGGACATCTCCTTGGGGAGGGCAGAATACGAGCACACAGAAACCA
AGTTTCTTCTCCTAAAAATCCCCTGGCAATTGCTTGGTAATAATTTCCCCAAGATGGCAT
GGACACCACCTCCTAAATGACCTTCACAAGTTTCCTTCCTAAGCCCTAACACACTCATCAA
CCTGTGTACCAAGCAATCGTTGCCACCTGCCTATTCCAGGCTCCTGTGGGTCTGTGCCCCT
TCTAGTCCCTCCCAGGGCGGTGATCAGGCCCCCTCTTCCACCTTGCTGGGTGGGTTCCTCC

TCACCTGAGCACTCAGTTCCCCTGCTGCCATCCACTACCTGCTAACATGAAAGGTCCGGGC
ATTGAGAAGCAGAATCCTTCCAGAAGGGCGAGGTGCCTTCCCCCCTCTAGAAGATTTGAGC
CACAAGGCCTCAGAGTAGTCCCAAATGGGACTTGTCTCCTCAAAGTGAGGAGTTTCCCGGC
CAACGCACCAAATGTTGTAGCCACACGTTCTGGGAAACAAACTCACTCAGAAGGACAATGC
AGATAGTGGAGTGCAGTTTATTACACCAGCGGGCCCAAGGCAGAGTCTCCTCTTAGCCAAG
GACCCCGACCAGTTTTTCTGAAAACCTTATATACCCTGGGTCGGGAAGATCCCCTGGAGAA
GGAAATGGCAACCCACTCCAGTACTCTTGCCTGGAGAATTCCATGGAGGGAGGATCCTGGT
AGGCTACAGTCCATAGGGTCGCAAAGAGTCAGACACAACTGAGCGACTTCACTATATACCC

TAAGTGTATGTGCCCAAACCCACCTCCTCAAATTCCCTGAAACTAGTCTGAACAAAGGAAA
AGAAAGATACAATCAAAGTTAACCCTTGATTCATATGCCTTAAGCCTAGGTAGTTAACAGT
GGACAATTATCAATAGCCCTGTGGCATACCCCAATAAGCATAATAGAATTTATGATTTTAT
TTGGTTACACAGATAATTAGGGTATTTTAGGTAACAGAGAGTCTAGGAACGAGCCCTGGGA
CTCTTCCATCCGGGGGGTCTGGTTTTCCAGTTGGTGTGTCGTTTCCATAGATACTGGGCAT
ATAGCTCAGAGTCCACAGTCCAGCCCAAGATGGAGTCCTGCTTTCAAGATGGAGCCTGGTC
TGTCTGTTTCCTCCTTCACCAATAGGTGTCTGTCTGCCACTCCTCTTCATCTTGACATCCA
GCTGGTCAATACCTCCAAGAAGCACCGCCCCCCAACTCAGACCTTTGGGCTGGACTGTGCA
TCTCTCTTGGCCTGGCCATGGCCCTCAGCAGGAATACAGGGTCTCCTGACTCACCGGCACT
GACCACACCTGGGTGCCACCCTGGCTCCTCCAGCTTTCTGTTTCCTCCTAGACATGGGCAG

GACCTGGCCGAAAGAGATGGATTTGGGGCTGTCCTAGAGGGGAGGGACAGAAGGTATGGAT
CAGCTAGCTCCACCCCATCCCCTACCTCAGGGGTCCCCAACCCTGAGGCCATGGACCGCTA
CTGGTCAGTGGCCTGTTAGGATTCAGACCACACAGCAAGAGGTGAGGGGTCGGAGTGCTGG
TGAACAAGCGAAATTTCATCTGTGTTTACAGCTGCTCCCCATTTTGGCATTACCAGCTGAG
CTTTGCCTCCTGTGAGATCAGTGGCGGCATAATGAACGTAATGCGTGTGAATCATCCCCAA
GCCTCTCCCCACCCAACTCCAAATTCGTGGAAAAACTGTCTTCCACAAAACTGGTCTCTGG
TACCAAAAAGGTTGGGGACAGCTGCCCTACCTTTGATTTCCCTGGTGGCTCAGACGTATCT
GCCTACAATGTGGCAGTCCTGGGTTCGATCCCTGGGTCGGGAAGATCCCCTGGAGAAGGAA
ATGGCAACCCATTCCAGTACCCTTGCCTGGAGAATCCCATGGATGGAGGAGCCTGGTGGGC
TCTACCTTTTCTCCAGGTGTCTACTACCCCCTCCTCTGTTCGGCTGGCGCCCCCTGGTGGC
TGAAGCCTGTCTTGGCAGGCGTCCCGGCCCTGGGTTCCCCAGGCCTGCGGGTCTGGCCTTG

TABLE 1-continued

| SEQID NO: 1 |
|---|
| GCCCTTGTTTCCCTGAGACCTCACCAGGCTGGCTTCTCCTGGTCTCGTGCAGTCTCCTGAG<br>CTTGTTTTTACTGGGCCTCTGTAGTTGGCTCTGCCTGGATGTGCAAATCCCTCGACCCCAT<br>CCTTCGGGTCTCTGTACAGTCATCCCCCACGTAGATGCTGCGATCTAGGGCAATCTCTGCT<br>ACAGGGTAACCTTCCAGGGGCAAAGAGCTCACCCGACTCGGCACCTGCCTCCTGCACTGAG<br>CCCACCCCCGGAGGAGTTTGGCCGGGGCCGGGCAGGATGAATGCTGAGTAATGAAGGAGGA<br>GGGGTGCCGGGGTCAGCGGCCGCTGCCCTGCGACCCAGCCCCAATTCTTCCACAAGCTCTC<br>ACTTAATGCCACCTCCCGACAGCGCGGGCTAACCAGCAGTGTGGGCCCTGCCCGGGGCTCG<br>TGGGTGGGCATACAGCCCGCGGACTCAAGTGGGCCCCTCCCGGCCTTAGCCTCACCTGAGG<br>GGGCGATCGGGGCCGGGCTGCACGCCGCCTCCTTCCCAGCGGTTGGCCCCAGTCCAACAGC<br>GACGTCCCGCTGTGAAACGCCCATTGTCTGCTGAGGCCGAGGGGGAGGGGATGGCCCTGAG<br>ACCCGACTCTAGGAGGCTGGGGGAGGGGGCCGCCCTGCCCCATCCTCTTCCCCTCCCCCGC<br>CAGGGCGGCCAGACACCTGTGGCTGGAGGCCGCCTGGCACTCGACTGTTGGATACACTTTA<br>CACACTAGCGGGGTACCCTCGAGGGCCCAGGAGTGGAGACTGGCGGAGGTCCCCACAGCAA<br>AGGTGTGTGCGCATGCGTAGAGTGTGTCTGCTGCCGGGAGGGCGGTGCCACCCCACTCCCA<br>CCCCATCCTTTTGGAGCGCGCCGGCCCCTCCCCTACAGAGCGAAAGGGATCAGAGGGAGGC<br>CAGTAGGTGGGACTTCATATTCTCTGTGGACTTCGTTCCCGGTCTTCCTCGCAGGGCAAGG<br>GAAGCGTCTGGAGGGGCCCAACCACACGCGTGTATGTGGGGGTACACCCGATGTGTGCTGT<br>GTGGATGAGGGGCAAATTTTGCATTGCATGAAGGTGTGCAGTGTGTATGCACACAGGTGTG<br>TGTGTGACTGCACAGTGCCTGTGCAGACTTGAGTGAGTGGTTGTACGTATGTCCGCATATG<br>GGAGACCTGGAACATGGAGTG |

TABLE 2

| SEQ ID NO: 2, DELETION BREAKPOINT REGION: |
|---|
| AAGCAGCAGCCAAGAAAGTAGAACTCACAAAAAATGAAGGATAATTGTT |
| ACATTTCTGTTTGTTATTTCAAAGAAGCACGTGGAGGAAAGAGGGCTAA |
| GCTTATTTTCGTGTTTGATGTTGTTTTCACTTTGAATTCCCTTGTGGGG |
| CACAATCATGTTTTGAGTTTTGGGGATGCCAGCCCATGGTGGCCTGGGCA |
| GTCTTGTCTGCATCCCACAAACCTCTCTGGAGGCTCACTGTAGGCCTGA |
| CGTTCTTGGGGCTGGGGAGGCCTCTCCTGAACTCTGAACTGATGTGGGA |
| GGAAAAGGCAAATGAGCAAAATAAATAATGACATGGTTTCCAGAGACAG |
| AAAGAAATGTGTAGGTTTTGGGGGGAGCCGAAAGCCTTCTTTCCACTGA |
| GTGGTCTGGATGGTATTTTTGCAGTGAGCTCTGCT▲**GGAGAAGGCAATG** |

TABLE 2-continued

| SEQ ID NO: 2, DELETION BREAKPOINT REGION: |
|---|
| **GCA**▲CCCCACTCCAGTACTCTTGCCTGGAAAATCCCATGGACGGAGGAG |
| CCTGGTGGGCTACAGTCCATGGGGTCGCTAAGAGTCGGACACGACTGAG |
| CGACTTCACTTTCACTTTTCACTTTCATGCATTGGAGAAGGAAATGGCA |
| ACCCACTCCAGTGTTCTTGCCTGCAGAATCCCAGGGACGGGGGAGCCTG |
| GTGGGCTGCCGTCTCTGGGGTCGCACAGAGTTGGACACGACTGAAGCGA |
| CTTAGCAGCAGTAGCAGCAGCAGCAGGTGCTATTTTTCTTAACCATTTT |
| CTGGCCTCAGTTAGGATCCTGTGTCTTTCCTCAGTGCTGAAAAGGGAGA |
| CTAGTAGTTGGATTATGTCATCCTA |

▲Arrows indicate the position of the deletion breakpoint that corresponds to the joining at a simple 16 bp sequence motif (highlighted and underlined)

TABLE 3

SEQUENCE LISTING SUMMARY

| SEQ ID NO | DESCRIPTION | LOCATION IN SEQ ID NO: 1 |
|---|---|---|
| 1 | Normal: Upstream, Middle, Downstream Regions | 1-35035 |
| 2 | Mutation: Upstream and Downstream (middle deleted) | 1-6491 + SEQ ID NO: 10 + 29871-35035 |
| 3 | Middle Region - (deleted for AM mutant) | 6508-29854 |
| 4 | Middle Region + SEQ ID NO: 10 | 6508-29870 |
| 5 | SEQ ID NO: 10 + Middle Region | 6492-29854 |
| 6 | Upstream Region - (no SEQ ID NO: 10) | 1-6491 |
| 7 | Upstream Region - (with SEQ ID NO: 10) | 1-6507 |
| 8 | (No SEQ ID NO: 10) - Downstream Region | 29871-35035 |
| 9 | SEQ ID NO: 10 + Downstream Region | 29855-35035 |
| 10 | GGAGAAGGCAATGGCA | 16 bp sequence at start or end of deletion of SEQ ID NO: 3 6492-6507 or 29855-29870 |
| 11 | Primer 1 - upstream region | 6328-6349 |
| 12 | Primer 2 - downstream region target sequence | 30176-30197 |
| 13 | Primer 2 - downstream (reverse complement of SEQ ID NO: 12) | 30176-30,197 |
| 14 | Primer 3 - middle region [reverse primer] | 6882-6903 |
| 15 | Primer 3 - middle region (reverse complement of SEQ ID NO: 14) | 6903-6882 |

TABLE 3-continued

| SEQUENCE LISTING SUMMARY | | |
|---|---|---|
| SEQ ID NO | DESCRIPTION | LOCATION IN SEQ ID NO: 1 |
| 16 | Truncated upstream (no SEQ ID NO: 10) | 1872-6491 |
| 17 | Truncated upstream (with SEQ ID NO: 10) | 1872-6507 |
| 18 | Upstream | 6063-6491 |
| 19 | Downstream | 29871-30234 |

TABLE 4

| Summary of PCR product generated by three primers to determine AH status | | | |
|---|---|---|---|
| Primer Pair | AMF | AMC | AMA |
| Primers 1-2 ($L_{12}$) | No product | Product I produced: $L_{12}$ (from mutant allele) | Product I produced: $L_{12}$ |
| Primers 1-3 ($L_{13}$) | Product II produced $L_{13}$ | Product II produced: $L_{13}$ (from normal allele) | No product |

Primer 1: primer binds upstream region
Primer 2: primer binds downstream region
Primer 3: primer binds middle (e.g. mutant) region
Primer 1-2: Length = $L_{12}$
Primer 1-3: Length = $L_{13}$, where $L_{12} \neq L_{13}$ for assays based on length difference

We claim:

1. A method of diagnosing a deletion mutation in a bovine genome, said method comprising:

obtaining a DNA sample from the bovine;

analyzing said DNA sample to determine the presence or absence of a deletion mutation, wherein said deletion mutation comprises deletion of SEQ ID NO:3 and said deletion mutation is at a breakpoint between nucleotides 429 and 430 or between nucleotides 445 and 446 of SEQ ID NO:2; and diagnosing the bovine as a carrier of Arthrogryposis Multiplex (AM) when the analyzed DNA has the deletion mutation or diagnosing the bovine as not a carrier of AM when the analyzed DNA does not have the deletion mutation;

wherein the step of analyzing the DNA sample is by polymerase chain reaction (PCR).

2. The method of claim 1, wherein said deletion mutation further comprises SEQ ID NO:10.

3. The method of claim 2, wherein said deletion mutation is SEQ ID NO:4 or SEQ ID NO:5.

4. The method of claim 1, wherein a region upstream from said deletion mutation comprises the sequence from base 1 to 6491 of SEQ ID NO:1 (cross-referenced as SEQ ID NO:6), from base 1 to 6507 of SEQ ID NO:1 (cross-referenced as SEQ ID NO:7), from base 1872 to base 6491 of SEQ ID NO:1 (cross-referenced as SEQ ID NO:16), or from base 1872 to base 6507 of SEQ ID NO:1 (cross-referenced as SEQ ID NO:17).

5. The method of claim 1, wherein a region downstream from said deletion mutation comprises the sequence from base 29871 to 35035 of SEQ ID NO:1 (cross-referenced as SEQ ID NO:8), from base 29855 to 35035 of SEQ ID NO:1 (cross-referenced as SEQ ID NO:9), or from base 29871 to 30234 of SEQ ID NO:1 (cross-referenced as SEQ ID NO:19).

6. The method of claim 1, wherein the step of PCR further comprises:

providing a forward primer which binds specifically to a first selected DNA upstream region, said first selected DNA upstream region corresponding to between bases 3000 and 6491 of SEQ ID NO:1;

providing a reverse primer which binds specifically to a second selected DNA downstream region, said selected DNA downstream region corresponding to between bases 29871 and 35035 of SEQ ID NO:1; and performing PCR amplification such that said forward and reverse primer generate an amplified DNA product only in the presence of a DNA sample comprising the deletion mutation associated with AM.

7. The method of claim 6, wherein the forward primer has a sequence that is SEQ ID NO:11 and the reverse primer has a sequence that is a reverse complement to SEQ ID NO:12 (cross-referenced as SEQ ID NO:13).

8. The method of claim 6 further comprising providing a third primer, said third primer capable of specific binding to at least a portion of the middle region of DNA, said middle region corresponding to a DNA sequence encompassed by bases 6507 and 7500 of SEQ ID NO:1, wherein DNA that contains said middle region results in amplification of a first DNA product by said forward primer and said third primer, and wherein DNA that does not contain said middle region results in amplification of a second DNA product by said forward primer and said reverse primer.

9. The method of claim 8, wherein the third primer has a sequence that is a reverse complement of SEQ ID NO:14 (cross-referenced as SEQ ID NO:15).

10. The method of claim 8, wherein said amplified first DNA product and second DNA product have lengths that are at least 10% different, said method further comprising:

determining the length of the amplified DNA product; and identifying the presence or absence of the AM mutation based on said determined length.

11. The method of claim 1 further comprising providing a forward primer and a reverse primer, wherein said forward primer is capable of specific binding to SEQ ID NO:3, and said reverse primer is capable of specific binding to SEQ ID NO:3, wherein said binding regions are different and the primers are capable of generating an amplification DNA product only if the DNA sample does not comprise said deletion mutation.

12. The method of claim 1 further comprising providing a probe or primer that specifically binds to the sample of DNA having said deletion mutation; and identifying the sample as containing the deletion mutation gene for DNA samples that hybridize with said probe or primer; wherein said specific binding is at a location that includes nucleotides 429 and 430 or between nucleotides 445 and 446 of SEQ ID NO:2.

13. The method of claim 1, wherein the analyzing the DNA sample further comprises providing a DNA probe or primer, wherein said DNA probe or primer specifically binds to SEQ ID NO:3 and does not specifically bind to bovine DNA comprising SEQ ID NO:2.

14. The method of claim 1, wherein said analyzing the DNA sample further comprises DNA sequencing.

15. The method of claim 1, wherein said analyzing the DNA sample comprises providing a probe or primer comprising a purified oligonucleotide, wherein the oligonucleotide has a length between about 15 to 50 nucleotides and specifically binds to a target sequence of SEQ ID NO:3 or complement thereof without binding to SEQ ID NO:7 or SEQ ID NO:9.

16. The method of claim 1, wherein said analyzing the DNA of the bovine subject comprises providing a probe or primer comprising a purified oligonucleotide, wherein the oligonucleotide has a length between about 15 to 50 nucleotides and specifically binds a breakpoint mutation region in the bovine genome, said breakpoint located between bases T429 and G430, 445A and 446C, or both of SEQ ID NO:2.

17. The method of claim 1, wherein the bovine is an Angus or Angus composite.

18. The method of claim 1, wherein the DNA sample is obtained from blood or semen.

19. A method of diagnosing a deletion mutation in a bovine genome, said method comprising:

obtaining a DNA sample from the bovine;

analyzing said DNA sample to determine the presence or absence of a deletion mutation, wherein said deletion mutation comprises deletion of SEQ ID NO:3 and said deletion mutation is at a breakpoint between nucleotides 429 and 430 or between nucleotides 445 and 446 of SEQ ID NO:2; and said analyzing is by PCR or probing to detect the presence or absence of SEQ ID NO:3.

* * * * *

SEQUENCE LISTING

```
<160> NUMBER OF SEQ ID NOS: 19

<210> SEQ ID NO 1
<211> LENGTH: 35035
<212> TYPE: DNA
<213> ORGANISM: Bos taurus
<220> FEATURE:
<221> NAME/KEY: Unsure
<222> LOCATION: (1)..(35035)
<223> OTHER INFORMATION: N residues are not defined
<220> FEATURE:
<221> NAME/KEY: misc_feature
<222> LOCATION: (1822)..(1871)
<223> OTHER INFORMATION: n is a, c, g, or t

<400> SEQUENCE: 1

aggaccatgg agcctcccca cacctggagc tgctgagccc tatcccacgt gctagacaga      60

gtaaggggtg ctgggggatc ctagcgaagg gaagtcctcc tcttcaccag cctctggccc     120

acttgtgggt aaagacggga aggcaggaat tggcccccac gtccccacac agacatgcag     180

actttttgtt tgaagcagga gcccaggagg tgagcccaaa gtcaccaggt gggtgtcagg     240

gtcaggcagg acaccaagaa gagacctctg aagcagcatc agccagttgc ctcttggtca     300

ccatggacac caggctgcaa agaaggttga tgtgcccact ggggacaggt cagtgtggcc     360

ctgggggcag gttgcagggt ttgtgctggg aatggcaggg ctgatgggaa caggcctctc     420

tgggcagggc agtcagctct gtggttccca gcacggagca ttgcccatgc ctgtttttgt     480

ttgaaatctg gggccccaga acccccaaca ccatgttctg atacagtgtg ccccctcagt     540

tactgaaaca gaaatggccc taagccctgc ccacaagcca cagggatggg gcctgggctg     600

tggctggtca gcccaggatg ggaatggaag gggacagggg gctggcctgt ccctgcaccc     660

gcagctggca ctcacagggg aactgcttcc caatggacat gagtccagtc tgctctgctc     720

atcaccacca ctgcaagggc tgtttctggg ccttgctcca cccatcctct tccacaaccc     780
```

-continued

```
catcatcaag tgggcacgtg atgctggagg ccctgggtga ccatgggcac attagttgta    840
tattgctatt gttacttaca ataactttaa ttttacataa aacattgtta attatagctg    900
tacaacaaat taacctacaa tttatccgtt taaaacaaca aacacattat ctcacacaat    960
ttctgaggga taggagtcct ggaactgctc agctgggtgg tcccggctct cagtctcttc   1020
ggattgctac tgagatgtcg gcagcagctg gggtcccagc tgaaggctgg agaccagctt   1080
ataaacccca cactctgttg gccgctccat agcaaaggac agctggcctc ctccaagtgg   1140
aggatgttag agacagagag agacaggcca ggatgcccct gcgacctcat cttctacagg   1200
accttactgc tgatgcaggt caacctcagt acattcagag gtagagtacc aggtcggggc   1260
tcttgggggg gctgcctcct gggaggctgt caaccccagg gcctgtttcc ttgcccagtg   1320
gtgcctccca ggataggtat ggcccctaga gcttcaaggg gcagagagca gccagacacg   1380
gctccagaac cctctgggct cagcttcttt cttgggggaa aggggagcag gtcctggagc   1440
ctagaggagg ctgttggggc ctggagataa tcaggtgatc acaggagctc tggttgggaa   1500
gctaagggct cacctttcaa aagtcaaggc tcccaggagc cccaggtcct accccatttc   1560
aaactcccaa gtacctggag ttttctgggc ctggcgaggc cgactgctgt caccgttagg   1620
accaactctt tctccagatt tcaaacacct atgatttgct gtcattgtta gtccccaagc   1680
cctgacctca caggcaagaa agagggaccc agagtcacag ggttccacag ggcgagacac   1740
ccacagaggc aggcagagca cctgactaca cacaggaatt cagcaaacac tcattgaccc   1800
ttggtcccca ccaggaactg gnnnnnnnnn nnnnnnnnnn nnnnnnnnnn nnnnnnnnnn   1860
nnnnnnnnnn nggattgcgg tgcagaggaa ttccccagag cccctctgag gcaggggagg   1920
gacaggcaat gggtggaaga gtggggaggg tgggaggaag aagagtccac cccagctctc   1980
cacagaccag gcaggggtcc aggctgagtg tggaaagggc catggctcca cccccagcag   2040
acgccaggat actgccctca gctgcccagg ggcagcctgg ggagggggccc agcctcagct   2100
gtgcttcctc agactcccct aatctaatca agggtgacac tcctttcacc caagctaatt   2160
aatgaggcct gtatggcctg agcgtctttc tgttccaagc aggtactggg gataggagtg   2220
agtgacacag acagggccct ggcttccaga gcccttggag cctggggtgg ctatctcagg   2280
tgggaaagtg gggagagaac ctcgggggc agggaggggg ctgagtaggg aagggccaaa    2340
gggggcaggg aagggacaga gacacgagga acttgcctgt ctgaggaaca gtgtggttcc   2400
ctcagagccg gagaggtccc tggagggctg acaggggcct cagcacaaac acctctttgg   2460
cgacagcgtc ttgaggacag atgaccagga acaggaagta aggaagtaaa gggaagcaca   2520
gcccaggaac agggggatct ggtttgacac tgtgattgcc ccctccctga ggagtgatga   2580
cccgagctcc atgtgacctt cctgggcagc cctcctccct ctggccacca ggtggggaga   2640
tccctcttat tctttcaggc cacgtggaac ccagctctga ggaggccttg tccacccctc   2700
tacccaccca accacctggc ttcatatccc aaagtccctt gccttcccct cctgcactga   2760
gcctccaccc caaacagctc ccctttccca aaaaagctga acttctggct cctgaaatgg   2820
accctctgca actcttctgc tgggagggct cccaggctgg tcagcagtaa tgcccccaca   2880
gtcctgctgg tgacccagct ctctgagcct ccccagggcc tggaccagtg agtgtgtgca   2940
ggtcccaggg tgtggctccc ggcccacatg gctgccactg ccccaaacca ctggcccaga   3000
ccctggacac ccagggagat gggccaggca gccagagagc aggaggggac tggcttggtg   3060
ggacttggag ggccctgctt ggtgtgcacg gctgagtcct ggagggcaga tgaaccttgg   3120
tcaggaactg ttggggtcat tggaggagga gataagcctc tagcagtgac taaccctcct   3180
```

-continued

```
cctccctgat gctccctggc caggcaggta gctggcaacc atctgatgaa attggctgtg   3240
ggtgggaaac ccatcttgcc ttgacctcag agggctcagg atgagacact gcagtgtcag   3300
ccacatgact caaccacctc ctcactgccc ctggagcaca gcgtccagca gcagcctgag   3360
gagacctagg accacaggac agtggctccc cggccaatgc cccacgctgg ctaggatcac   3420
tgtattgtgg ggtcagcata aagccagtgt tcaagacagg agcataggcc tgccaatgaa   3480
cccccaattc cttcctactg tcgggggact ccctctcagg ggaggactgg gctctggcgg   3540
gaggtgagcc ccagtacaaa gtgccctttg tcaggccggt tgggggccct gcctctagga   3600
ctcagatgcc ctcttctgct ggcccccatc tgctgggcag agactggctt ggggcaggct   3660
tgacccacag gtgccaagag tagttctgtg ctcccccggg agaaggcagg cggtgcacca   3720
ggccagaacc caagcttcag cccacctcag ccccagagac aacagcgtgc acacgtctct   3780
gccttccagg ggcctcagga ggggttgcgg ggagagaact gtgccccagg aggatgcacg   3840
acctcttctc agcactggga gacgctctgg gaaagtggta actgttccag tcctgcctga   3900
gccccccagg gacatctcac acacaccctc ctccctcgag gcggtcggct tcagcgcaga   3960
gggacacagc caaactcaag gccgggcgaa cccctgcgcg gcgcaccggc cggcccaggt   4020
gggagctgaa taaatcccca cggcccggcc cggcccggcc cgccccgccc gttcatgaga   4080
agacatcaac cgaccccggc gctgggcctc ggccaaactg gacccttcac gaagacgaca   4140
aaacaaaatt ccctacccga tctctggaaa taaccatttt ctggcacagt ctcagtcggt   4200
tgtagggccg cggtctcacc gcagccacgg cctccagggc gcgccctggc cctgagcccc   4260
ggccccgggg gcggcgaggg ccagcccggg caggaagatg ggtgccaagg ccgccccggg   4320
gcgcggcaag gggcaagggc cgtcaaaggc tggcggcggc gggcggcctg cgtagatctc   4380
gggctcctgg gcttcagtgg ctggggccag tggaagcggg cggcgcgcgg gccccagccg   4440
ggccaggcag gctgccagat ggcagagcag acgagaccgc acgtccgcag ggacgccctc   4500
gcagccagcc aggaagcgat tcacttcggc cagacactca tggaagccgg cgcgatactt   4560
gcccaggata gcggggtccg agcggagggc agctgcgggg gtggcaggga caggcggtcg   4620
gcgcccgcgg cctcagcccc ggcccctgag ccctcgccgc cgccctcgcc tcacctgtca   4680
cctgcacgcg ccgcaggctc tgcaggtgcc tcacggtcag ctccaggatg tccgccttct   4740
ccagcttcga gcggcgggag ctctgcgggc ggggccggtg agggcggcgg gccgcccagg   4800
aaggccggga ttccagactc cccagtcttg tccctacccc caactcacct ctttcctgag   4860
ggcgtccagg aggaggctct gcagctgagc cagactctcg ttgatgcgcg ctcggcgccg   4920
cttctccatg accggcttgg aggactgtgg agccggcagc cactgagtcc tgcaggcatc   4980
atctcccctc tccccttcgc gccccccccc cccccccgc cccgctcctg ccaacccacg   5040
cccggccagg tccccacctt ccggtgctcg gccacgctcc ggggctggtc tggggtccgg   5100
ctggcgccgg ccgccgctcc cgcccgcggc gaggccctcg gcttccccgg gatgtccgca   5160
ggcatggtgc gccccttcgc cacccccagc cgagggcagg ctgggcgcgc ggtttcccag   5220
gcacttctcc cgcgggtccc aggctcagct accaagcgcg tgtctgcagc agcccggcta   5280
tttaaggcag cgcggctgcg gggcgtggga atccctctcc gcgttctttc ccacactcga   5340
gccagccaat gagccgccgg cgccgggcag cccgcccccg gccgctgccc ccgccggctg   5400
tcagtcacga gtcagctccc ggcccacaga ccccgctggc aacaaaggct agccggggca   5460
ccccgcccgc gcctgcctcg gaccacgccg gccaggcggg aaaatcgccg cgccccggtc   5520
cccagttccg agcgatgcgc cgggaggggg cctctccggg agggcggagg cgcgaggctc   5580
```

```
accttcaggc cgagcggaga ccgcgagaag tctgaaagga aaattcgcga ggggccctta   5640
tgcgctcacg aagaaccggc gagcctccgc cttccgcgga tcccgcgggg gccttggacc   5700
tccgcgcagc ctgcgcatct gaccctcgcc gccagcagca cctgcacgat gccggggaca   5760
cagtgaacat ggaacaccag ccgctggaca ggagagaagc tgactggcca aggtcgtgag   5820
ggaagcaggg tggcatcaca gggccaaaga aagtaatgcc gcagagcaga tagtgacgtc   5880
atcacaggca ggatgttgtc atggtatgga atgtaaggat gttactggtc aggctggtga   5940
tgtctccaag caatcatagg tgatatctca gggttaaggt agatgatgac acaagccaga   6000
tgtaatgatg tatggtcact ggtgatgtca ctctcttctg gattacccaa aagtgatgag   6060
ccaagcagca gccaagaaag tagaactcac aaaaaatgaa ggataattgt tacatttctg   6120
tttgttattt caaagaagca cgtggaggaa agagggctaa gcttattttc gtgtttgatg   6180
ttgttttcac tttgaattcc cttgtggggc acaatcatgt tttgagtttt ggggatgcca   6240
gcccatggtg gcctgggcag tcttgtctgc atcccacaaa cctctctgga ggctcactgt   6300
aggcctgact gttcttgggg ctggggaggc ctctcctgaa ctctgaactg atgtgggagg   6360
aaaaggcaaa tgagcaaaat aaataatgac atggtttcca gagacagaaa gaaatgtgta   6420
ggttttgggg ggagccgaaa gccttctttc cactgagtgg tctggatggt atttttgcag   6480
tgagctctgc tggagaaggc aatggcaacc cactccagta cactcgcctg gaaaatccca   6540
tggatggagg aacctggtag gctgcagtcc atggggtcat tgagagttgg acaagactga   6600
gcgacttcac tttcactttt cactttcatc cattggagaa ggaaatggca acccactcca   6660
gtgttcttgc ctggagaatc ctagggacgg gggaacctag caggcggcca tttatggagt   6720
cgcacagagt cggacatgac tgaatcgact tagcagcagc tagttgcaag tccagaggag   6780
gaagtggcat tcccagaatg gaaaggaacc acagggccaa gggaggaggg gccgggacag   6840
gtgggaacca ggctctagtg gcttcaggtc cccagagggg tctaagagag tcatgcttgg   6900
cttttctgag cagcagagtg gcccaactgg cagctcggaa gggccacctc ccacactaca   6960
ttctacctgg tgggtggcga tgctggctgg cccccacctc aataccccttt cccaggggtc   7020
cagtctgggg cccagtgcag acgcctgtga tgcaggtttg atcactgggt gggggaagac   7080
accctgcccc ctccccggag gaggaaatgg caacccactc cagtattctt gcctgggaaa   7140
tcttatggac agcctggagg gctacagcca aaagggtcac aaagagtcag acacaactga   7200
gcaactgaag gaaggaccct cctgtacctg tttcctcacc tgtaaaatgg gctacctttt   7260
catttagccc tggactatag tccatggggt cgcaaagagt cgaacatgac tgagcaacta   7320
acactttcac actttgactg agaagataaa tgagatctga ttttgaaagc acccagcaca   7380
tgcaagcggg acagagtcac ctggattcac ctctgccaca agccccactg tatcctctac   7440
cctctgagac accctctccc tacctggggt cttcagaagc ctgtttcttg gcccttccag   7500
ccccaacaag gagccttctc tcacccagag cagagtgagt cccaggggtg tcatctacat   7560
ccctgtgtcc ttcccactgg gctgcacccc cactctctct ctgggccctc ctacctctgg   7620
ctgtcccctc cctgcctttt acatctggat ttgatctctg gtaggacctg ggactcctgg   7680
ggaccgtagg ggctcccttg ctctgagtag agagggagag tcctaggctg caggggggaa   7740
actgtgctga gaaatactga cgtggaacac tgcattttcc aaagatggct acaatacatc   7800
caccccaaat actctacctg tgtgtccttg gtgagatttt gtgatgacat taaccagcaa   7860
agacaggggc agtggtgatc tatgaattct gaggcttgac ttgaaaaacg tgcaccttgc   7920
tgtcctggga aactcactcc tggaaaccac tgacccctct gtgaggaaac ccgaactggt   7980
```

-continued

```
ctcatggaaa ggcctcatgg agaggccttg tataagtgtt gagctaggaa cctagaaatc   8040
tcagcttcca gacaggtgat cccaacctgc cgcttcagag cccccactca cactttccca   8100
gccagctctg tgtgctctgt tccactcttg attcacatga ctggtgttac tgtgacactt   8160
tggggtcatt cgttacgaaa caatagtaac tggaacagct aagatggccc aagccctgga   8220
cccacccccc tccccagccc caccccccaa accttgttcc ttcctttctc tggcattcac   8280
agagtcacag gagcttcccg cactggctgt ccatctgacg aggtgacttt tgcagctatc   8340
caaggccaac tatctgtcct cctagatcca ggcttgagtt ggccaagtcc cagtaggctg   8400
atggtcccag gggcatctct agggaccact gttggccact gggcaggaaa agtagtgggg   8460
gagtctgtgt gggaagataa gtgtattttc cagtccagac actgggctgc agccttggtg   8520
gggggtgggg ggatggtctt tctcacgtct ggctcccatg acagcattcc acaacattca   8580
gacagtgtcc ctccggggcc tgccaggtgc tgtctgtgca caggcccctc ccaacctctg   8640
acagggggt ggcacctgca cttgcaccct gcccctcagc attccacagg cacatgggtc   8700
cctgaatatc agagacacca tagaccatga ccagcaaccc catcctcctg ttccctcctc   8760
ttctgccaag ggacaacagg ctgtggactc aggcagccag gaccagagtt gccatgtgac   8820
caggctagag tcattgcagg gtctctcctg gagcatggga gttgggtcct gagatgataa   8880
agtggcagag gctagggctg gaggaaccca ggattcagta tagagaagaa ggaagcagat   8940
gaccaggacc ctaatcttaa ccctgagggg gcatctttca tttttacagg ccagcggacc   9000
aagacacctt ccttcggctc ttggtgctgg gcagttggag catcccccca acacctgatg   9060
catgacagca cctcccccga ggtctgggca ttgtcaacat ctttctccat tattgaatgt   9120
tgacacctct ccacgctggg gaagccatgt ctccccaatt ctgtgtggta acagagcttc   9180
ccaccctgtc tgcctgtgat gccacctccc tgtgggcttc catgggtgct tctctctcca   9240
gtctccttgg accactactc tctggagagg tatgctttgc tctcctgctg gtcacatcca   9300
gactagtttc ttcttcacca aaaaaagtcc cagctttgaa cctcatctta ttaacagatc   9360
tcatcttgtg aagtccactg caaccctgcg gggggggggc ctccccatac cttctgaagg   9420
ttcactcctg attccctgtc actttctcca gcggctcctg tcacagtcct tgttgacttc   9480
caaattcaca cggttgatct tctggacttc ctggcctcca tggggcatcc tagtgtagag   9540
ttggcaacta agcttccaat cctaagtgct gggtgtagac tgtagccgta atattcccat   9600
ccaccctgga ggacacgccc accaggaagc cccgcccaca gggcacaggt cagcatctgc   9660
agtacaatat cctgctgctt tcccagtgta acctggggtc ctgcctcctc cctccacact   9720
ctcagcctct tgtctcaggt tctgcctccc gcttctcctt gtgcctttca gtcctgtgga   9780
acttggggaa caagtcttca ctctaatctt tctatccaca caactggagc actctctgcc   9840
cagtggtgga gcctgactga ggcaccagcc tcctctgaat ctgactattc tcagttctca   9900
gaccagattc tgccatcgtc ctcgaccctc agagttcact cccagtgctg ctctggcagg   9960
tcctacagtg gctctatctc cctgatgtat acaaacacct acttctgacc tattgctttt  10020
ccaccactgg ctgcaagccg ccaccagctt cggcctggaa ttttgtagtt ctttgccatg  10080
gcaaggcagc cagtcttgga gccgagtgct caatgggggc aggtggacag gagaggagat  10140
tagagggtca gcagagtggt cagaagaaca agcctaagct cctatcttct ctcggaagct  10200
tatgggaagc catgggagag aaggttgtgt gtagatcact ctggcccttg gctccaccac  10260
agattatggg gtcaggatag aagcacagcc actcggctgt atccatagca gcctcagtgg  10320
acgagggcgc atagatataa gtgaggtcat ggatattctt gggagttttt tgttgttgct  10380
```

-continued

```
actgctgtta gatggctgaa gggcttaaaa ataaaagcaa gtgtattaaa cgatatagat  10440
actgttttaa aagttttagg aagtttaagt tagtttgtaa atgaaaccaa atattaacca  10500
aagacccctt tataagtagc cattgtaact tcataaatag gatattcagg tttttgtcta  10560
gaacatatgt attttgtgat catgttgtta ggtgcataca aattaaaaat aatttcattt  10620
tatcagtgag ctcaaccttt tattgttatg caaccttctg tatctagtaa tgctttgact  10680
ataaggtttc tttgttaatc tgttagtgaa actgttaata cggtcacatc tgcttccctt  10740
tagttaacat tacgcagtag gtttcttttc tccttttact ttcagtttcc tgtaccttta  10800
tatttcatat tatttatgtc ttctgtaagc tgtgtaaaat cagattattt ttaatcaggc  10860
tgacaatcct ggtcatttag tccccctgga tttcagacct ctgctcttta gaactgtgag  10920
ggaatacatt tctgttgttt taagccaccc agtttgtggt ggcttaaaag cctccaagac  10980
acagagacat gcttccaggg ctatcgtttt gcctgccgaa agcctttgca tctagttcct  11040
cttgtccaaa gcaggtgata ttcaataaag taataaaaga aaataaaggt tctattacta  11100
tatataccat atttttgtta tctttttaaa atttttttatt acttaaaatt tttttgaatt  11160
gttgtttcat tcccttatct ttgtgccata tttaataatg gtcacctagg gactttcctg  11220
gtggtccagt ggttaagact tagtgcttcc aatgcaaggg gcatgggttt gacccctaat  11280
cagggaacta agatcctgct ggctgcatgc catgcccgaa aaaaacaaaa caaaacaaaa  11340
caaaaaacag aatcaaaata atggtttttt gaagaagaca gggattttca cattctgtaa  11400
tatttgtttt gtttgtggct ttctttttat aatactaata ttatttatgc aaggaatgag  11460
tcaagttaga aatttagaat aatataaaca atatttaaac tgttttatgc atgttaacaa  11520
ctttggtgcc ttatgattat ttggggggaa ttgatggaat gattaattca tatgaaaaca  11580
atttggtttt ccccattcct tttatttatt taaaatttgt ttatttagtt taaaatttat  11640
ttttaaaata tttaattatt tttaggtatt tatttttatt ttatttattt attttggctc  11700
catcttgtgg gatcttagtt tcccaaccag ggatggaacc tgtgctcctg aagtgaaagt  11760
atgaagtcct aaccactgga ctgccaggga attccctaag tatttatttt tatttttagc  11820
taacatatgc ctgagatgtg ctgtttgtaa tagtaaaaat gtgggaacaa ccaatattta  11880
tttaaaaata tgagactggt taactaaatt acactttatt ctataatgga ctttgttgct  11940
atgggcaaca aatgcacata tgcagccatt aaaacaactt gcataaaaat atgagggctt  12000
acaaatagct gagaaaagaa gagaagctaa aggcaaagga gaaaaggaaa gatataccca  12060
tctgaatgca gagttccagc gactatcaag gagagataag aaagccttcc tcagtgatca  12120
atgcaaagaa aacaatagaa taagaaagac tagagatctc ttcaagaaaa ttagagatat  12180
caagggaata tgtcatgcaa agatgggcac aataaagggc agaaatggta tggatctaac  12240
agaagcagca aaagaggtgg caagaataca gagaagaact atataaaaaa gatcttcatg  12300
acccagataa ccacgatgat ggtgtgatca ctcacttaga gccagagatc ctggaatgca  12360
aagtcaagtg ggccttagga agcatcacta tgaacaaagc tagtgtaggc gatggaattc  12420
cagttcagct atttcaaatc ctaagacatg atgctgtgaa agtgctgcac tcaatatgcc  12480
agcaaatttg gaaaactcag tagtggccac aaaactggaa aaggtcagtt ttcattccaa  12540
tcccaaagaa aggcaatgcc aaagaacgct caaactacca cacatttgca ctcattttct  12600
cacacactag caaaggaatg gtcaaaattc tccaagccag gcatcaacag tacaggaatc  12660
aagaacttcc agatgttcca ggagttggtg atggacaggg aggcctggcg tggtgcagtc  12720
tttgagtcat ggggtctcaa agagtccaac acgactgagc gactgaactg aactgtgaat  12780
```

gaagcagggt acaaaatgtt gagagtagca ggaggatttt ttttttcaat tttcttttttt 12840
attgaggtga agctcatgta acataaactt aaccatttta tagtatataa tccagtggca 12900
tttagtatat ttagtccaac catcacctct atctagttat gaaacatttt tattattccc 12960
aaaggaggcc ttagctccat gaagtgtctc tcctcatgcc tcctccccgc agctcttggc 13020
aattactaag gtattttcag tctctatgga cttgcctctt gtggacattt catatcagtc 13080
gaatcacatg ctttgtgtcc tgtgtctgtt atttgtcact gagctccatt cacaccgcag 13140
cctgtgtcag tgctccatcc ttggttatgg ctgaggagca ttctactata aggaggcacc 13200
acactttgtg cctccagctg ctgatgggtt tggttccacc ccccatttca accattctat 13260
gactagagct gctgttaaca tttgggtgtg agcatttgtt tgaacacctg ttgtcagttc 13320
tgtgggcata ccctagttgt ggaattgctg ggtcatatga aaattctatt taaccttttg 13380
aggaatgact agactgtttt ccgcagtggc tacatcattt cacaatccca tcagcaatgt 13440
atgaagattc cattttttttg acatcttcac caacacttat tattcacttt ttaattatta 13500
ttatattcat gctagggggt gtgacacagt acatctggtt ttgatttgca tttccctggt 13560
tcccatcatt tccaaagatg ttgaacatct tttcatgtgg ctcttggcca tttatgtatt 13620
ttctatttta aaatgtctat ttaagtcatt tgcccaactt ttaattgagt tgcttatctt 13680
ttagttgtta agttgtaaaa gttccttata tgttgcagat actagactct tatctgacac 13740
atggattgca aatattttcc cccattttgt gtagtatttt cactttctca agagtgtcca 13800
tgagttcatt tttatagaaa agatacattc tttttcatta aaacaatctg aacatatatt 13860
gtcataaaca caaagtgatt atctctgaat agattgtcaa tgttttgtta ttttggaatt 13920
aaccctggca atatttttca aggttagtaa tttcacaaat tggtaaatgg aaagtgaaag 13980
tttctaattc ttagctcatg ttattatgat gtgtgtgcat cttggaaagg acccaaggtg 14040
tggaacatgc agggatttct gaacactcaa tcctagaggt gggagtgcta tcacagtccc 14100
agacccagct ggtcaggtgg aaagcccccc tgcccagccc acctcagttc ctcgggtcat 14160
catcatcggc attgttttgt ttctgtttct cactctgggg ctgtcctggg aaaaggaaac 14220
cgaaactgaa gctgaattag cctatgtaac tctgacgtgg tttgctcagg ctattaaagg 14280
gctgagctgc cagggctgaa gagagccgag agcagagagg cagccgcagc caaccagtgt 14340
ctgcagagag cctggcacca gaacccacgg ccatggtgag tggtgaggcg ggtttgacag 14400
gtggggctct gtattcccct gcctggtggc atctcccagg ggaagaatgc ctactatgca 14460
caggcaggta gagctactca aagcatccgg ttccctaagt gtgaggggag ggacagggct 14520
ctttctaaaa tcagggtctg ggtcctgaaa ggtggcttct gcccagccgc caactctgag 14580
atccccttggg atcagcacag ggcagggggg tattttattg gagagttgac atgaagattg 14640
tgggtagtag ctcttctgct cccttgcact ctccagtgcc tggggtcccc atctccgtgg 14700
gtgggaaggg tggagaggag ggagctgcat ccccggggtc tgacactcgt cccactgcca 14760
gtgctacacg tgcagtagtc ccaggacttc tgaatctgtg tgatgcccac agggcgggga 14820
cctgacggtg aagatgctag gggccagga gatcctggtg cctctgaggg actccatgac 14880
ggtatccgag ctgaagcagt tcatcgccca gaagatcaat gtgcctgctt tccagcagcg 14940
cctggcccac cttgacagca gggaggtgct gcaggaaggg gtgcccccttg tcctccaggg 15000
cctgagagct ggcagcaccg tcctgctggt ggtgcagaac tgcatctcca tcctggtgag 15060
gaacgacaag ggtcgcagca gcccctatga ggtccagctg aagcagactg tggctgagct 15120
caagcagcag gtgtgccaaa aggagcgtgt acaagcggac cagttctggc tgtcttttga 15180

```
agggaggccc atggatgatg agcacccgct ggaggaatac ggcctcatga aggggtgcac  15240
cgtgttcatg aatctacgtc ttcggggtgg gtagggaagg gccaggaggg ccttagggag  15300
ggctccccat gcagcgcagt gaataaagtt gtagcaaagc caaatgtgaa gtgttcattc  15360
caccctggcc agcaccccat gtcatcagcc ctccattcgg cacccttctg gtgagattgg  15420
gggaagggtg gaggagggag tgggtgaggg gactcagggt cactgagtgg tcaccaggct  15480
agggtggcca agttaaggga caaaccctgt gggatcaaaa tggtgaccct ctggagaaac  15540
tgaagatgtg tccccacctc tttgggaaat taacttctag agaaataaaa agaggcaggt  15600
ctgttgaagc ccatccctgt cttccggttg agcctcagtc agccctgcac aactggtctc  15660
caccttcaca gctgggtcag cagatagcag agggagggaa aaggcctggc tgggtcccaa  15720
aggccacaca gtgagtgtcc ctggaagcgg tgaggggctg agtccctagg gcctgccttg  15780
gccagtggta agggaggttc cccacacca gctggaggct gagggcctcc aggacccatc  15840
agaatacact gtccagcctt cattggtctg gagggaattg gggactgggc cttgggcaca  15900
cacatcacca ttagggtgag ctgctccttc agagttcaca tcatggaagg gccatagcca  15960
gcaggtgagg gggcacccag gatgggggtt cctgttgttc acatggatgg gaggggaaca  16020
aactacacct gcttccacac tagatgcttc tttctgtgcc agtttcccaa gtgagtcagc  16080
cttggacaga atgcggtggg cagggagggg gacacagaac ctatacctct tgggccaaag  16140
tccatgactc tggggacact cagatctcag ctttcggact cttcaggggc atttggctgg  16200
agacccagac cccttctttc tgatctgtgg gagtttgcat ctgagctggg ggacccccag  16260
gtctggcttg cctgtgacac ttatgtagac acgcaggtgt gtgtgtgtgt gtgtgtgtgt  16320
gtgtgtgtgt gtgtgtaggg ggactcctgg ctctagcctc atttcctggg cccccaccct  16380
cacctctttg tcatactgta acttaacaag tgtgagcacg ccctctcggt gacaccctcc  16440
tttcttgaat cccctcagca gggtctgggc gaggtagggt ccttctccaa gatgcctctg  16500
ggctgctcac ccttcatggc ctctggctca gagatctgtg gttggcttgg atgagggggt  16560
gtgcagcaga ctcagccctg gaggaacaga agggatctcc tctcctccca ttcccaccat  16620
cttcagctaa gtcgggctct aatttgcaca ctctggatct cagtttaccc cctggaccca  16680
gcgggaatgg ttggagaagt agcgggaatg gttggagaag agccttgggg gagctgggaa  16740
gggggcgtgg ctggccgtcc atcgctgctg ctattcccac ctcagtcaac agggggagcc  16800
cgcagccctg cagagggccg ggagccgacc cgggatcgcg aggtgggcgg ggctgcgctt  16860
cgctgcgacc aatcgccgca gctcccagcc cgcattggtc cccggtggcc ggtggtcccg  16920
ggcggccgag cttccgtccc cagttcctgt gaggggctag gatcccccgt caggttcctc  16980
tcgccggggg aggggcgcag ccctttaggg cgcgaggggc cgcagggcct cggatctggc  17040
agccccttct tgcggccagg gagcccccgc cgccccagcc ctggcgcagc ctggagcccc  17100
ttggaagtcc cgtcacgtcg tctccagatt atgcattaac ccgatttcag ccgcatttcc  17160
tggcgggggg gcgggggggt ggaacgtccg cgcgaacggg ggaggggcgt ccgtgggagt  17220
gcgccacagc agggagagca ccctcgagcc cgccccaacc ccgcccctcg gcctggccag  17280
gcccaccacc caccttggcc aaacctagac cggccccctc cctcccccag ccaggcctcc  17340
gcccggcgcc gctttcccgg cgctttgttc gcggctgccg cgggtcgcag gacgccggga  17400
gggccggggg cgggcgggcc gggggggtgg ggggtggggg ctggaagggg gtggtgctgc  17460
cccaaggccc gcccccgcac cgcccgcgct cccgccacct cccccgagct gcgtcccgtc  17520
ctgtccagtc cagtccccgg cgcggcccgg tccgtgcgct tgctccggcc gccttccgcc  17580
```

-continued

```
gtcctctgcc cgcgccatgg ccagctttcg gccgttcagc cgggccctgc tgcagccttt  17640
gctgctgctc ctggtggtgg ccgtgcgcgc cctgcccagc gccgacggga cgtgccccga  17700
acgcgcgctg gagcggcgcg aggaggaggc gaacgtggtg ctcaccggca ccgtggagga  17760
gatcctcaac gtggacccgg tgcagcacac atactcgtgc aaggtgggcc ccctggggac  17820
ccccgggacc ctgagcccct tcagaccctt ctagaagccc tggttggggg cccttccccc  17880
gcgatcccgg acccctagcc cggaggtctt cccgtcgcga tgccggccgc gcgctgagac  17940
ccccgtcccg ggacgtggga acgagcccca gacgttccgc agcaccagct ccggctcctg  18000
ctcccttagc gaccgccgac ccccggtggg aggggtgggg ggcgggtgcg ggtctgagaa  18060
aactcgcgag cgccggaggg aaagttcctg cggtgccgct gcagtcccgc tcgcggtgcc  18120
cgggccctgg agacccgata gtgtctgctc cttcacccca aacccactcc cttactggaa  18180
acaagtgcgc cccgcccccc ggagaatgtt cggctaccgc gccccctccc caccggccaa  18240
aggaaagggg acgaggggag gtgacgcttt ctgcttggga tggaggtggt gatttggcct  18300
gtggtcagtg ctgtcgccct ctccgcagag gtgagaatgg gtggtccgga gagagaggag  18360
gggtgcacac ctaatctccc aaccgcgggg gtcctggtgg ggcttgctgc agtgatgggt  18420
gtggggccag agcagagaag tgggcggggc cgttgctgag cctcaagtgc ggggggtgca  18480
gggcaggtgc cccatccgct cctgggagag ctgtatctcc cctggcctta gggagagggg  18540
ccttgcctgg cctctccttc agttgaatct gggagctccc ggggtaggtc tggtggtttt  18600
tttcccacaa tctgttccta gggaggactg aagggaccca ggcccctgcc cctctctggc  18660
ccctaaaacc acctccctga ccagaaatcg gatcattcct cttccttgga gatggggagg  18720
ggtggcagct cctttcagac tggcctgtgc tgactacagc tgggatcccc cgccaggccc  18780
cctcccctcc accacagcca gggcactttg ccaagtccct gcaggatttt cccgacttcc  18840
tccccgctgc tcctgggtgt ggctggggtg gggggaggcg atgaaagccg cccagctctc  18900
ccctgctggt tattggcctt ccagagccta ctctgtatct aggcatgggg ggcgggggaa  18960
gagctggcag ccccaccatc cctgggccac tggagggtgg agggagtccc tgtagatttt  19020
gcagacccaa ggctcccagc aggggtggcc aggtggacgg gccactgttg tctttcactc  19080
ctctttccag aagtcccggc ccccatagat cctgaagaaa ggggtgtttt ttctcaggga  19140
cagcattccc gggcagtccc catgggccta ttcctttagg gcagctcatt ctgcctgcag  19200
tgcctgtggc cctcctgccc ccactgccag tagtctgtgg gcacccccag ggcttggttt  19260
gtctgagcag gtgccctcag ggccccaaga gcagagtgtg gagggtgggg ctgccctgtg  19320
ctgcccaaac ttgattttgt ggttcacagg ctgccttggc agcactcact gtaggagcct  19380
tgcaggagga ggggtctttc acctcctggc tggaccgtgt cttagcccac ccacagggct  19440
gcatggagcc aagctggaca ggagccttga gctcagagcc cgtcaccttg aaacttcatc  19500
atccatgtta gttgctcctg actctttcca gaggtgggcc caagtactgg gtgggttgac  19560
agggagagta aggtgtggaa ggctgtgagg tgtgacattt agaactgggg tggctggggt  19620
catctaaacc tgagggttag ggagctgctt cttgagggaa ggggtgtgtt ctcaggccag  19680
gtatcctgga gtataacaag ggcagtggcg tctgtcatgt gtgtgtgctt ccctgcagct  19740
tcctcctggg gggttggggc actgactcca catatctgcc cagggtttgg gtatactccg  19800
gacatctggc ctgagcaaat gaggtgggaa aagaaggaaa agtccaggca ccagtctggt  19860
gtctgcctct ggcctctgtg gccatctccc ccgctccacc cagttagaag agaaccgccg  19920
acaattgaac aaccccctcat gtccacccta ggttcgggtc tggcggtacc tgaagggcaa  19980
```

agatgtggtg gcccaggaaa gcctgctgga cggaggcaac aaagtggtga ttggcggctt 20040
cggagacccc ctcatctgtg acaaccaggt gtccactgga gacaccagga tcttctttgt 20100
gaaccctgcc ccgccatacc tgtggcccgc ccacaagaat gagctgatgc taaactccag 20160
cctcatgcgc atcaccctgc ggaacctgga ggaggtcgag cactgtgtgg aaggtgtgtg 20220
tggggccgag cagagcaggt gccttggggg cagaagggag cttgtcctag gctagggcac 20280
atggcatctt gtggtccgac ctccttttct gggtcctggc tccctggttt cctggccacc 20340
tcagctccag actcttaaca taagcagcac tccccacct ggccctagtg ttgccactat 20400
ctgtcatctt ggagtctcag acctgcaaag ggataggcct cccattcttc cctccgcctc 20460
cccagctctg cacgcccctt cctggagttc cctgttctag gaaagaggct ggaaccaggt 20520
gaacgaacac cagttgtttg tgttctgcag aagcccgaac acatgtctag acggggccca 20580
gatgttgagc ctttggggtg gggcttaaag attgtgctgg aggggaggct accctgttat 20640
gtgttcccag aggcctgcca tttctgggaa gggacagtta tgtggagtga gctgcttcta 20700
ggagtttgag gggttgtggg atcccctgac agaggtggag catctttcct tgtctgctgt 20760
ccccatgtgt ctattctgaa tggctcaaga gcaaccctcc ctcacatgat ggctcaccca 20820
tccccttcac cccaggagaa tcccagttgg gggctgagat ccttggctga ggaatgtagc 20880
agggagaagt aggaactgcc tgtcgccctc acatcctgtc tgtcccctca tggctgcctg 20940
gggagggatg tatgggagga ggtggagaga tcgcttcctc ccagggcagc aggaagggtc 21000
cctgacttcc tgtcctggga aggcgaccct gtccctgtga cttgctctgt tggccggtag 21060
ggaagttcca tcttctaccc aacttaactc ctgtggtgct ggcttgcttt tgtgggatcc 21120
tggatggtgg actcatctgg cctggggcag actgtgtgtg tgtgtggcga ggtgtggaac 21180
ctgaagtgga gagccctgta gcatcctgct cggcctgcag tcatttgctc ctgggattgc 21240
atctatggtc ctgatgcaac atcgcacaga gatgccagca gggctgtgtc cctggtccct 21300
tcccagcact agcatagctg aggggtccca gcatagccct cccaccaggt gaggactgga 21360
gaccctgact gtgctttgga agctttactc taggggaaat atgggagagt ggcatggaga 21420
ggaggcaggt tgtagggtgt gatccccagt tttggaggat gagttggaga ctaatgagag 21480
gtgggaagag gggtcaggct gcagaaaatc tgtttctgca agatcaagaa gacaagtcat 21540
taactccata gctggaaggg tctagttcga gggtctgtgg ggtcagaggg catgtggcag 21600
gggggccacc ctaggcagaa gagggtctgc catcttgcca ggtcctattc tacccaggcc 21660
aggccctggc tctggatatg tcagcctggg cacaggaccc ctggaaagga gggtctgcag 21720
agagagcccc cagtgagact tcatctgctg tctgctggct accccggata gggaccagtc 21780
taggccccca gctccagctg ggccagtgtg ggcatggtgg tggaggggag gcccccaggg 21840
agggagggac ccagaatgag aagcttgggg tccactgtaa ggctctgggg agccctggaa 21900
gttttgagcc agtgacacgg atcccttctt tggaaggaaa gcagtgccat aaggggcagg 21960
gggccaggga gagggtagat tagatggggt gcctccctct aaggatcccc aaagcctgaa 22020
ggacaaggct cccaggagtt ggtgccaggc ttgaggaaga cacagccctc ttcccacctc 22080
ccacagcagg gagcaggcag gagaagggcc tgcctcccat tctgtaagcg atacctccca 22140
ttctgtaaga gataaagacc tctgacccca ccccaggctc tccagggagc caagcctcac 22200
cttagcatgg ggggtagggt tagggatggg ccgagcttga gctacaatga cctctcatct 22260
gaccctgacc cttttctctt ccttggggcc ccatagctgc ccccgtccct cagggccccg 22320
agtgaaggct gtgaagctac tgattgtgga ggtcacccca agacctgtgt ctctatcaca 22380

-continued aatgtcccct gcccctaaaa ggcccacagg agccaaggtc aggggacaca tcctggaggc 22440
ccaccccct agatgcccc acctcatccc cacctggacc ctgcttcctg caggggtacc 22500
tgttgctggg aggcatacct ggtccccagc tccactgggc tcgccttcct cagtttctcc 22560
cttagggcct gcagggtctt cctggctctg ggccccttcc ccaacctcca gtccccagga 22620
agctcctccc caatcctctg cctggggagc cacattccga gcataactga gacaggtatg 22680
tgtccctccc tctgcaccac ttgtgggtga aggagactgc gggtttgctc caggaaggaa 22740
ggagaccctc acgccctgct ttgtcaggga agtggcctgg cctcttccag tgccagctgc 22800
ccacgcatca tgagctgccc aggctggcag ctgagcgggc atctcctcca gcctttggcc 22860
actataccct ggtctggact tgtacacttg tacactccca ccaccctcct ctcccccacc 22920
taataaagac tggtccttgg gcccccctga attccctagg agggatgcag gcttggggtc 22980
cttccccagg cctttccctc ccgaactccg agccaagagc agagaaagga agtgttgtct 23040
gccctctccg ggcctggcac aggaacaggg tcggagagtc tggcattagt ccagcccagc 23100
cctgcccagt cctgaagccg ggggtcctgg tggccacagc ctagactggc ctgcctgatt 23160
ccagtgagca ccctcccttc ctccctgcca cgctagcctt tgggccttca cgccagtctt 23220
gggcctttgg ggaaggtagt cctaggctat atctcaggct agagagatgc tgggtcccgg 23280
gccgccggcc ttggccttgg tgcaggccct gtggcctggg agccggatgt ggacacagac 23340
acccccagac agggactggc tccgcagagc aaagcggggc aggtaggagc ccagggcagg 23400
ttccagggct ggcttcctca gggctagagc tggctccctc tgctgtctgg catttagctt 23460
ctgtaccccc aagtcctgag cccgccctac tcccccacat tcctccctgc cgaggggggga 23520
ggtggcttct tcctgtccct gtttccctct tccagacgta agttctcacc ccaccccctc 23580
cagacccgcc ccagtgccgt cctcagcccc tcccccaggc aggtccttgg agctggggca 23640
ggcccaggct ggaggctgcg cgcctgggct ttctccttcc ttccagccac tgggggcggg 23700
gcatctgctc aggtggagcg tggcctgctc ctgcactgtc ctctctcacc tagggtcccc 23760
ggtaggaagt ctccgagagc atgggcttgt gggaccacag cgggctggct gataccctca 23820
ctggggcggc cccaggagct tggggcgtgg tggggggtgg ggagggggtt gctgctgaaa 23880
tcaaagggca ttggatccat cacttcaagg cagtgcgctc ctttcccgca ggcctgagct 23940
ggtggaaaca gctcctgact ttttccagac cccaccccat caccctgctc cccacccaga 24000
gaagagcccc cgcctccata ctccccagca gattggaaat ggaaaaaaaa aaaagttgtt 24060
ttgaaactgt cctctcccct gctgtctgta cctgccttcc gcagggctct ggacagagta 24120
gattccagtg gggcctgcct gtggaaggaa ggcagagcca tggaggtgct cgcagcctct 24180
ctggggtgct gggaagaact ggatcgcctg gtcagggcta gctggtctgg atctggggct 24240
ctagcccccct gccccaccaa tcctttcaga ctgaggtagg gagagtgcag agggtgggat 24300
ggggctgccc caggtaaggt tagcagggc gtgagcccag acttcagggt tgtagatcta 24360
gccaactgtt gcttgccctg cacagcctcc tccagcctgt tttgcttcct tcttaaaggg 24420
ttaatccccc aatcccctga gaatcaaagc ctgcccccac cccatcacca cagtggggtg 24480
gaagacagct gctgaaattg acctctctcc tgcccctgcc ccccaagtcc tttgccttca 24540
ccagaaggcc caggccagct gccctccctc ccagcccaga ggcctgaact gctctgctgg 24600
ccccagcaac cccctcagca ttgggatagg ggaactgtgg ctccccacac aggcccctga 24660
ggcccagccc agcaagctgg gggctgcagg cacaatccct gaagtagccc caatagcact 24720
taacactcca gagtcccagg aagcgcccac ctctcacaaa gagaaaaagg gatctcagaa 24780

-continued

```
atgagagtta gtgacagcta ccctgatgag attgacccag ctcatcagag agtactgtgt  24840
ccccataggc tacaggggc tcaggaggga tctgggccct attctaggct gtggctggga  24900
accggggagg ggtgacctgg cctctggtgg agcttccaat ggggagggaa gctcccctca  24960
aaggggcctc tccctccaga gcagatcctg agaacttcct ctgaggaagg ccccctgcta  25020
ggggctgctt acagctggac ctgggaaggg gaagatggtc cctcccacct cccctcccac  25080
tgaggcatgg gaggggcaag ctctctttcc tcacaggcag ccggctgttt ccagctgtgt  25140
ggcctgcaca tgtgtgtgtg tgtacatttg tatgcacgtg tgcctgcaac ctcaggtgta  25200
ccaaccacca cacaacagtt ctggttgaaa ctccagctgg tggcctgtgg ttcctgccac  25260
ccttgtatcg caggactcag cctggggagg ggaccctgca gatgctctgc caatgggatg  25320
gtagccggca accttggctt gtgtcccaga gttctgggaa cagggctgtg ggccctctgt  25380
gggtgccgtc tcctgcctgc tgccccagtg tccagctgtg ctcccctccc accaccccat  25440
ccccggcaga gagctgggcc cctgctcctg tgggctctgc cgctgggttt ctcaatgcca  25500
gagatggaag ggctgcattg aacaggaaga gtccctggga tcacttgggt tccctgtccc  25560
ctcacgcctg ctggaccctg tgtctggcta agttagggag cagggcaggt caggagaggt  25620
gggtctgcct ttgatgtgag gtgggcctga agctccctac ctctcctctt agcaacttcc  25680
tctgcactgc cccctctgca taccaggccc agaagcaggc aacctgttgt ggctccctga  25740
ggcacctgtc cctctggcaa caggtacatg atttctatgt acattgggga gaaataaagg  25800
cacaacatct gggccagatt atggcctgtc ctgacccaca agtggggaaa ggatgtatgt  25860
ccacccctgt tcctagaggg ggggaagtga agcttgctag agtccactcg tgaatccagc  25920
catcagttcc ttcctcaccc acccgtccac gcaggaccta gcagcaggcc ctcacaggac  25980
cactagaagg gctgctgcag ctacccacgc ggctctctcc tgtctggtcg gtctttctgt  26040
ccctttgttc ccagcttctc ttggttccaa tgttgtagcc atgcgttctg ggaaacacac  26100
tcactcagaa gcacaatgca aataacggag tgcagtttat tacaccggcg ggcccaaggc  26160
agagtctcct cttagccaag gaccccgacc agtttttctg aaaaccttat ataccctaag  26220
tgtacgtgcc caaacccacc tccccaaatt ccctgaaact agtctgaaca gaggaaaaga  26280
aagatacagt caaagttaac ctgtgattca tatgccttaa gcctaggtag ttaacagtgg  26340
accattatta ataggcctgt gatcataccc caataagcat aatagaattt atgattctat  26400
gcggttacac agataattag ggtattcttt aggtaacaga gagtctagga acgagccctg  26460
gggctcttcc atccggaggg gtctggtttt ccagttggtg tgtcgtttcc atagatactg  26520
ggcatatagc tcaaagtcca cagtccggcc caagatggag tcctgctttc aagatggagc  26580
ctggtctgtc tgtttcctcc ttcatccctc ctcttcatgc tcttaactca tagtatgagc  26640
atcattcata gggatttatt gcaccctgac tctccgacct ccaatttggg agaacgacat  26700
caacctttgg gttacagagt tcataataca ttgtaaaata aagggtccac aaagcagaac  26760
tatgaaggca actataacaa tggtaaatat agttttccac caatcaccct tcacccaaca  26820
taggaccgaa gtccaaaaag gaagatgtat cagacataac ttttacctga cctttcatgt  26880
catctagggt agctgatcta tagccagata aatcaggaat atacacacaa cattcaactt  26940
taattatagc acaggtccct ctttgtactg aaactgtggt caatctcaag atgatagcag  27000
caagtccttg tagcagcagt tgattgtaga gcttcatctc tgtttcttct ttaagatgat  27060
cttggtttca tggggatcag aggggtccct ctgcacagtc cactcggcgt cctccgggtc  27120
tgcatggtat gctctcttca gcctcatgtg gaggatccag ggagtgacac ctgcaacttt  27180
```

-continued aactgcagta gggctggtta gaacaacagc atatggaccc ttccaatgtg gggccaagga 27240
gtcgtgtttc cagtccttga ccacacccga tccctgggca caaattcgtg aatctgttcc 27300
ccaaggggga acggcacctt ttcttgtaca aacttagtta cctgatttat taccttaccc 27360
agttgttcca tctgctgtga aatctcatct ccccttacct gaggcaaatt tgttgacacc 27420
tgttttatta tgggaggggg cctcccatac acaattttgt acagagacga ttcatgggac 27480
tgtggggtca tcctgagtct gagcagaccc gtcagaaaca agtccaccca ggaaccgtca 27540
gtctccaaga tccacttgga gagtgtctct aagtgtccgg ctggttcctt ccaccatccc 27600
agaactctgg ggcctatatg ctgtatgtaa tttccacttg atgtttaaag ttttgcttac 27660
ttggttatac taaaacagct acaaaagccg ggccattgtc cgatccaatg ctggtaggaa 27720
atccaaatct gggaactatc tccctaagca ggcaccgggc tacttttgat gctctttcag 27780
tgagggtagg aaaagcttct acccatcctg agaacgtaca tactgtgacc agcaggtaat 27840
ggtagtgtcc gtgaggtttc atttcaggga agtccacttc caggtgttca aagggcagcg 27900
tgccttttac ctgaatccct gcaggtttct gtctgtgcca acaggcagca ttggcctgta 27960
agcaggcagt gcagttctga gattttgtcc tgcatgggga agagaggagg ggaacaaaga 28020
aatagtttca aattatctct tccagtttat catggcatag atgggtcgct tggtgtgttt 28080
ggcttaccag agtgggtgcc agctcctccg gtacccataa tttgccactt ggcaattccc 28140
actatccctt ttcagtcttg atggcccctt ctgctttggc tagttggttt tgagcttcag 28200
tgtattttgg agagtctagt gttagctcag gtagctccgc caatatgaaa gctttaacag 28260
gggcttcact tgtcaccccc aagcccttgg ctgcttgttt agcggtctta tctgccagtc 28320
tgttccctga gcccggggag tatcctcttt ttgacgttct cagcagtgta tgactgcaat 28380
cctttctggt tcccaggcag catctaatag ggtcttaatt tcttccttat tttttatctt 28440
tttcactagc tgtcaaaggc ctctctcctt atacagagcc ctgtagtgtg gcaaaagcat 28500
acctggagtc tgtgtcaagg tttgtcttct taccttttga cagctggagg gcctggatta 28560
gagcatatag ttcagcctgt tgaatggagc agtgtggtgg cagagaggga gcctcaacaa 28620
tggtttcttc tgtgaccact gcatatcctg acagtcattg tccttgtttc accaggctgg 28680
tgctattggt gtacacgacc gaatctgggt ccgggattgg ctggtctctc aagtcaggtc 28740
tgctggcata tttccttgcg atcatgtgag ggcccacctt ctcccacagg aaggagagtg 28800
gccagattca gggcctgaca aggctcagta gtaacatggg ggttctcaca taacagtccc 28860
tggtactgag taatctggga tgttgacagc catttatgga ggtccccttg caggagagtg 28920
ttgacctcat gtgggacttt tacaaacaaa tcttggccca aagtcagctt ggttgcatcc 28980
tggaccagta aggcaactgc ctgtaagcat cccagccacc cagtagcaac actgtccagc 29040
tgattagagg taagtcacag gtctgtccca tgtccccata gtctgggaca acactcctat 29100
agccaccttg tccttttcag tcatgtaaag agtaaatggc ttagcaaggt ctggcaggcc 29160
caaggcgggt gctgatgtaa ctgtactggg tttgagtttt attaccactg ggacttgttt 29220
tgcaagcctg ggggggttgt cttctgccca gacctcaggg aattgttgag ttaactctct 29280
ctcttgacca ttgagcctgt ccggtttccc ttctgggaga tcgtgcaatc tcccttcatc 29340
ttgaggggtt actgagagga agagtaaata ggtggttaag cccactcgaa cagtgggtct 29400
ttcttgggga gacagtgact tgttccccca atttagacag caagtctctt cctaacaaag 29460
gtactgggca ttcagggatg tataaaaact catgagtcac ttggtgtccc cccatctgac 29520
attttcaggg taggctagag acacaaggct gcatttatca ccatctgaga cccagcagcc 29580

-continued tctggctggg tctattggcg tataaagtct ataggcctcg catagtcttt cgcagaactc 29640
agggtgattc gctttccctt tgaatcactt cagagggttt tgtgatactt atagcttttc 29700
gggcccccct cttgagacct tgtaaaatag ccacccgata actctccagg tggcccctcc 29760
cttcctctgt gttacagtcc cagttgggcc tctcatccgg ggtggctagt tctgcccacc 29820
gctgcgggtt tgcggtaccc tcaggtgcca tttcggagaa ggcaatggca ccccactcca 29880
gtactcttgc ctggaaaatc ccatggacgg aggagcctgg tgggctacag tccatggggt 29940
cgctaagagt cggacacgac tgagcgactt cactttcact tttcactttc atgcattgga 30000
gaaggaaatg gcaacccact ccagtgttct tgcctgcaga atcccaggga cgggggagcc 30060
tggtgggctg ccgtctctgg ggtcgcacag agttggacac gactgaagcg acttagcagc 30120
agtagcagca gcagcaggtg ctatttttct taaccatttt ctggcctcag ttaggatcct 30180
gtgtctttcc tcagtgctga aaagggagac tagtagttgg attatgtcat cctatgtagg 30240
gcggtgggtt cgaaaaatag tctctaatag cctaatcacg gcttgtgctc cccggagtat 30300
ggtggagtgt gtctctgcca gtttaatata ttcgtagagg aaaatggcta gtaataatag 30360
gctacagggg ctgatggtag tgccccatgt gtcctgaact ggaggctgtt gtagctttct 30420
aaggggcatc tgtagtgggg ttctttcccc ctgttccttg gtggagtgca gcctctgtct 30480
aattgctgtg ttttgttccc ccttcccatc agtactcacc gggagaggtg gatacaatct 30540
aggaggtcca gctgaggtgg aattctgggg acattgacca gaggtctcca ttgctgggat 30600
tggagcctgc cgaaacggca gctctacgaa ctccgggaga gctggtggaa gagcagtggc 30660
tgctgcagga acttcacctg gccctggatg ggcagtaag gtggcctccg gtcctggtgg 30720
agcactggga ggcaggcgtg tcattatcca gtatgggga ggggtcaggt catttccgtc 30780
caaatcctgt aaaatttcct tttttatcat cagtcaattt ttgtgccatt aatattttcc 30840
cctttccctt ctggatacag aaccttgtcc aagtaggagg gtcttgagct aaccctagcc 30900
atgagtcaat atatggatat tgatccaggt gtccgggctc tcctgtgatt actgtataga 30960
cggcttccac tatttttaag ttcatggtgt tctctggtgg ccatcctact cccatagggg 31020
gccattcgac ctcacagagt atgtggaggc ggttaggctt catcttcacc ccgttcagtt 31080
cagttcagtt gctcagtcgt gtccaactct ttgcgacccc atgaattgca gcatgccagg 31140
cctccctgtc catcaccaac tcctggagtt cactcaaact cacctccatc aagttggtga 31200
tgccatccag ccatctcatc ctctgtcatc cccttctcct cctgccccca gtccctccca 31260
gcatcagagt cttttccagt gagtgaactc tttgcatgag gtggccagtc tcctccaaat 31320
cccttcttta aatttttaat catgcactcc aatacagttg ccttagattc acttcccctc 31380
atcttgctta ccttctcgga ccttctactt ttcctttcgt tctgtctacg aagttctcag 31440
taccctatgt acttctgata tttccactca atgacactta aattgccatt ctgccacctt 31500
cctaataggg gtgagaaaag ccttacctgc cagatcccag agggagaagg gggattggca 31560
tgtcttcacc tgccggtcag cacaaccaaa ccagaccacc acgtgatcca agattgtttc 31620
tcccttaact tttaaagtcc attctgcctc ggtgggcttg atcaggtgcg gatgaaaata 31680
cagatgggtt aaatatccca tgtcccaggc catctctgga aaagccaatt cgtactcact 31740
tatgtatccc cctcctatcc tgagaattcc gagggggtca agaatttcat agcagatggg 31800
acatctcctt ggggagggca gaatacgagc acacagaaac caagtttctt ctcctaaaaa 31860
tcccctggca attgcttggt aataattttc cccaagatgg catggacacc acctcctaaa 31920
tgaccttcac aagtttcctt cctaagccct aacacactca tcaacctgtg taccaagcaa 31980

-continued

```
tcgttgccac ctgcctattc caggctcctg tgggtctgtg ccccttctag tccctcccag  32040
ggcggtgatc aggccccctc ttccaccttg ctgggtgggt tcctcctcac ctgagcactc  32100
agttcccctg ctgccatcca ctacctgcta acatgaaagg tccgggcatt gagaagcaga  32160
atccttccag aagggcgagg tgccttcccc cctctagaag atttgagcca caaggcctca  32220
gagtagtccc aaatgggact tgtctcctca aagtgaggag tttcccggcc aacgcaccaa  32280
atgttgtagc cacacgttct gggaaacaaa ctcactcaga aggacaatgc agatagtgga  32340
gtgcagttta ttacaccagc gggcccaagg cagagtctcc tcttagccaa ggaccccgac  32400
cagtttttct gaaaacctta tataccctgg gtcgggaaga tcccctggag aaggaaatgg  32460
caacccactc cagtactctt gcctggagaa ttccatggag ggaggatcct ggtaggctac  32520
agtccatagg gtcgcaaaga gtcagacaca actgagcgac ttcactatat accctaagtg  32580
tatgtgccca aacccacctc ctcaaattcc ctgaaactag tctgaacaaa ggaaaagaaa  32640
gatacaatca aagttaaccc ttgattcata tgccttaagc ctaggtagtt aacagtggac  32700
aattatcaat agccctgtgg cataccccaa taagcataat agaatttatg attttatttg  32760
gttacacaga taattagggt attttaggta acagagagtc taggaacgag ccctgggact  32820
cttccatccg gggggtctgg ttttccagtt ggtgtgtcgt ttccatagat actgggcata  32880
tagctcagag tccacagtcc agcccaagat ggagtcctgc tttcaagatg gagcctggtc  32940
tgtctgtttc ctccttcacc aataggtgtc tgtctgccac tcctcttcat cttgacatcc  33000
agctggtcaa tacctccaag aagcaccgcc ccccaactca gacctttgtg ctggactgtg  33060
catctctctt ggcctggcca tggccctcag caggaataca gggtctcctg actcaccggc  33120
actgaccaca cctgggtgcc accctggctc ctccagcttt ctgtttcctc ctagacatgg  33180
gcaggacctg gccgaaagag atggatttgg ggctgtccta gaggggaggg acagaaggta  33240
tggatcagct agctccaccc catcccctac ctcaggggtc cccaaccctg aggccatgga  33300
ccgctactgg tcagtggcct gttaggattc agaccacaca gcaagaggtg aggggtcgga  33360
gtgctggtga acaagcgaaa tttcatctgt gtttacagct gctccccatt ttggcattac  33420
cagctgagct ttgcctcctg tgagatcagt ggcggcataa tgaacgtaat gcgtctgaat  33480
catccccaag cctctcccca cccaactcca aattcgtgga aaaactgtct tccacaaaac  33540
tggtctctgg taccaaaaag gttggggaca gctgccctac ctttgatttc cctggtggct  33600
cagacgtatc tgcctacaat gtggcagtcc tgggttcgat ccctgggtcg ggaagatccc  33660
ctggagaagg aaatggcaac ccattccagt acccttgcct ggagaatccc atggatggag  33720
gagcctggtg ggctctacct tttctccagg tgtctactac cccctcctct gttcggctgg  33780
cgccccctgg tggctgaagc ctgtcttggc aggcgtcccg gccctgggtt ccccaggcct  33840
gcgggtctgg ccttggccct tgtttccctg agacctcacc aggctggctt ctcctggtct  33900
cgtgcagtct cctgagcttg tttttactgg gcctctgtag ttggctctgc ctggatgtgc  33960
aaatccctcg accccatcct tcgggtctct gtacagtcat cccccacgta gatgctgcga  34020
tctagggcaa tctctgctac agggtaacct tccaggggca aagagctcac ccgactcggc  34080
acctgcctcc tgcactgagc ccacccccgg aggagtttgg ccggggccgg gcaggatgaa  34140
tgctgagtaa tgaaggagga ggggtgccgg ggtcagcggc cgctgccctg cgacccagcc  34200
ccaattcttc cacaagctct cacttaatgc cacctcccga cagcgcgggc taaccagcag  34260
tgtgggccct gcccggggct cgtgggtggg catacagccc gcggactcaa gtgggcccct  34320
cccggcctta gcctcacctg agggggcgat cggggccggg ctgcacgccg cctccttccc  34380
```

-continued agcggttggc cccagtccaa cagcgacgtc ccgctgtgaa acgcccattg tctgctgagg 34440
ccgaggggga ggggatggcc ctgagacccg actctaggag gctgggggag ggggccgccc 34500
tgccccatcc tcttcccctc ccccgccagg gcggccagac acctgtggct ggaggccgcc 34560
tggcactcga ctgttggata cactttacac actagcgggg taccctcgag ggcccaggag 34620
tggagactgg cggaggtccc cacagcaaag gtgtgtgcgc atgcgtagag tgtgtctgct 34680
gccgggaggg cggtgccacc ccactcccac cccatccttt tggagcgcgc cggcccctcc 34740
cctacagagc gaaagggatc agagggaggc cagtaggtgg gacttcatat tctctgtgga 34800
cttcgttccc ggtcttcctc gcagggcaag ggaagcgtct ggagggggccc aaccacacgc 34860 gtgtatgtgg gggtacaccc gatgtgtgct gtgtggatga ggggcaaatt ttgcattgca 34920
tgaaggtgtg cagtgtgtat gcacacaggt gtgtgtgtga ctgcacagtg cctgtgcaga 34980
cttgagtgag tggttgtacg tatgtccgca tatgggagac ctggaacatg gagtg 35035

<210> SEQ ID NO 2
<211> LENGTH: 809
<212> TYPE: DNA
<213> ORGANISM: Bos taurus

<400> SEQUENCE: 2
aagcagcagc caagaaagta gaactcacaa aaaatgaagg ataattgtta catttctgtt 60
tgttatttca aagaagcacg tggaggaaag agggctaagc ttattttcgt gtttgatgtt 120
gttttcactt tgaattccct tgtggggcac aatcatgttt tgagttttgg ggatgccagc 180
ccatggtggc ctgggcagtc ttgtctgcat cccacaaacc tctctggagg ctcactgtag 240
gcctgactgt tcttggggct ggggaggcct ctcctgaact ctgaactgat gtgggaggaa 300
aaggcaaatg agcaaaataa ataatgacat ggtttccaga gacagaaaga aatgtgtagg 360
ttttgggggg agccgaaagc cttctttcca ctgagtggtc tggatggtat ttttgcagtg 420
agctctgctg gagaaggcaa tggcacccca ctccagtact cttgcctgga aaatcccatg 480
gacggaggag cctggtgggc tacagtccat ggggtcgcta agagtcggac acgactgagc 540
gacttcactt tcacttttca ctttcatgca ttggagaagg aaatggcaac ccactccagt 600
gttcttgcct gcagaatccc agggacgggg gagcctggtg ggctgccgtc tctggggtcg 660
cacagagttg gacacgactg aagcgactta gcagcagtag cagcagcagc aggtgctatt 720
tttcttaacc attttctggc ctcagttagg atcctgtgtc tttcctcagt gctgaaaagg 780
gagactagta gttggattat gtcatccta 809

<210> SEQ ID NO 3
<211> LENGTH: 23347
<212> TYPE: DNA
<213> ORGANISM: Bos taurus

<400> SEQUENCE: 3
acccactcca gtacactcgc ctggaaaatc ccatggatgg aggaacctgg taggctgcag 60
tccatggggt cattgagagt tggacaagac tgagcgactt cactttcact tttcactttc 120
atccattgga gaaggaaatg gcaacccact ccagtgttct tgcctggaga atcctaggga 180
cgggggaacc tagcaggcgg ccatttatgg agtcgcacag agtcggacat gactgaatcg 240
acttagcagc agctagttgc aagtccagag gaggaagtgg cattcccaga atggaaagga 300
accacagggc caagggagga ggggccggga caggtgggaa ccaggctcta gtggcttcag 360
gtccccagag ggtctaaga gagtcatgct tggcttttct gagcagcaga gtggcccaac 420

-continued

```
tggcagctcg gaagggccac ctcccacact acattctacc tggtgggtgg cgatgctggc    480
tggcccccac ctcaataccc tttcccaggg gtccagtctg gggcccagtg cagacgcctg    540
tgatgcaggt ttgatcactg ggtgggggaa gacaccctgc cccctccccg gaggaggaaa    600
tggcaaccca ctccagtatt cttgcctggg aaatcttatg gacagcctgg agggctacag    660
ccaaaagggt cacaaagagt cagacacaac tgagcaactg aaggaaggac cctcctgtac    720
ctgtttcctc acctgtaaaa tgggctacct tttcatttag ccctggacta tagtccatgg    780
ggtcgcaaag agtcgaacat gactgagcaa ctaacacttt cacactttga ctgagaagat    840
aaatgagatc tgattttgaa agcacccagc acatgcaagc gggacagagt cacctggatt    900
cacctctgcc acaagcccca ctgtatcctc taccctctga gacaccctct ccctacctgg    960
ggtcttcaga agcctgtttc ttggcccttc cagccccaac aaggagcctt ctctcaccca   1020
gagcagagtg agtcccaggg gtgtcatcta catccctgtg tccttcccac tgggctgcac   1080
ccccactctc tctctgggcc ctcctacctc tggctgtccc ctccctgcct tttacatctg   1140
gatttgatct ctggtaggac ctgggactcc tggggaccgt aggggctccc ttgctctgag   1200
tagagaggga gagtcctagg ctgcaggggg gaaactgtgc tgagaaatac tgacgtggaa   1260
cactgcattt tccaaagatg gctacaatac atccacccca aatactctac ctgtgtgtcc   1320
ttggtgagat tttgtgatga cattaaccag caaagacagg ggcagtggtg atctatgaat   1380
tctgaggctt gacttgaaaa acgtgcacct tgctgtcctg ggaaactcac tcctggaaac   1440
cactgacccc tctgtgagga aacccgaact ggtctcatgg aaaggcctca tggagaggcc   1500
ttgtataagt gttgagctag gaacctagaa atctcagctt ccagacaggt gatcccaacc   1560
tgccgcttca gagcccccac tcacactttc ccagccagct ctgtgtgctc tgttccactc   1620
ttgattcaca tgactggtgt tactgtgaca ctttggggtc attcgttacg aaacaatagt   1680
aactggaaca gctaagatgg cccaagccct ggacccaccc ccctccccag ccccaccccc   1740
caaaccttgt tccttccttt ctctggcatt cacagagtca caggagcttc ccgcactggc   1800
tgtccatctg acgaggtgac ttttgcagct atccaaggcc aactatctgt cctcctagat   1860
ccaggcttga gttggccaag tcccagtagg ctgatggtcc caggggcatc tctagggacc   1920
actgttggcc actgggcagg aaaagtagtg ggggagtctg tgtgggaaga taagtgtatt   1980
ttccagtcca gacactgggc tgcagccttg gtggggggtg gggggatggt ctttctcacg   2040
tctggctccc atgacagcat tccacaacat tcagacagtg tccctccggg gcctgccagg   2100
tgctgtctgt gcacaggccc ctcccaacct ctgacagggg ggtggcacct gcacttgcac   2160
cctgcccctc agcattccac aggcacatgg gtccctgaat atcagagaca ccatagacca   2220
tgaccagcaa ccccatcctc ctgttccctc ctcttctgcc aagggacaac aggctgtgga   2280
ctcaggcagc caggaccaga gttgccatgt gaccaggcta gagtcattgc agggtctctc   2340
ctggagcatg ggagttgggt cctgagatga taaagtggca gaggctaggg ctggaggaac   2400
ccaggattca gtatagagaa gaaggaagca gatgaccagg accctaatct taaccctgag   2460
ggggcatctt tcatttttac aggccagcgg accaagacac cttccttcgg ctcttggtgc   2520
tgggcagttg gagcatcccc ccaacacctg atgcatgaca gcacctcccc cgaggtctgg   2580
gcattgtcaa catctttctc cattattgaa tgttgacacc tctccacgct ggggaagcca   2640
tgtctcccca attctgtgtg gtaacagagc ttcccaccct gtctgcctgt gatgccacct   2700
ccctgtgggc ttccatgggt gcttctctct ccagtctcct tggaccacta ctctctggag   2760
aggtatgctt tgctctcctg ctggtcacat ccagactagt ttcttcttca ccaaaaaaag   2820
```

-continued

```
tcccagcttt gaacctcatc ttattaacag atctcatctt gtgaagtcca ctgcaaccct   2880
gcgggggggg ggcctcccca taccttctga aggttcactc ctgattccct gtcactttct   2940
ccagcggctc ctgtcacagt ccttgttgac ttccaaattc acacggttga tcttctggac   3000
ttcctggcct ccatggggca tcctagtgta gagttggcaa ctaagcttcc aatcctaagt   3060
gctgggtgta gactgtagcc gtaatattcc catccaccct ggaggacacg cccaccagga   3120
agccccgccc acagggcaca ggtcagcatc tgcagtacaa tatcctgctg ctttcccagt   3180
gtaacctggg gtcctgcctc ctccctccac actctcagcc tcttgtctca ggttctgcct   3240
cccgcttctc cttgtgcctt tcagtcctgt ggaacttggg gaacaagtct tcactctaat   3300
ctttctatcc acacaactgg agcactctct gcccagtggt ggagcctgac tgaggcacca   3360
gcctcctctg aatctgacta ttctcagttc tcagaccaga ttctgccatc gtcctcgacc   3420
ctcagagttc actcccagtg ctgctctggc aggtcctaca gtggctctat ctccctgatg   3480
tatacaaaca cctacttctg acctattgct tttccaccac tggctgcaag ccgccaccag   3540
cttcggcctg gaattttgta gttctttgcc atggcaaggc agccagtctt ggagccgagt   3600
gctcaatggg ggcaggtgga caggagagga gattagaggg tcagcagagt ggtcagaaga   3660
acaagcctaa gctcctatct tctctcggaa gcttatggga agccatggga gagaaggttg   3720
tgtgtagatc actctggccc ttggctccac cacagattat ggggtcagga tagaagcaca   3780
gccactcggc tgtatccata gcagcctcag tggacgaggg cgcatagata taagtgaggt   3840
catggatatt cttgggagtt ttttgttgtt gctactgctg ttagatggct gaagggctta   3900
aaaataaaag caagtgtatt aaacgatata gatactgttt taaaagtttt aggaagttta   3960
agttagtttg taaatgaaac caaatattaa ccaaagaccc ctttataagt agccattgta   4020
acttcataaa taggatattc aggtttttgt ctagaacata tgtattttgt gatcatgttg   4080
ttaggtgcat acaaattaaa aataatttca ttttatcagt gagctcaacc ttttattgtt   4140
atgcaacctt ctgtatctag taatgctttg actataaggt ttctttgtta atctgttagt   4200
gaaactgtta atacggtcac atctgcttcc ctttagttaa cattacgcag taggtttctt   4260
ttctcctttt actttcagtt tcctgtacct ttatatttca tattatttat gtcttctgta   4320
agctgtgtaa aatcagatta tttttaatca ggctgacaat cctggtcatt tagtcccccct   4380
ggatttcaga cctctgctct ttagaactgt gagggaatac atttctgttg ttttaagcca   4440
cccagtttgt ggtggcttaa aagcctccaa gacacagaga catgcttcca gggctatcgt   4500
tttgcctgcc gaaagccttt gcatctagtt cctcttgtcc aaagcaggtg atattcaata   4560
aagtaataaa agaaaataaa ggttctatta ctatatatac catatttttg ttatcttttt   4620
aaaatttttt attacttaaa attttttttga attgttgttt cattccctta tctttgtgcc   4680
atatttaata atggtcacct agggactttc ctggtggtcc agtggttaag acttagtgct   4740
tccaatgcaa ggggcatggg tttgacccct aatcagggaa ctaagatcct gctggctgca   4800
tgccatgccc gaaaaaaaca aaacaaaaca aaacaaaaaa cagaatcaaa ataatggttt   4860
tttgaagaag acagggattt tcacattctg taatatttgt tttgtttgtg gctttctttt   4920
tataatacta atattattta tgcaaggaat gagtcaagtt agaaatttag aataatataa   4980
acaatattta aactgtttta tgcatgttaa caactttggt gccttatgat tatttggggg   5040
gaattgatgg aatgattaat tcatatgaaa acaatttggt tttccccatt ccttttattt   5100
atttaaaatt tgtttattta gtttaaaatt tatttttaaa atatttaatt atttttaggt   5160
atttattttt attttattta tttattttgg ctccatcttg tgggatctta gtttcccaac   5220
```

-continued

```
cagggatgga acctgtgctc ctgaagtgaa agtatgaagt cctaaccact ggactgccag   5280

ggaattccct aagtatttat ttttattttt agctaacata tgcctgagat gtgctgtttg   5340

taatagtaaa aatgtgggaa caaccaatat ttatttaaaa atatgagact ggttaactaa   5400

attacacttt attctataat ggactttgtt gctatgggca acaaatgcac atatgcagcc   5460

attaaaacaa cttgcataaa aatatgaggg cttacaaata gctgagaaaa gaagagaagc   5520

taaaggcaaa ggagaaaagg aaagatatac ccatctgaat gcagagttcc agcgactatc   5580

aaggagagat aagaaagcct tcctcagtga tcaatgcaaa gaaaacaata gaataagaaa   5640

gactagagat ctcttcaaga aaattagaga tatcaaggga atatgtcatg caaagatggg   5700

cacaataaag ggcagaaatg gtatggatct aacagaagca gcaaaagagg tggcaagaat   5760

acagagaaga actatataaa aaagatcttc atgacccaga taaccacgat gatggtgtga   5820

tcactcactt agagccagag atcctggaat gcaaagtcaa gtgggcctta ggaagcatca   5880

ctatgaacaa agctagtgta ggcgatggaa ttccagttca gctatttcaa atcctaagac   5940

atgatgctgt gaaagtgctg cactcaatat gccagcaaat ttggaaaact cagtagtggc   6000

cacaaaactg gaaaaggtca gttttcattc caatcccaaa gaaaggcaat gccaaagaac   6060

gctcaaacta ccacacattt gcactcattt tctcacacac tagcaaagga atggtcaaaa   6120

ttctccaagc caggcatcaa cagtacagga atcaagaact tccagatgtt ccaggagttg   6180

gtgatggaca gggaggcctg gcgtggtgca gtctttgagt catggggtct caaagagtcc   6240

aacacgactg agcgactgaa ctgaactgtg aatgaagcag ggtacaaaat gttgagagta   6300

gcaggaggat tttttttttc aattttcttt tttattgagg tgaagctcat gtaacataaa   6360

cttaaccatt ttatagtata taatccagtg gcatttagta tatttagtcc aaccatcacc   6420

tctatctagt tatgaaacat ttttattatt cccaaaggag gccttagctc catgaagtgt   6480

ctctcctcat gcctcctccc cgcagctctt ggcaattact aaggtatttt cagtctctat   6540

ggacttgcct cttgtggaca tttcatatca gtcgaatcac atgctttgtg tcctgtgtct   6600

gttatttgtc actgagctcc attcacaccg cagcctgtgt cagtgctcca tccttggtta   6660

tggctgagga gcattctact ataaggaggc accacacttt gtgcctccag ctgctgatgg   6720

gtttggttcc accccccatt tcaaccattc tatgactaga gctgctgtta acatttgggt   6780

gtgagcattt gtttgaacac ctgttgtcag ttctgtgggc ataccctagt tgtggaattg   6840

ctgggtcata tgaaaattct atttaacctt ttgaggaatg actagactgt tttccgcagt   6900

ggctacatca tttcacaatc ccatcagcaa tgtatgaaga ttccattttt ttgacatctt   6960

caccaacact tattattcac tttttaatta ttattatatt catgctaggg ggtgtgacac   7020

agtacatctg gttttgattt gcatttccct ggttcccatc atttccaaag atgttgaaca   7080

tcttttcatg tggctcttgg ccatttatgt attttctatt ttaaaatgtc tatttaagtc   7140

atttgcccaa cttttaattg agttgcttat cttttagttg ttaagttgta aaagttcctt   7200

atatgttgca gatactagac tcttatctga cacatggatt gcaaatattt tcccccattt   7260

tgtgtagtat tttcactttc tcaagagtgt ccatgagttc atttttatag aaaagataca   7320

ttctttttca ttaaaacaat ctgaacatat attgtcataa acacaaagtg attatctctg   7380

aatagattgt caatgttttg ttattttgga attaaccctg gcaatatttt tcaaggttag   7440

taatttcaca aattggtaaa tggaaagtga aagtttctaa ttcttagctc atgttattat   7500

gatgtgtgtg catcttggaa aggacccaag gtgtggaaca tgcagggatt tctgaacact   7560

caatcctaga ggtgggagtg ctatcacagt cccagaccca gctggtcagg tggaaagccc   7620
```

-continued

```
ccctgcccag cccacctcag ttcctcgggt catcatcatc ggcattgttt tgtttctgtt   7680
tctcactctg ggctgtcct  gggaaaagga aaccgaaact gaagctgaat tagcctatgt   7740
aactctgacg tggtttgctc aggctattaa agggctgagc tgccagggct gaagagagcc   7800
gagagcagag aggcagccgc agccaaccag tgtctgcaga gagcctggca ccagaaccca   7860
cggccatggt gagtggtgag gcgggtttga caggtggggc tctgtattcc cctgcctggt   7920
ggcatctccc aggggaagaa tgcctactat gcacaggcag gtagagctac tcaaagcatc   7980
cggttcccta agtgtgaggg gagggacagg gctctttcta aaatcagggt ctgggtcctg   8040
aaaggtggct tctgcccagc cgccaactct gagatccctt gggatcagca cagggcaggg   8100
gggtatttta ttggagagtt gacatgaaga ttgtgggtag tagctcttct gctcccttgc   8160
actctccagt gcctggggtc cccatctccg tgggtgggaa gggtggagag gagggagctg   8220
catccccggg gtctgacact cgtcccactg ccagtgctac acgtgcagta gtcccaggac   8280
ttctgaatct gtgtgatgcc cacagggcgg ggacctgacg gtgaagatgc taggggggcca  8340
ggagatcctg gtgcctctga gggactccat gacggtatcc gagctgaagc agttcatcgc   8400
ccagaagatc aatgtgcctg ctttccagca gcgcctggcc caccttgaca gcagggaggt   8460
gctgcaggaa ggggtgcccc ttgtcctcca gggcctgaga gctggcagca ccgtcctgct   8520
ggtggtgcag aactgcatct ccatcctggt gaggaacgac aagggtcgca gcagccccta   8580
tgaggtccag ctgaagcaga ctgtggctga gctcaagcag caggtgtgcc aaaaggagcg   8640
tgtacaagcg gaccagttct ggctgtcttt tgaagggagg cccatggatg atgagcaccc   8700
gctggaggaa tacggcctca tgaaggggtg caccgtgttc atgaatctac gtcttcgggg   8760
tgggtaggga agggccagga gggccttagg gagggctccc catgcagcgc agtgaataaa   8820
gttgtagcaa agccaaatgt gaagtgttca ttccaccctg gccagcaccc catgtcatca   8880
gccctccatt cggcaccctt ctggtgagat tgggggaagg gtggaggagg gagtgggtga   8940
ggggactcag ggtcactgag tggtcaccag gctagggtgg ccaagttaag ggacaaaccc   9000
tgtgggatca aaatggtgac cctctggaga aactgaagat gtgtccccac ctctttggga   9060
aattaacttc tagagaaata aaaagaggca ggtctgttga agcccatccc tgtcttccgg   9120
ttgagcctca gtcagccctg cacaactggt ctccaccttc acagctgggt cagcagatag   9180
cagagggagg gaaaaggcct ggctgggtcc caaaggccac acagtgagtg tccctggaag   9240
cggtgagggg ctgagtccct agggcctgcc ttggccagtg gtaagggagg ttcccccaca   9300
ccagctggag gctgagggcc tccaggaccc atcagaatac actgtccagc cttcattggt   9360
ctggagggaa ttggggactg ggccttgggc acacacatca ccattagggt gagctgctcc   9420
ttcagagttc acatcatgga agggccatag ccagcaggtg agggggcacc caggatgggg   9480
gttcctgttg ttcacatgga tgggagggga acaaactaca cctgcttcca cactagatgc   9540
ttctttctgt gccagtttcc caagtgagtc agccttggac agaatgcggt gggcagggag   9600
ggggacacag aacctatacc tcttgggcca aagtccatga ctctggggac actcagatct   9660
cagctttcgg actcttcagg ggcatttggc tggagaccca gaccccttct ttctgatctg   9720
tgggagtttg catctgagct gggggacccc caggtctggc ttgcctgtga cacttatgta   9780
gacacgcagg tgtgtgtgtg tgtgtgtgtg tgtgtgtgtg tgtgtgtgta gggggactcc   9840
tggctctagc ctcatttcct gggcccccac cctcacctct ttgtcatact gtaacttaac   9900
aagtgtgagc acgccctctc ggtgacaccc tcctttcttg aatcccctca gcagggtctg   9960
ggcgaggtag ggtccttctc caagatgcct ctgggctgct cacccttcat ggcctctggc  10020
```

tcagagatct gtggttggct tggatgaggg ggtgtgcagc agactcagcc ctggaggaac 10080
agaagggatc tcctctcctc ccattcccac catcttcagc taagtcgggc tctaatttgc 10140
acactctgga tctcagttta ccccctggac ccagcgggaa tggttggaga agtagcggga 10200
atggttggag aagagccttg gggagctgg gaaggggcg tggctggccg tccatcgctg 10260
ctgctattcc cacctcagtc aacaggggga gcccgcagcc ctgcagaggg ccgggagccg 10320
acccgggatc gcgaggtggg cggggctgcg cttcgctgcg accaatcgcc gcagctccca 10380
gcccgcattg gtccccggtg gccggtggtc ccgggcggcc gagcttccgt ccccagttcc 10440
tgtgaggggc taggatcccc cgtcaggttc ctctcgccgg gggaggggcg cagccccttta 10500 gggcgcgagg ggccgcaggg cctcggatct ggcagcccct tcttgcggcc agggagcccc 10560
cgccgcccca gccctggcgc agcctggagc cccttggaag tcccgtcacg tcgtctccag 10620
attatgcatt aacccgattt cagccgcatt tcctggcggg ggggcggggg ggtggaacgt 10680
ccgcgcgaac gggggagggg cgtccgtggg agtgcgccac agcagggaga gcaccctcga 10740
gcccgcccca accccgcccc tcggcctggc caggcccacc acccaccttg gccaaaccta 10800
gaccggcccc ctccctcccc cagccaggcc tccgcccggc gccgctttcc cggcgctttg 10860
ttcgcggctg ccgcgggtcg caggacgccg ggagggccgg gggcgggcgg gccgggggg 10920 tgggggggtgg gggctggaag ggggtggtgc tgccccaagg cccgcccccg caccgcccgc 10980
gctcccgcca cctcccccga gctgcgtccc gtcctgtcca gtccagtccc cggcgcggcc 11040
cggtccgtgc gcttgctccg gccgccttcc gccgtcctct gcccgcgcca tggccagctt 11100
tcggccgttc agccgggccc tgctgcagcc tttgctgctg ctcctggtgg tggccgtgcg 11160
cgccctgccc agcgccgacg ggacgtgccc cgaacgcgcg ctggagcggc gcgaggagga 11220
ggcgaacgtg gtgctcaccg gcaccgtgga ggagatcctc aacgtggacc cggtgcagca 11280
cacatactcg tgcaaggtgg gcccccctggg gacccccggg accctgagcc ccttcagacc 11340
cttctagaag ccctggttgg gggcccttcc cccgcgatcc cggacccccta gcccggaggt 11400 cttcccgtcg cgatgccggc cgcgcgctga gacccccgtc ccgggacgtg ggaacgagcc 11460
ccagacgttc cgcagcacca gctccggctc ctgctccctt agcgaccgcc gacccccggt 11520
gggaggggtg gggggcgggt gcgggtctga gaaaactcgc gagcgccgga gggaaagttc 11580
ctgcggtgcc gctgcagtcc cgctcgcggt gcccgggccc tggagacccg atagtgtctg 11640
ctccttcacc ccaaacccac tcccttactg gaaacaagtg cgccccgccc cccggagaat 11700
gttcggctac cgcgcccccct ccccaccggc caaaggaaag gggacgaggg gaggtgacgc 11760
tttctgcttg ggatggaggt ggtgatttgg cctgtggtca gtgctgtcgc cctctccgca 11820
gaggtgagaa tgggtggtcc ggagagagag gaggggtgca cacctaatct cccaaccgcg 11880
ggggtcctgg tggggcttgc tgcagtgatg ggtgtggggc cagagcagag aagtgggcgg 11940
ggccgttgct gagcctcaag tgcgggggggt gcagggcagg tgccccatcc gctcctggga 12000
gagctgtatc tcccctggcc ttagggagag gggccttgcc tggcctctcc ttcagttgaa 12060
tctgggagct cccggggtag gtctggtggt tttttttccca caatctgttc ctagggagga 12120
ctgaagggac ccaggcccct gcccctctct ggcccctaaa accacctccc tgaccagaaa 12180
tcggatcatt cctcttcctt ggagatgggg aggggtggca gctcctttca gactggcctg 12240
tgctgactac agctgggatc ccccgccagg ccccctcccc tccaccacag ccagggcact 12300
ttgccaagtc cctgcaggat tttcccgact tcctccccgc tgctcctggg tgtggctggg 12360
gtggggggag gcgatgaaag ccgcccagct ctcccctgct ggttattggc cttccagagc 12420

-continued

```
ctactctgta tctaggcatg gggggcgggg gaagagctgg cagccccacc atccctgggc  12480
cactggaggg tggagggagt ccctgtagat tttgcagacc caaggctccc agcaggggtg  12540
gccaggtgga cgggccactg ttgtctttca ctcctctttc cagaagtccc ggcccccata  12600
gatcctgaag aaaggggtgt tttttctcag ggacagcatt cccgggcagt ccccatgggc  12660
ctattccttt agggcagctc attctgcctg cagtgcctgt ggccctcctg cccccactgc  12720
cagtagtctg tgggcacccc cagggcttgg tttgtctgag caggtgccct cagggcccca  12780
agagcagagt gtggagggtg gggctgccct gtgctgccca aacttgattt tgtggttcac  12840
aggctgcctt ggcagcactc actgtaggag ccttgcagga ggaggggtct ttcacctcct  12900
ggctggaccg tgtcttagcc cacccacagg gctgcatgga gccaagctgg acaggagcct  12960
tgagctcaga gcccgtcacc ttgaaacttc atcatccatg ttagttgctc ctgactcttt  13020
ccagaggtgg gcccaagtac tgggtgggtt gacagggaga gtaaggtgtg gaaggctgtg  13080
aggtgtgaca tttagaactg gggtggctgg ggtcatctaa acctgagggt tagggagctg  13140
cttcttgagg gaaggggtgt gttctcaggc caggtatcct ggagtataac aagggcagtg  13200
gcgtctgtca tgtgtgtgtg cttccctgca gcttcctcct ggggggttgg ggcactgact  13260
ccacatatct gcccagggtt tgggtatact ccggacatct ggcctgagca aatgaggtgg  13320
gaaaagaagg aaaagtccag gcaccagtct ggtgtctgcc tctggcctct gtggccatct  13380
cccccgctcc acccagttag aagagaaccg ccgacaattg aacaccccct catgtccacc  13440
ctaggttcgg gtctggcggt acctgaaggg caaagatgtg gtggcccagg aaagcctgct  13500
ggacggaggc aacaaagtgg tgattggcgg cttcggagac cccctcatct gtgacaacca  13560
ggtgtccact ggagacacca ggatcttctt tgtgaaccct gccccgccat acctgtggcc  13620
cgcccacaag aatgagctga tgctaaactc cagcctcatg cgcatcaccc tgcggaacct  13680
ggaggaggtc gagcactgtg tggaaggtgt gtgtggggcc gagcagagca ggtgccttgg  13740
gggcagaagg gagcttgtcc taggctaggg cacatggcat cttgtggtcc gacctccttt  13800
tctgggtcct ggctccctgg tttcctggcc acctcagctc cagactctta acataagcag  13860
cactccccac cctggcccta gtgttgccac tatctgtcat cttggagtct cagacctgca  13920
aagggatagg cctcccattc ttccctccgc ctccccagct ctgcacgccc cttcctggag  13980
ttccctgttc taggaaagag gctggaacca ggtgaacgaa caccagttgt ttgtgttctg  14040
cagaagcccg aacacatgtc tagacggggc ccagatgttg agcctttggg gtggggctta  14100
aagattgtgc tggaggggag gctaccctgt tatgtgttcc cagaggcctg ccatttctgg  14160
gaagggacag ttatgtggag tgagctgctt ctaggagttt gaggggttgt gggatcccct  14220
gacagaggtg gagcatcttt ccttgtctgc tgtccccatg tgtctattct gaatggctca  14280
agagcaaccc tccctcacat gatggctcac ccatcccctt caccccagga gaatcccagt  14340
tgggggctga gatccttggc tgaggaatgt agcagggaga agtaggaact gcctgtcgcc  14400
ctcacatcct gtctgtcccc tcatggctgc ctggggaggg atgtatggga ggaggtggag  14460
agatcgcttc ctcccaggc agcaggaagg gtccctgact tcctgtcctg ggaaggcgac  14520
cctgtccctg tgacttgctc tgttggccgg tagggaagtt ccatcttcta cccaacttaa  14580
ctcctgtggt gctggcttgc ttttgtggga tcctggatgg tggactcatc tggcctgggg  14640
cagactgtgt gtgtgtgtgg cgaggtgtgg aacctgaagt ggagagccct gtagcatcct  14700
gctcggcctg cagtcatttg ctcctgggat tgcatctatg gtcctgatgc aacatcgcac  14760
agagatgcca gcagggctgt gtccctggtc ccttcccagc actagcatag ctgaggggtc  14820
```

-continued

```
ccagcatagc cctcccacca ggtgaggact ggagaccctg actgtgcttt ggaagcttta  14880
ctctagggga aatatgggag agtggcatgg agaggaggca ggttgtaggg tgtgatcccc  14940
agttttggag gatgagttgg agactaatga gaggtgggaa gaggggtcag gctgcagaaa  15000
atctgtttct gcaagatcaa gaagacaagt cattaactcc atagctggaa gggtctagtt  15060
cgagggtctg tggggtcaga gggcatgtgg caggggggcc accctaggca gaagagggtc  15120
tgccatcttg ccaggtccta ttctacccag gccaggccct ggctctggat atgtcagcct  15180
gggcacagga cccctggaaa ggagggtctg cagagagagc ccccagtgag acttcatctg  15240
ctgtctgctg gctaccccgg atagggacca gtctaggccc ccagctccag ctgggccagt  15300
gtgggcatgg tggtggaggg gaggccccca gggagggagg gacccagaat gagaagcttg  15360
gggtccactg taaggctctg gggagccctg gaagttttga gccagtgaca cggatccctt  15420
ctttggaagg aaagcagtgc cataaggggc agggggccag ggagagggta gattagatgg  15480
ggtgcctccc tctaaggatc cccaaagcct gaaggacaag gctcccagga gttggtgcca  15540
ggcttgagga agacacagcc ctcttcccac ctcccacagc agggagcagg caggagaagg  15600
gcctgcctcc cattctgtaa gcgatacctc ccattctgta agagataaag acctctgacc  15660
ccaccccagg ctctccaggg agccaagcct caccttagca tggggggtag ggttagggat  15720
gggccgagct tgagctacaa tgacctctca tctgaccctg acccttttct cttccttggg  15780
gccccatagc tgcccccgtc cctcagggcc ccgagtgaag gctgtgaagc tactgattgt  15840
ggaggtcacc ccaagacctg tgtctctatc acaaatgtcc cctgccccta aaaggcccac  15900
aggagccaag gtcaggggac acatcctgga ggcccacccc cctagatgcc cccacctcat  15960
ccccacctgg accctgcttc ctgcaggggt acctgttgct gggaggcata cctggtcccc  16020
agctccactg ggctcgcctt cctcagtttc tcccttaggg cctgcagggt cttcctggct  16080
ctgggcccct tccccaacct ccagtcccca ggaagctcct ccccaatcct ctgcctgggg  16140
agccacattc cgagcataac tgagacaggt atgtgtccct ccctctgcac cacttgtggg  16200
tgaaggagac tgcgggtttg ctccaggaag gaaggagacc ctcacgccct gctttgtcag  16260
ggaagtggcc tggcctcttc cagtgccagc tgcccacgca tcatgagctg cccaggctgg  16320
cagctgagcg ggcatctcct ccagcctttg gccactatac cctggtctgg acttgtacac  16380
ttgtacactc ccaccaccct cctctccccc acctaataaa gactggtcct tgggcccccc  16440
tgaattccct aggagggatg caggcttggg gtccttcccc aggcctttcc ctcccgaact  16500
ccgagccaag agcagagaaa ggaagtgttg tctgccctct ccgggcctgg cacaggaaca  16560
gggtcggaga gtctggcatt agtccagccc agccctgccc agtcctgaag ccgggggtcc  16620
tggtggccac agcctagact ggcctgcctg attccagtga gcaccctccc ttcctccctg  16680
ccacgctagc ctttgggcct tcacgccagt cttgggcctt tggggaaggt agtcctaggc  16740
tatatctcag gctagagaga tgctgggtcc cgggccgccg gccttggcct tggtgcaggc  16800
cctgtggcct gggagccgga tgtggacaca gacaccccca gacagggact ggctccgcag  16860
agcaaagcgg ggcaggtagg agcccagggc aggttccagg gctggcttcc tcagggctag  16920
agctggctcc ctctgctgtc tggcatttag cttctgtacc cccaagtcct gagcccgccc  16980
tactccccca cattcctccc tgccgagggg ggaggtggct tcttcctgtc cctgtttccc  17040
tcttccagac gtaagttctc accccacccc ctccagaccc gccccagtgc cgtcctcagc  17100
ccctccccca ggcaggtcct tggagctggg gcaggcccag gctggaggct gcgcgcctgg  17160
gctttctcct tccttccagc cactgggggc ggggcatctg ctcaggtgga gcgtggcctg  17220
```

-continued ctcctgcact gtcctctctc acctagggtc cccggtagga agtctccgag agcatgggct 17280
tgtgggacca cagcgggctg gctgataccc tcactggggc ggccccagga gcttggggcg 17340
tggtgggggg tggggagggg gttgctgctg aaatcaaagg gcattggatc catcacttca 17400
aggcagtgcg ctcctttccc gcaggcctga gctggtggaa acagctcctg actttttcca 17460
gaccccaccc catcaccctg ctccccaccc agagaagagc cccgcctcc atactcccca 17520
gcagattgga aatggaaaaa aaaaaaagtt gttttgaaac tgtcctctcc cctgctgtct 17580
gtacctgcct tccgcagggc tctggacaga gtagattcca gtggggcctg cctgtggaag 17640
gaaggcagag ccatggaggt gctcgcagcc tctctggggt gctgggaaga actggatcgc 17700
ctggtcaggg ctagctggtc tggatctggg gctctagccc cctgccccac caatcctttc 17760
agactgaggt agggagagtg cagagggtgg gatggggctg ccccaggtaa ggttagcagg 17820
ggcgtgagcc cagacttcag ggttgtagat ctagccaact gttgcttgcc ctgcacagcc 17880
tcctccagcc tgttttgctt ccttcttaaa gggttaatcc cccaatcccc tgagaatcaa 17940
agcctgcccc caccccatca ccacagtggg gtggaagaca gctgctgaaa ttgacctctc 18000
tcctgcccct gccccccaag tcctttgcct tcaccagaag gcccaggcca gctgccctcc 18060
ctcccagccc agaggcctga actgctctgc tggccccagc aaccccctca gcattgggat 18120
aggggaactg tggctcccca cacaggcccc tgaggcccag cccagcaagc tgggggctgc 18180
aggcacaatc cctgaagtag ccccaatagc acttaacact ccagagtccc aggaagcgcc 18240
cacctctcac aaagagaaaa agggatctca gaaatgagag ttagtgacag ctaccctgat 18300
gagattgacc cagctcatca gagagtactg tgtccccata ggctacaggg ggctcaggag 18360
ggatctgggc cctattctag gctgtggctg ggaaccgggg aggggtgacc tggcctctgg 18420
tggagcttcc aatggggagg gaagctcccc tcaaaggggc ctctccctcc agagcagatc 18480
ctgagaactt cctctgagga aggccccctg ctaggggctg cttacagctg gacctgggaa 18540
ggggaagatg gtccctccca cctcccctcc cactgaggca tgggaggggc aagctctctt 18600
tcctcacagg cagccggctg tttccagctg tgtggcctgc acatgtgtgt gtgtgtacat 18660
ttgtatgcac gtgtgcctgc aacctcaggt gtaccaacca ccacacaaca gttctggttg 18720
aaactccagc tggtggcctg tggttcctgc cacccttgta tcgcaggact cagcctgggg 18780
aggggaccct gcagatgctc tgccaatggg atggtagccg gcaaccttgg cttgtgtccc 18840
agagttctgg gaacagggct gtgggccctc tgtgggtgcc gtctcctgcc tgctgcccca 18900
gtgtccagct gtgctcccct cccaccaccc catccccggc agagagctgg gcccctgctc 18960
ctgtgggctc tgccgctggg tttctcaatg ccagagatgg aagggctgca ttgaacagga 19020
agagtccctg ggatcacttg ggttccctgt cccctcacgc ctgctggacc ctgtgtctgg 19080
ctaagttagg gagcagggca ggtcaggaga ggtgggtctg cctttgatgt gaggtgggcc 19140
tgaagctccc tacctctcct cttagcaact tcctctgcac tgccccctct gcataccagg 19200
cccagaagca ggcaacctgt tgtggctccc tgaggcacct gtccctctgg caacaggtac 19260
atgatttcta tgtacattgg ggagaaataa aggcacaaca tctgggccag attatggcct 19320
gtcctgaccc acaagtgggg aaaggatgta tgtccacccc tgttcctaga gggggggaag 19380
tgaagcttgc tagagtccac tcgtgaatcc agccatcagt tccttcctca cccacccgtc 19440
cacgcaggac ctagcagcag gccctcacag gaccactaga agggctgctg cagctaccca 19500
cgcggctctc tcctgtctgg tcggtctttc tgtccctttg ttcccagctt ctcttggttc 19560
caatgttgta gccatgcgtt ctgggaaaca cactcactca gaagcacaat gcaaataacg 19620

-continued

```
gagtgcagtt tattacaccg gcgggcccaa ggcagagtct cctcttagcc aaggaccccg  19680
accagttttt ctgaaaacct tatataccct aagtgtacgt gcccaaaccc acctccccaa  19740
attccctgaa actagtctga acagaggaaa agaaagatac agtcaaagtt aacctgtgat  19800
tcatatgcct taagcctagg tagttaacag tggaccatta ttaataggcc tgtgatcata  19860
ccccaataag cataatagaa tttatgattc tatgcggtta cacagataat tagggtattc  19920
tttaggtaac agagagtcta ggaacgagcc ctggggctct tccatccgga ggggtctggt  19980
tttccagttg gtgtgtcgtt tccatagata ctgggcatat agctcaaagt ccacagtccg  20040
gcccaagatg gagtcctgct ttcaagatgg agcctggtct gtctgtttcc tccttcatcc  20100
ctcctcttca tgctcttaac tcatagtatg agcatcattc atagggattt attgcaccct  20160
gactctccga cctccaattt gggagaacga catcaacctt tgggttacag agttcataat  20220
acattgtaaa ataaagggtc cacaaagcag aactatgaag gcaactataa caatggtaaa  20280
tatagttttc caccaatcac ccttcaccca acataggacc gaagtccaaa aaggaagatg  20340
tatcagacat aacttttacc tgacctttca tgtcatctag ggtagctgat ctatagccag  20400
ataaatcagg aatatacaca caacattcaa ctttaattat agcacaggtc cctctttgta  20460
ctgaaactgt ggtcaatctc aagatgatag cagcaagtcc ttgtagcagc agttgattgt  20520
agagcttcat ctctgtttct tctttaagat gatcttggtt tcatggggat cagaggggtc  20580
cctctgcaca gtccactcgg cgtcctccgg gtctgcatgg tatgctctct tcagcctcat  20640
gtggaggatc cagggagtga cacctgcaac tttaactgca gtagggctgg ttagaacaac  20700
agcatatgga cccttccaat gtggggccaa ggagtcgtgt ttccagtcct tgaccacacc  20760
cgatccctgg gcacaaattc gtgaatctgt tccccaaggg ggaacggcac cttttcttgt  20820
acaaacttag ttacctgatt tattacctta cccagttgtt ccatctgctg tgaaatctca  20880
tctcccctta cctgaggcaa atttgttgac acctgtttta ttatgggagg gggcctccca  20940
tacacaattt tgtacagaga cgattcatgg gactgtgggg tcatcctgag tctgagcaga  21000
cccgtcagaa acaagtccac ccaggaaccg tcagtctcca agatccactt ggagagtgtc  21060
tctaagtgtc cggctggttc cttccaccat cccagaactc tggggcctat atgctgtatg  21120
taatttccac ttgatgttta aagttttgct tacttggtta tactaaaaca gctacaaaag  21180
ccgggccatt gtccgatcca atgctggtag gaaatccaaa tctgggaact atctccctaa  21240
gcaggcaccg ggctactttt gatgctcttt cagtgagggt aggaaaagct tctacccatc  21300
ctgagaacgt acatactgtg accagcaggt aatggtagtg tccgtgaggt ttcatttcag  21360
ggaagtccac ttccaggtgt tcaaagggca gcgtgccttt tacctgaatc cctgcaggtt  21420
tctgtctgtg ccaacaggca gcattggcct gtaagcaggc agtgcagttc tgagattttg  21480
tcctgcatgg ggaagagagg aggggaacaa agaaatagtt tcaaattatc tcttccagtt  21540
tatcatggca tagatgggtc gcttggtgtg tttggcttac cagagtgggt gccagctcct  21600
ccggtaccca taatttgcca cttggcaatt cccactatcc cttttcagtc ttgatggccc  21660
cttctgcttt ggctagttgg ttttgagctt cagtgtattt tggagagtct agtgttagct  21720
caggtagctc cgccaatatg aaagctttaa caggggcttc acttgtcacc cccaagccct  21780
tggctgcttg tttagcggtc ttatctgcca gtctgttccc tgagcccggg gagtatcctc  21840
tttttgacgt tctcagcagt gtatgactgc aatcctttct ggttcccagg cagcatctaa  21900
tagggtctta atttcttcct tattttttat ctttttcact agctgtcaaa ggcctctctc  21960
cttatacaga gccctgtagt gtggcaaaag catacctgga gtctgtgtca aggtttgtct  22020
```

tcttaccttt tgacagctgg agggcctgga ttagagcata tagttcagcc tgttgaatgg 22080
agcagtgtgg tggcagagag ggagcctcaa caatggtttc ttctgtgacc actgcatatc 22140
ctgacagtca ttgtccttgt ttcaccaggc tggtgctatt ggtgtacacg accgaatctg 22200
ggtccgggat tggctggtct ctcaagtcag gtctgctggc atatttcctt gcgatcatgt 22260
gagggcccac cttctcccac aggaaggaga gtggccagat tcagggcctg acaaggctca 22320
gtagtaacat gggggttctc acataacagt ccctggtact gagtaatctg ggatgttgac 22380
agccatttat ggaggtcccc ttgcaggaga gtgttgacct catgtgggac ttttacaaac 22440
aaatcttggc ccaaagtcag cttggttgca tcctggacca gtaaggcaac tgcctgtaag 22500
catcccagcc acccagtagc aacactgtcc agctgattag aggtaagtca caggtctgtc 22560
ccatgtcccc atagtctggg acaacactcc tatagccacc ttgtcctttt cagtcatgta 22620
aagagtaaat ggcttagcaa ggtctggcag gcccaaggcg ggtgctgatg taactgtact 22680
gggtttgagt tttattacca ctgggacttg ttttgcaagc ctgggggggt tgtcttctgc 22740
ccagacctca gggaattgtt gagttaactc tctctcttga ccattgagcc tgtccggttt 22800
cccttctggg agatcgtgca atctcccttc atcttgaggg gttactgaga ggaagagtaa 22860
ataggtggtt aagcccactc gaacagtggg tctttcttgg ggagacagtg acttgttccc 22920
ccaatttaga cagcaagtct cttcctaaca aaggtactgg gcattcaggg atgtataaaa 22980
actcatgagt cacttggtgt ccccccatct gacattttca gggtaggcta gagacacaag 23040
gctgcattta tcaccatctg agacccagca gcctctggct gggtctattg gcgtataaag 23100
tctataggcc tcgcatagtc tttcgcagaa ctcagggtga ttcgctttcc ctttgaatca 23160
cttcagaggg ttttgtgata cttatagctt ttcgggcccc cctcttgaga ccttgtaaaa 23220
tagccacccg ataactctcc aggtggcccc tcccttcctc tgtgttacag tcccagttgg 23280
gcctctcatc cggggtggct agttctgccc accgctgcgg gtttgcggta ccctcaggtg 23340
ccatttc 23347

<210> SEQ ID NO 4
<211> LENGTH: 23363
<212> TYPE: DNA
<213> ORGANISM: Bos taurus

<400> SEQUENCE: 4
acccactcca gtacactcgc ctggaaaatc ccatggatgg aggaacctgg taggctgcag 60
tccatggggt cattgagagt tggacaagac tgagcgactt cactttcact tttcactttc 120
atccattgga gaaggaaatg gcaacccact ccagtgttct tgcctggaga atcctaggga 180
cgggggaacc tagcaggcgg ccatttatgg agtcgcacag agtcggacat gactgaatcg 240
acttagcagc agctagttgc aagtccagag gaggaagtgg cattcccaga atggaaagga 300
accacagggc caagggagga ggggccggga caggtgggaa ccaggctcta gtggcttcag 360
gtccccagag gggtctaaga gagtcatgct tggcttttct gagcagcaga gtggcccaac 420
tggcagctcg gaagggccac ctcccacact acattctacc tggtgggtgg cgatgctggc 480
tggcccccac ctcaataccc tttcccaggg gtccagtctg gggcccagtg cagacgcctg 540
tgatgcaggt ttgatcactg ggtgggggaa gacaccctgc cccctccccg gaggaggaaa 600
tggcaaccca ctccagtatt cttgcctggg aaatcttatg gacagcctgg agggctacag 660
ccaaaagggt cacaaagagt cagacacaac tgagcaactg aaggaaggac cctcctgtac 720
ctgtttcctc acctgtaaaa tggctacct tttcatttag ccctggacta tagtccatgg 780

```
ggtcgcaaag agtcgaacat gactgagcaa ctaacacttt cacactttga ctgagaagat    840
aaatgagatc tgattttgaa agcacccagc acatgcaagc gggacagagt cacctggatt    900
cacctctgcc acaagcccca ctgtatcctc taccctctga gacaccctct ccctacctgg    960
ggtcttcaga agcctgtttc ttggcccttc cagccccaac aaggagcctt ctctcaccca   1020
gagcagagtg agtcccaggg gtgtcatcta catccctgtg tccttcccac tgggctgcac   1080
ccccactctc tctctgggcc ctcctacctc tggctgtccc ctccctgcct tttacatctg   1140
gatttgatct ctggtaggac ctgggactcc tggggaccgt aggggctccc ttgctctgag   1200
tagagaggga gagtcctagg ctgcaggggg gaaactgtgc tgagaaatac tgacgtggaa   1260
cactgcattt tccaaagatg gctacaatac atccacccca aatactctac ctgtgtgtcc   1320
ttggtgagat tttgtgatga cattaaccag caaagacagg ggcagtggtg atctatgaat   1380
tctgaggctt gacttgaaaa acgtgcacct tgctgtcctg ggaaactcac tcctggaaac   1440
cactgacccc tctgtgagga aacccgaact ggtctcatgg aaaggcctca tggagaggcc   1500
ttgtataagt gttgagctag gaacctagaa atctcagctt ccagacaggt gatcccaacc   1560
tgccgcttca gagcccccac tcacactttc ccagccagct ctgtgtgctc tgttccactc   1620
ttgattcaca tgactggtgt tactgtgaca ctttggggtc attcgttacg aaacaatagt   1680
aactggaaca gctaagatgg cccaagccct ggacccaccc ccctccccag ccccaccccc   1740
caaaccttgt tccttccttt ctctggcatt cacagagtca caggagcttc ccgcactggc   1800
tgtccatctg acgaggtgac ttttgcagct atccaaggcc aactatctgt cctcctagat   1860
ccaggcttga gttggccaag tcccagtagg ctgatggtcc caggggcatc tctagggacc   1920
actgttggcc actgggcagg aaaagtagtg ggggagtctg tgtgggaaga taagtgtatt   1980
ttccagtcca gacactgggc tgcagccttg gtggggggtg gggggatggt ctttctcacg   2040
tctggctccc atgacagcat tccacaacat tcagacagtg tccctccggg gcctgccagg   2100
tgctgtctgt gcacaggccc ctcccaacct ctgacagggg ggtggcacct gcacttgcac   2160
cctgcccctc agcattccac aggcacatgg gtccctgaat atcagagaca ccatagacca   2220
tgaccagcaa ccccatcctc ctgttccctc ctcttctgcc aagggacaac aggctgtgga   2280
ctcaggcagc caggaccaga gttgccatgt gaccaggcta gagtcattgc agggtctctc   2340
ctggagcatg ggagttgggt cctgagatga taaagtggca gaggctaggg ctggaggaac   2400
ccaggattca gtatagagaa gaaggaagca gatgaccagg accctaatct taaccctgag   2460
ggggcatctt tcatttttac aggccagcgg accaagacac cttccttcgg ctcttggtgc   2520
tgggcagttg gagcatcccc ccaacacctg atgcatgaca gcacctcccc cgaggtctgg   2580
gcattgtcaa catctttctc cattattgaa tgttgacacc tctccacgct ggggaagcca   2640
tgtctcccca attctgtgtg gtaacagagc ttcccaccct gtctgcctgt gatgccacct   2700
ccctgtgggc ttccatgggt gcttctctct ccagtctcct tggaccacta ctctctggag   2760
aggtatgctt tgctctcctg ctggtcacat ccagactagt ttcttcttca ccaaaaaaag   2820
tcccagcttt gaacctcatc ttattaacag atctcatctt gtgaagtcca ctgcaaccct   2880
gcgggggggg ggcctcccca taccttctga aggttcactc ctgattccct gtcactttct   2940
ccagcggctc ctgtcacagt ccttgttgac ttccaaattc acacggttga tcttctggac   3000
ttcctggcct ccatggggca tcctagtgta gagttggcaa ctaagcttcc aatcctaagt   3060
gctgggtgta gactgtagcc gtaatattcc catccaccct ggaggacacg cccaccagga   3120
agccccgccc acagggcaca ggtcagcatc tgcagtacaa tatcctgctg ctttcccagt   3180
```

-continued

```
gtaacctggg gtcctgcctc ctccctccac actctcagcc tcttgtctca ggttctgcct   3240
cccgcttctc cttgtgcctt tcagtcctgt ggaacttggg gaacaagtct tcactctaat   3300
ctttctatcc acacaactgg agcactctct gcccagtggt ggagcctgac tgaggcacca   3360
gcctcctctg aatctgacta ttctcagttc tcagaccaga ttctgccatc gtcctcgacc   3420
ctcagagttc actcccagtg ctgctctggc aggtcctaca gtggctctat ctccctgatg   3480
tatacaaaca cctacttctg acctattgct tttccaccac tggctgcaag ccgccaccag   3540
cttcggcctg gaattttgta gttctttgcc atggcaaggc agccagtctt ggagccgagt   3600
gctcaatggg ggcaggtgga caggagagga gattagaggg tcagcagagt ggtcagaaga   3660
acaagcctaa gctcctatct tctctcggaa gcttatggga agccatggga gagaaggttg   3720
tgtgtagatc actctggccc ttggctccac cacagattat ggggtcagga tagaagcaca   3780
gccactcggc tgtatccata gcagcctcag tggacgaggg cgcatagata taagtgaggt   3840
catggatatt cttgggagtt ttttgttgtt gctactgctg ttagatggct gaagggctta   3900
aaaataaaag caagtgtatt aaacgatata gatactgttt taaaagtttt aggaagttta   3960
agttagtttg taaatgaaac caaatattaa ccaaagaccc ctttataagt agccattgta   4020
acttcataaa taggatattc aggtttttgt ctagaacata tgtattttgt gatcatgttg   4080
ttaggtgcat acaaattaaa aataatttca ttttatcagt gagctcaacc ttttattgtt   4140
atgcaacctt ctgtatctag taatgctttg actataaggt ttctttgtta atctgttagt   4200
gaaactgtta atacggtcac atctgcttcc ctttagttaa cattacgcag taggtttctt   4260
ttctcctttt actttcagtt tcctgtacct ttatatttca tattatttat gtcttctgta   4320
agctgtgtaa aatcagatta tttttaatca ggctgacaat cctggtcatt tagtccccct   4380
ggatttcaga cctctgctct ttagaactgt gagggaatac atttctgttg ttttaagcca   4440
cccagtttgt ggtggcttaa aagcctccaa gacacagaga catgcttcca gggctatcgt   4500
tttgcctgcc gaaagccttt gcatctagtt cctcttgtcc aaagcaggtg atattcaata   4560
aagtaataaa agaaaataaa ggttctatta ctatatatac catatttttg ttatcttttt   4620
aaaatttttt attacttaaa attttttga attgttgttt cattccctta tctttgtgcc   4680
atatttaata atggtcacct agggactttc ctggtggtcc agtggttaag acttagtgct   4740
tccaatgcaa ggggcatggg tttgacccct aatcagggaa ctaagatcct gctggctgca   4800
tgccatgccc gaaaaaaaca aaacaaaaca aaacaaaaaa cagaatcaaa ataatggttt   4860
tttgaagaag acagggattt tcacattctg taatatttgt tttgtttgtg gctttctttt   4920
tataatacta atattattta tgcaaggaat gagtcaagtt agaaatttag aataatataa   4980
acaatattta aactgtttta tgcatgttaa caactttggt gccttatgat tatttggggg   5040
gaattgatgg aatgattaat tcatatgaaa acaatttggt tttccccatt ccttttattt   5100
atttaaaatt tgtttattta gtttaaaatt tatttttaaa atatttaatt atttttaggt   5160
atttattttt attttattta tttattttgg ctccatcttg tgggatctta gtttcccaac   5220
cagggatgga acctgtgctc ctgaagtgaa agtatgaagt cctaaccact ggactgccag   5280
ggaattccct aagtatttat ttttattttt agctaacata tgcctgagat gtgctgtttg   5340
taatagtaaa aatgtgggaa caaccaatat ttatttaaaa atatgagact ggttaactaa   5400
attacacttt attctataat ggactttgtt gctatgggca acaaatgcac atatgcagcc   5460
attaaaacaa cttgcataaa aatatgaggg cttacaaata gctgagaaaa gaagagaagc   5520
taaaggcaaa ggagaaaagg aaagatatac ccatctgaat gcagagttcc agcgactatc   5580
```

-continued

```
aaggagagat aagaaagcct tcctcagtga tcaatgcaaa gaaaacaata gaataagaaa   5640
gactagagat ctcttcaaga aaattagaga tatcaaggga atatgtcatg caaagatggg   5700
cacaataaag ggcagaaatg gtatggatct aacagaagca gcaaaagagg tggcaagaat   5760
acagagaaga actatataaa aaagatcttc atgacccaga taaccacgat gatggtgtga   5820
tcactcactt agagccagag atcctggaat gcaaagtcaa gtgggcctta ggaagcatca   5880
ctatgaacaa agctagtgta ggcgatggaa ttccagttca gctatttcaa atcctaagac   5940
atgatgctgt gaaagtgctg cactcaatat gccagcaaat ttggaaaact cagtagtggc   6000
cacaaaactg gaaaaggtca gttttcattc caatcccaaa gaaaggcaat gccaaagaac   6060
gctcaaacta ccacacattt gcactcattt tctcacacac tagcaaagga atggtcaaaa   6120
ttctccaagc caggcatcaa cagtacagga atcaagaact tccagatgtt ccaggagttg   6180
gtgatggaca gggaggcctg gcgtggtgca gtctttgagt catggggtct caaagagtcc   6240
aacacgactg agcgactgaa ctgaactgtg aatgaagcag ggtacaaaat gttgagagta   6300
gcaggaggat tttttttttc aattttcttt tttattgagg tgaagctcat gtaacataaa   6360
cttaaccatt ttatagtata taatccagtg gcatttagta tatttagtcc aaccatcacc   6420
tctatctagt tatgaaacat ttttattatt cccaaaggag gccttagctc catgaagtgt   6480
ctctcctcat gcctcctccc cgcagctctt ggcaattact aaggtatttt cagtctctat   6540
ggacttgcct cttgtggaca tttcatatca gtcgaatcac atgctttgtg tcctgtgtct   6600
gttatttgtc actgagctcc attcacaccg cagcctgtgt cagtgctcca tccttggtta   6660
tggctgagga gcattctact ataaggaggc accacacttt gtgcctccag ctgctgatgg   6720
gtttggttcc accccccatt tcaaccattc tatgactaga gctgctgtta acatttgggt   6780
gtgagcattt gtttgaacac ctgttgtcag ttctgtgggc ataccctagt tgtggaattg   6840
ctgggtcata tgaaaattct atttaacctt ttgaggaatg actagactgt tttccgcagt   6900
ggctacatca tttcacaatc ccatcagcaa tgtatgaaga ttccattttt ttgacatctt   6960
caccaacact tattattcac tttttaatta ttattatatt catgctaggg ggtgtgacac   7020
agtacatctg gttttgattt gcatttccct ggttcccatc atttccaaag atgttgaaca   7080
tcttttcatg tggctcttgg ccatttatgt attttctatt ttaaaatgtc tatttaagtc   7140
atttgcccaa cttttaattg agttgcttat cttttagttg ttaagttgta aaagttcctt   7200
atatgttgca gatactagac tcttatctga cacatggatt gcaaatattt tcccccattt   7260
tgtgtagtat tttcactttc tcaagagtgt ccatgagttc atttttatag aaaagataca   7320
ttctttttca ttaaaacaat ctgaacatat attgtcataa acacaaagtg attatctctg   7380
aatagattgt caatgttttg ttattttgga attaaccctg gcaatatttt tcaaggttag   7440
taatttcaca aattggtaaa tggaaagtga aagtttctaa ttcttagctc atgttattat   7500
gatgtgtgtg catcttggaa aggacccaag gtgtggaaca tgcagggatt tctgaacact   7560
caatcctaga ggtgggagtg ctatcacagt cccagaccca gctggtcagg tggaaagccc   7620
ccctgcccag cccacctcag ttcctcgggt catcatcatc ggcattgttt tgtttctgtt   7680
tctcactctg gggctgtcct gggaaaagga aaccgaaact gaagctgaat tagcctatgt   7740
aactctgacg tggtttgctc aggctattaa agggctgagc tgccagggct gaagagagcc   7800
gagagcagag aggcagccgc agccaaccag tgtctgcaga gagcctggca ccagaaccca   7860
cggccatggt gagtggtgag gcgggtttga caggtggggc tctgtattcc cctgcctggt   7920
ggcatctccc aggggaagaa tgcctactat gcacaggcag gtagagctac tcaaagcatc   7980
```

-continued cggttcccta agtgtgaggg gagggacagg gctctttcta aaatcagggt ctgggtcctg 8040
aaaggtggct tctgcccagc cgccaactct gagatccctt gggatcagca cagggcaggg 8100
gggtatttta ttggagagtt gacatgaaga ttgtgggtag tagctcttct gctcccttgc 8160
actctccagt gcctggggtc cccatctccg tgggtgggaa gggtggagag gagggagctg 8220
catccccggg gtctgacact cgtcccactg ccagtgctac acgtgcagta gtcccaggac 8280
ttctgaatct gtgtgatgcc cacagggcgg ggacctgacg gtgaagatgc taggggggcca 8340
ggagatcctg gtgcctctga gggactccat gacggtatcc gagctgaagc agttcatcgc 8400
ccagaagatc aatgtgcctg ctttccagca gcgcctggcc caccttgaca gcagggaggt 8460
gctgcaggaa ggggtgcccc ttgtcctcca gggcctgaga gctggcagca ccgtcctgct 8520
ggtggtgcag aactgcatct ccatcctggt gaggaacgac aagggtcgca gcagccccta 8580
tgaggtccag ctgaagcaga ctgtggctga gctcaagcag caggtgtgcc aaaaggagcg 8640
tgtacaagcg gaccagttct ggctgtcttt tgaagggagg cccatggatg atgagcaccc 8700
gctggaggaa tacggcctca tgaaggggtg caccgtgttc atgaatctac gtcttcgggg 8760
tgggtaggga agggccagga gggccttagg gagggctccc catgcagcgc agtgaataaa 8820
gttgtagcaa agccaaatgt gaagtgttca ttccaccctg gccagcaccc catgtcatca 8880
gccctccatt cggcaccctt ctggtgagat tgggggaagg gtggaggagg gagtgggtga 8940
ggggactcag ggtcactgag tggtcaccag gctagggtgg ccaagttaag ggacaaaccc 9000
tgtgggatca aaatggtgac cctctggaga aactgaagat gtgtccccac ctctttggga 9060
aattaacttc tagagaaata aaaagaggca ggtctgttga agcccatccc tgtcttccgg 9120
ttgagcctca gtcagccctg cacaactggt ctccaccttc acagctgggt cagcagatag 9180
cagagggagg gaaaaggcct ggctgggtcc caaaggccac acagtgagtg tccctggaag 9240
cggtgagggg ctgagtccct agggcctgcc ttggccagtg gtaagggagg ttcccccaca 9300
ccagctggag gctgagggcc tccaggaccc atcagaatac actgtccagc cttcattggt 9360
ctggagggaa ttggggactg ggccttgggc acacacatca ccattagggt gagctgctcc 9420
ttcagagttc acatcatgga agggccatag ccagcaggtg agggggcacc caggatgggg 9480
gttcctgttg ttcacatgga tgggagggga acaaactaca cctgcttcca cactagatgc 9540
ttctttctgt gccagtttcc caagtgagtc agccttggac agaatgcggt gggcagggag 9600
ggggacacag aacctatacc tcttgggcca aagtccatga ctctggggac actcagatct 9660
cagctttcgg actcttcagg ggcatttggc tggagaccca gaccccttct ttctgatctg 9720
tgggagtttg catctgagct gggggacccc caggtctggc ttgcctgtga cacttatgta 9780
gacacgcagg tgtgtgtgtg tgtgtgtgtg tgtgtgtgtg tgtgtgtgta gggggactcc 9840
tggctctagc ctcatttcct gggcccccac cctcacctct ttgtcatact gtaacttaac 9900
aagtgtgagc acgccctctc ggtgacaccc tcctttcttg aatcccctca gcagggtctg 9960
ggcgaggtag ggtccttctc caagatgcct ctgggctgct cacccttcat ggcctctggc 10020
tcagagatct gtggttggct tggatgaggg ggtgtgcagc agactcagcc ctggaggaac 10080
agaagggatc tcctctcctc ccattcccac catcttcagc taagtcgggc tctaatttgc 10140
acactctgga tctcagttta ccccctggac ccagcgggaa tggttggaga agtagcggga 10200
atggttggag aagagccttg ggggagctgg gaagggggcg tggctggccg tccatcgctg 10260
ctgctattcc cacctcagtc aacaggggga gcccgcagcc ctgcagaggg ccgggagccg 10320
acccgggatc gcgaggtggg cggggctgcg cttcgctgcg accaatcgcc gcagctccca 10380

-continued gcccgcattg gtccccggtg gccggtggtc ccgggcggcc gagcttccgt ccccagttcc 10440
tgtgaggggc taggatcccc cgtcaggttc ctctcgccgg gggaggggcg cagcccttta 10500
gggcgcgagg ggccgcaggg cctcggatct ggcagcccct tcttgcggcc agggagcccc 10560
cgccgcccca gccctggcgc agcctggagc cccttggaag tcccgtcacg tcgtctccag 10620
attatgcatt aacccgattt cagccgcatt tcctggcggg ggggcggggg ggtggaacgt 10680
ccgcgcgaac gggggagggg cgtccgtggg agtgcgccac agcagggaga gcaccctcga 10740
gcccgcccca accccgcccc tcggcctggc caggcccacc acccaccttg gccaaaccta 10800
gaccggcccc ctccctcccc cagccaggcc tccgcccggc gccgctttcc cggcgctttg 10860
ttcgcggctg ccgcgggtcg caggacgccg ggagggccgg gggcgggcgg gccggggggg 10920
tggggggtgg gggctggaag gggggtggtgc tgccccaagg cccgccccccg caccgcccgc 10980
gctcccgcca cctcccccga gctgcgtccc gtcctgtcca gtccagtccc cggcgcggcc 11040
cggtccgtgc gcttgctccg gccgccttcc gccgtcctct gcccgcgcca tggccagctt 11100
tcggccgttc agccgggccc tgctgcagcc tttgctgctg ctcctggtgg tggccgtgcg 11160
cgccctgccc agcgccgacg ggacgtgccc cgaacgcgcg ctggagcggc gcgaggagga 11220
ggcgaacgtg gtgctcaccg gcaccgtgga ggagatcctc aacgtggacc cggtgcagca 11280
cacatactcg tgcaaggtgg gcccccctggg gacccccggg accctgagcc ccttcagacc 11340
cttctagaag ccctggttgg gggcccttcc cccgcgatcc cggaccccta gcccggaggt 11400
cttcccgtcg cgatgccggc cgcgcgctga gacccccgtc ccgggacgtg ggaacgagcc 11460
ccagacgttc cgcagcacca gctccggctc ctgctccctt agcgaccgcc gacccccggt 11520
gggaggggtg gggggcgggt gcgggtctga gaaaactcgc gagcgccgga gggaaagttc 11580
ctgcggtgcc gctgcagtcc cgctcgcggt gcccgggccc tggagacccg atagtgtctg 11640
ctccttcacc ccaaacccac tcccttactg gaaacaagtg cgccccgccc cccggagaat 11700
gttcggctac cgcgcccccct ccccaccggc caaaggaaag gggacgaggg gaggtgacgc 11760
tttctgcttg ggatggaggt ggtgatttgg cctgtggtca gtgctgtcgc cctctccgca 11820
gaggtgagaa tgggtggtcc ggagagagag gaggggtgca cacctaatct cccaaccgcg 11880
ggggtcctgg tggggcttgc tgcagtgatg ggtgtggggc cagagcagag aagtgggcgg 11940
ggccgttgct gagcctcaag tgcggggggt gcagggcagg tgccccatcc gctcctggga 12000
gagctgtatc tcccctggcc ttagggagag gggccttgcc tggcctctcc ttcagttgaa 12060
tctgggagct cccggggtag gtctggtggt ttttttccca caatctgttc ctagggagga 12120
ctgaagggac ccaggcccct gcccctctct ggcccctaaa accacctccc tgaccagaaa 12180
tcggatcatt cctcttcctt ggagatgggg aggggtggca gctcctttca gactggcctg 12240
tgctgactac agctgggatc ccccgccagg ccccctcccc tccaccacag ccagggcact 12300
ttgccaagtc cctgcaggat tttcccgact tcctccccgc tgctcctggg tgtggctggg 12360
gtggggggag gcgatgaaag ccgcccagct ctcccctgct ggttattggc cttccagagc 12420
ctactctgta tctaggcatg gggggcgggg gaagagctgg cagccccacc atccctgggc 12480
cactggaggg tggagggagt ccctgtagat tttgcagacc caaggctccc agcaggggtg 12540
gccaggtgga cgggccactg ttgtctttca ctcctctttc cagaagtccc ggcccccata 12600
gatcctgaag aaaggggtgt tttttctcag ggacagcatt cccgggcagt ccccatgggc 12660
ctattccttt agggcagctc attctgcctg cagtgcctgt ggccctcctg cccccactgc 12720
cagtagtctg tgggcacccc cagggcttgg tttgtctgag caggtgccct cagggcccca 12780
agagcagagt gtggagggtg gggctgccct gtgctgccca aacttgattt tgtggttcac 12840
aggctgcctt ggcagcactc actgtaggag ccttgcagga ggaggggtct ttcacctcct 12900
ggctggaccg tgtcttagcc cacccacagg gctgcatgga gccaagctgg acaggagcct 12960
tgagctcaga gcccgtcacc ttgaaacttc atcatccatg ttagttgctc ctgactcttt 13020
ccagaggtgg gcccaagtac tgggtgggtt gacagggaga gtaaggtgtg gaaggctgtg 13080
aggtgtgaca tttagaactg gggtggctgg ggtcatctaa acctgagggt tagggagctg 13140
cttcttgagg gaaggggtgt gttctcaggc caggtatcct ggagtataac aagggcagtg 13200
gcgtctgtca tgtgtgtgtg cttccctgca gcttcctcct ggggggttgg ggcactgact 13260
ccacatatct gcccagggtt tgggtatact ccggacatct ggcctgagca aatgaggtgg 13320
gaaaagaagg aaaagtccag gcaccagtct ggtgtctgcc tctggcctct gtggccatct 13380
cccccgctcc acccagttag aagagaaccg ccgacaattg aacacccccct catgtccacc 13440
ctaggttcgg gtctggcggt acctgaaggg caaagatgtg gtggcccagg aaagcctgct 13500
ggacggaggc aacaaagtgg tgattggcgg cttcggagac cccctcatct gtgacaacca 13560
ggtgtccact ggagacacca ggatcttctt tgtgaaccct gccccgccat acctgtggcc 13620
cgcccacaag aatgagctga tgctaaactc cagcctcatg cgcatcaccc tgcggaacct 13680
ggaggaggtc gagcactgtg tggaaggtgt gtgtggggcc gagcagagca ggtgccttgg 13740
gggcagaagg gagcttgtcc taggctaggg cacatggcat cttgtggtcc gacctccttt 13800
tctgggtcct ggctccctgg tttcctggcc acctcagctc cagactctta acataagcag 13860
cactccccac cctggcccta gtgttgccac tatctgtcat cttggagtct cagacctgca 13920
aagggatagg cctcccattc ttccctccgc ctccccagct ctgcacgccc cttcctggag 13980
ttccctgttc taggaaagag gctggaacca ggtgaacgaa caccagttgt ttgtgttctg 14040
cagaagcccg aacacatgtc tagacggggc ccagatgttg agcctttggg gtggggctta 14100
aagattgtgc tggaggggag gctaccctgt tatgtgttcc cagaggcctg ccatttctgg 14160
gaagggacag ttatgtggag tgagctgctt ctaggagttt gaggggttgt gggatcccct 14220
gacagaggtg gagcatcttt ccttgtctgc tgtccccatg tgtctattct gaatggctca 14280
agagcaaccc tccctcacat gatggctcac ccatcccctt caccccagga gaatcccagt 14340
tgggggctga gatccttggc tgaggaatgt agcagggaga agtaggaact gcctgtcgcc 14400
ctcacatcct gtctgtcccc tcatggctgc ctggggaggg atgtatggga ggaggtggag 14460
agatcgcttc ctcccagggc agcaggaagg gtccctgact tcctgtcctg ggaaggcgac 14520
cctgtccctg tgacttgctc tgttggccgg tagggaagtt ccatcttcta cccaacttaa 14580
ctcctgtggt gctggcttgc ttttgtggga tcctggatgg tggactcatc tggcctgggg 14640
cagactgtgt gtgtgtgtgg cgaggtgtgg aacctgaagt ggagagccct gtagcatcct 14700
gctcggcctg cagtcatttg ctcctgggat tgcatctatg gtcctgatgc aacatcgcac 14760
agagatgcca gcagggctgt gtccctggtc ccttcccagc actagcatag ctgaggggtc 14820
ccagcatagc cctcccacca ggtgaggact ggagaccctg actgtgcttt ggaagcttta 14880
ctctagggga aatatgggag agtggcatgg agaggaggca ggttgtaggg tgtgatcccc 14940
agttttggag gatgagttgg agactaatga gaggtgggaa gaggggtcag gctgcagaaa 15000
atctgtttct gcaagatcaa gaagacaagt cattaactcc atagctggaa gggtctagtt 15060
cgagggtctg tggggtcaga gggcatgtgg caggggggcc accctaggca gaagagggtc 15120
tgccatcttg ccaggtccta ttctacccag gccaggccct ggctctggat atgtcagcct 15180

-continued

```
gggcacagga cccctggaaa ggagggtctg cagagagagc cccagtgag acttcatctg  15240
ctgtctgctg gctaccccgg atagggacca gtctaggccc ccagctccag ctgggccagt  15300
gtgggcatgg tggtggaggg gaggccccca gggagggagg gacccagaat gagaagcttg  15360
gggtccactg taaggctctg gggagccctg gaagttttga gccagtgaca cggatcccctt  15420
ctttggaagg aaagcagtgc cataaggggc agggggccag ggagagggta gattagatgg  15480
ggtgcctccc tctaaggatc cccaaagcct gaaggacaag gctcccagga gttggtgcca  15540
ggcttgagga agacacagcc ctcttcccac ctcccacagc agggagcagg caggagaagg  15600
gcctgcctcc cattctgtaa gcgatacctc ccattctgta agagataaag acctctgacc  15660
ccaccccagg ctctccaggg agccaagcct caccttagca tggggggtag ggttagggat  15720
gggccgagct tgagctacaa tgacctctca tctgaccctg accccttttct cttccttggg  15780
gccccatagc tgcccccgtc cctcagggcc ccgagtgaag gctgtgaagc tactgattgt  15840
ggaggtcacc ccaagacctg tgtctctatc acaaatgtcc cctgccccta aaaggcccac  15900
aggagccaag gtcaggggac acatcctgga ggcccacccc cctagatgcc cccacctcat  15960
ccccacctgg accctgcttc ctgcaggggt acctgttgct gggaggcata cctggtcccc  16020
agctccactg ggctcgcctt cctcagtttc tcccttaggg cctgcagggt cttcctggct  16080
ctgggcccct tccccaacct ccagtcccca ggaagctcct ccccaatcct ctgcctgggg  16140
agccacattc cgagcataac tgagacaggt atgtgtccct ccctctgcac cacttgtggg  16200
tgaaggagac tgcgggtttg ctccaggaag gaaggagacc ctcacgccct gctttgtcag  16260
ggaagtggcc tggcctcttc cagtgccagc tgcccacgca tcatgagctg cccaggctgg  16320
cagctgagcg ggcatctcct ccagcctttg gccactatac cctggtctgg acttgtacac  16380
ttgtacactc ccaccaccct cctctccccc acctaataaa gactggtcct tgggcccccc  16440
tgaattccct aggagggatg caggcttggg gtccttcccc aggcctttcc ctcccgaact  16500
ccgagccaag agcagagaaa ggaagtgttg tctgccctct ccgggcctgg cacaggaaca  16560
gggtcggaga gtctggcatt agtccagccc agccctgccc agtcctgaag ccgggggtcc  16620
tggtggccac agcctagact ggcctgcctg attccagtga gcaccctccc ttcctccctg  16680
ccacgctagc ctttgggcct tcacgccagt cttgggcctt tggggaaggt agtcctaggc  16740
tatatctcag gctagagaga tgctgggtcc cgggccgccg gccttggcct tggtgcaggc  16800
cctgtggcct gggagccgga tgtggacaca gacaccccca gacagggact ggctccgcag  16860
agcaaagcgg ggcaggtagg agcccagggc aggttccagg gctggcttcc tcagggctag  16920
agctggctcc ctctgctgtc tggcatttag cttctgtacc cccaagtcct gagcccgccc  16980
tactccccca cattcctccc tgccgagggg ggaggtggct tcttcctgtc cctgtttccc  17040
tcttccagac gtaagttctc accccacccc ctccagaccc gccccagtgc cgtcctcagc  17100
ccctccccca ggcaggtcct tggagctggg gcaggcccag gctggaggct gcgcgcctgg  17160
gctttctcct tccttccagc cactgggggc ggggcatctg ctcaggtgga gcgtggcctg  17220
ctcctgcact gtcctctctc acctagggtc cccggtagga agtctccgag agcatgggct  17280
tgtgggacca cagcgggctg gctgataccc tcactggggc ggccccagga gcttggggcg  17340
tggtgggggg tggggagggg gttgctgctg aaatcaaagg gcattggatc catcacttca  17400
aggcagtgcg ctcctttccc gcaggcctga gctggtggaa acagctcctg actttttcca  17460
gaccccaccc catcaccctg ctccccaccc agagaagagc cccgcctcc atactcccca  17520
gcagattgga aatggaaaaa aaaaaaagtt gttttgaaac tgtcctctcc cctgctgtct  17580
```

-continued gtacctgcct tccgcagggc tctggacaga gtagattcca gtggggcctg cctgtggaag 17640
gaaggcagag ccatggaggt gctcgcagcc tctctggggt gctgggaaga actggatcgc 17700
ctggtcaggg ctagctggtc tggatctggg gctctagccc cctgccccac caatcctttc 17760
agactgaggt agggagagtg cagagggtgg gatggggctg ccccaggtaa ggttagcagg 17820
ggcgtgagcc cagacttcag ggttgtagat ctagccaact gttgcttgcc ctgcacagcc 17880
tcctccagcc tgttttgctt ccttcttaaa gggttaatcc cccaatcccc tgagaatcaa 17940
agcctgcccc caccccatca ccacagtggg gtggaagaca gctgctgaaa ttgacctctc 18000
tcctgcccct gccccccaag tcctttgcct tcaccagaag gcccaggcca gctgccctcc 18060
ctcccagccc agaggcctga actgctctgc tggccccagc aaccccctca gcattgggat 18120
aggggaactg tggctcccca cacaggcccc tgaggcccag cccagcaagc tgggggctgc 18180
aggcacaatc cctgaagtag ccccaatagc acttaacact ccagagtccc aggaagcgcc 18240
cacctctcac aaagagaaaa agggatctca gaaatgagag ttagtgacag ctaccctgat 18300
gagattgacc cagctcatca gagagtactg tgtccccata ggctacaggg ggctcaggag 18360
ggatctgggc cctattctag gctgtggctg ggaaccgggg aggggtgacc tggcctctgg 18420
tggagcttcc aatggggagg gaagctcccc tcaaaggggc ctctccctcc agagcagatc 18480
ctgagaactt cctctgagga aggccccctg ctaggggctg cttacagctg gacctgggaa 18540
ggggaagatg gtccctccca cctcccctcc cactgaggca tgggaggggc aagctctctt 18600
tcctcacagg cagccggctg tttccagctg tgtggcctgc acatgtgtgt gtgtgtacat 18660
ttgtatgcac gtgtgcctgc aacctcaggt gtaccaacca ccacacaaca gttctggttg 18720
aaactccagc tggtggcctg tggttcctgc cacccttgta tcgcaggact cagcctgggg 18780
aggggaccct gcagatgctc tgccaatggg atggtagccg gcaaccttgg cttgtgtccc 18840
agagttctgg gaacagggct gtgggccctc tgtgggtgcc gtctcctgcc tgctgcccca 18900
gtgtccagct gtgctcccct cccaccaccc catccccggc agagagctgg gcccctgctc 18960
ctgtgggctc tgccgctggg tttctcaatg ccagagatgg aagggctgca ttgaacagga 19020
agagtccctg ggatcacttg ggttccctgt cccctcacgc ctgctggacc ctgtgtctgg 19080
ctaagttagg gagcagggca ggtcaggaga ggtgggtctg cctttgatgt gaggtgggcc 19140
tgaagctccc tacctctcct cttagcaact tcctctgcac tgccccctct gcataccagg 19200
cccagaagca ggcaacctgt tgtggctccc tgaggcacct gtccctctgg caacaggtac 19260
atgatttcta tgtacattgg ggagaaataa aggcacaaca tctgggccag attatggcct 19320
gtcctgaccc acaagtgggg aaaggatgta tgtccacccc tgttcctaga ggggggg aag 19380
tgaagcttgc tagagtccac tcgtgaatcc agccatcagt tccttcctca cccacccgtc 19440
cacgcaggac ctagcagcag gccctcacag gaccactaga agggctgctg cagctaccca 19500
cgcggctctc tcctgtctgg tcggtctttc tgtccctttg ttcccagctt ctcttggttc 19560
caatgttgta gccatgcgtt ctgggaaaca cactcactca gaagcacaat gcaaataacg 19620
gagtgcagtt tattacaccg gcgggcccaa ggcagagtct cctcttagcc aaggaccccg 19680
accagttttt ctgaaaacct tatataccct aagtgtacgt gcccaaaccc acctccccaa 19740
attccctgaa actagtctga acagaggaaa agaaagatac agtcaaagtt aacctgtgat 19800
tcatatgcct taagcctagg tagttaacag tggaccatta ttaataggcc tgtgatcata 19860
ccccaataag cataatagaa tttatgattc tatgcggtta cacagataat tagggtattc 19920
tttaggtaac agagagtcta ggaacgagcc ctggggctct tccatccgga ggggtctggt 19980
tttccagttg gtgtgtcgtt tccatagata ctgggcatat agctcaaagt ccacagtccg 20040
gcccaagatg gagtcctgct ttcaagatgg agcctggtct gtctgtttcc tccttcatcc 20100
ctcctcttca tgctcttaac tcatagtatg agcatcattc atagggattt attgcaccct 20160
gactctccga cctccaattt gggagaacga catcaacctt tgggttacag agttcataat 20220
acattgtaaa ataaagggtc cacaaagcag aactatgaag gcaactataa caatggtaaa 20280
tatagttttc caccaatcac ccttcaccca acataggacc gaagtccaaa aaggaagatg 20340
tatcagacat aacttttacc tgacctttca tgtcatctag ggtagctgat ctatagccag 20400
ataaatcagg aatatacaca caacattcaa ctttaattat agcacaggtc cctctttgta 20460
ctgaaactgt ggtcaatctc aagatgatag cagcaagtcc ttgtagcagc agttgattgt 20520
agagcttcat ctctgtttct tctttaagat gatcttggtt tcatggggat cagaggggtc 20580
cctctgcaca gtccactcgg cgtcctccgg gtctgcatgg tatgctctct tcagcctcat 20640
gtggaggatc cagggagtga cacctgcaac tttaactgca gtagggctgg ttagaacaac 20700
agcatatgga cccttccaat gtggggccaa ggagtcgtgt ttccagtcct tgaccacacc 20760
cgatccctgg gcacaaattc gtgaatctgt tccccaaggg ggaacggcac cttttcttgt 20820
acaaacttag ttacctgatt tattacctta cccagttgtt ccatctgctg tgaaatctca 20880
tctcccctta cctgaggcaa atttgttgac acctgtttta ttatgggagg gggcctccca 20940
tacacaattt tgtacagaga cgattcatgg gactgtgggg tcatcctgag tctgagcaga 21000
cccgtcagaa acaagtccac ccaggaaccg tcagtctcca agatccactt ggagagtgtc 21060
tctaagtgtc cggctggttc cttccaccat cccagaactc tggggcctat atgctgtatg 21120
taatttccac ttgatgttta aagttttgct tacttggtta tactaaaaca gctacaaaag 21180
ccgggccatt gtccgatcca atgctggtag gaaatccaaa tctgggaact atctccctaa 21240
gcaggcaccg ggctactttt gatgctcttt cagtgagggt aggaaaagct tctacccatc 21300
ctgagaacgt acatactgtg accagcaggt aatggtagtg tccgtgaggt ttcatttcag 21360
ggaagtccac ttccaggtgt tcaaagggca gcgtgccttt tacctgaatc cctgcaggtt 21420
tctgtctgtg ccaacaggca gcattggcct gtaagcaggc agtgcagttc tgagattttg 21480
tcctgcatgg ggaagagagg aggggaacaa agaaatagtt tcaaattatc tcttccagtt 21540
tatcatggca tagatgggtc gcttggtgtg tttggcttac cagagtgggt gccagctcct 21600
ccggtaccca taatttgcca cttggcaatt cccactatcc cttttcagtc ttgatggccc 21660
cttctgcttt ggctagttgg ttttgagctt cagtgtattt tggagagtct agtgttagct 21720
caggtagctc cgccaatatg aaagctttaa caggggcttc acttgtcacc cccaagccct 21780
tggctgcttg tttagcggtc ttatctgcca gtctgttccc tgagcccggg gagtatcctc 21840
tttttgacgt tctcagcagt gtatgactgc aatcctttct ggttcccagg cagcatctaa 21900
tagggtctta atttcttcct tattttttat ctttttcact agctgtcaaa ggcctctctc 21960
cttatacaga gccctgtagt gtggcaaaag catacctgga gtctgtgtca aggtttgtct 22020
tcttaccttt tgacagctgg agggcctgga ttagagcata tagttcagcc tgttgaatgg 22080
agcagtgtgg tggcagagag ggagcctcaa caatggtttc ttctgtgacc actgcatatc 22140
ctgacagtca ttgtccttgt ttcaccaggc tggtgctatt ggtgtacacg accgaatctg 22200
ggtccgggat tggctggtct ctcaagtcag gtctgctggc atatttcctt gcgatcatgt 22260
gagggcccac cttctcccac aggaaggaga gtggccagat tcagggcctg acaaggctca 22320
gtagtaacat gggggttctc acataacagt ccctggtact gagtaatctg ggatgttgac 22380

-continued

```
agccatttat ggaggtcccc ttgcaggaga gtgttgacct catgtgggac ttttacaaac  22440
aaatcttggc ccaaagtcag cttggttgca tcctggacca gtaaggcaac tgcctgtaag  22500
catcccagcc acccagtagc aacactgtcc agctgattag aggtaagtca caggtctgtc  22560
ccatgtcccc atagtctggg acaacactcc tatagccacc ttgtcctttt cagtcatgta  22620
aagagtaaat ggcttagcaa ggtctggcag gcccaaggcg ggtgctgatg taactgtact  22680
gggtttgagt tttattacca ctgggacttg ttttgcaagc ctgggggggt tgtcttctgc  22740
ccagacctca gggaattgtt gagttaactc tctctcttga ccattgagcc tgtccggttt  22800
cccttctggg agatcgtgca atctcccttc atcttgaggg gttactgaga ggaagagtaa  22860
ataggtggtt aagcccactc gaacagtggg tctttcttgg ggagacagtg acttgttccc  22920
ccaatttaga cagcaagtct cttcctaaca aaggtactgg gcattcaggg atgtataaaa  22980
actcatgagt cacttggtgt ccccccatct gacattttca gggtaggcta gagacacaag  23040
gctgcattta tcaccatctg agacccagca gcctctggct gggtctattg gcgtataaag  23100
tctataggcc tcgcatagtc tttcgcagaa ctcagggtga ttcgctttcc ctttgaatca  23160
cttcagaggg ttttgtgata cttatagctt ttcgggcccc cctcttgaga ccttgtaaaa  23220
tagccacccg ataactctcc aggtggcccc tcccttcctc tgtgttacag tcccagttgg  23280
gcctctcatc cggggtggct agttctgccc accgctgcgg gtttgcggta ccctcaggtg  23340
ccatttcgga gaaggcaatg gca                                         23363
```

<210> SEQ ID NO 5
<211> LENGTH: 23363
<212> TYPE: DNA
<213> ORGANISM: Bos taurus

<400> SEQUENCE: 5

```
ggagaaggca atggcaaccc actccagtac actcgcctgg aaaatcccat ggatggagga     60
acctggtagg ctgcagtcca tggggtcatt gagagttgga caagactgag cgacttcact    120
ttcacttttc actttcatcc attggagaag gaaatggcaa cccactccag tgttcttgcc    180
tggagaatcc tagggacggg ggaacctagc aggcggccat ttatggagtc gcacagagtc    240
ggacatgact gaatcgactt agcagcagct agttgcaagt ccagaggagg aagtggcatt    300
cccagaatgg aaaggaacca cagggccaag ggaggagggg ccgggacagg tgggaaccag    360
gctctagtgg cttcaggtcc ccagaggggt ctaagagagt catgcttggc ttttctgagc    420
agcagagtgg cccaactggc agctcggaag ggccacctcc cacactacat tctacctggt    480
gggtggcgat gctggctggc ccccacctca ataccctttc ccaggggtcc agtctggggc    540
ccagtgcaga cgcctgtgat gcaggtttga tcactgggtg ggggaagaca ccctgccccc    600
tccccggagg aggaaatggc aacccactcc agtattcttg cctgggaaat cttatggaca    660
gcctggaggg ctacagccaa aagggtcaca aagagtcaga cacaactgag caactgaagg    720
aaggaccctc ctgtacctgt ttcctcacct gtaaaatggg ctaccttttc atttagccct    780
ggactatagt ccatggggtc gcaaagagtc gaacatgact gagcaactaa cactttcaca    840
ctttgactga gaagataaat gagatctgat tttgaaagca cccagcacat gcaagcggga    900
cagagtcacc tggattcacc tctgccacaa gccccactgt atcctctacc ctctgagaca    960
ccctctccct acctggggtc ttcagaagcc tgtttcttgg cccttccagc cccaacaagg   1020
agccttctct cacccagagc agagtgagtc ccaggggtgt catctacatc cctgtgtcct   1080
tcccactggg ctgcaccccc actctctctc tgggccctcc tacctctggc tgtcccctcc   1140
```

-continued

```
ctgcctttta catctggatt tgatctctgg taggacctgg gactcctggg gaccgtaggg   1200
gctcccttgc tctgagtaga gagggagagt cctaggctgc agggggggaaa ctgtgctgag   1260
aaatactgac gtggaacact gcattttcca aagatggcta caatacatcc accccaaata   1320
ctctacctgt gtgtccttgg tgagattttg tgatgacatt aaccagcaaa gacaggggca   1380
gtggtgatct atgaattctg aggcttgact tgaaaaacgt gcaccttgct gtcctgggaa   1440
actcactcct ggaaaccact gacccctctg tgaggaaacc cgaactggtc tcatggaaag   1500
gcctcatgga gaggccttgt ataagtgttg agctaggaac ctagaaatct cagcttccag   1560
acaggtgatc ccaacctgcc gcttcagagc cccactcac actttcccag ccagctctgt   1620
gtgctctgtt ccactcttga ttcacatgac tggtgttact gtgacacttt ggggtcattc   1680
gttacgaaac aatagtaact ggaacagcta agatggccca agccctggac ccaccccccct   1740
ccccagcccc accccccaaa ccttgttcct tcctttctct ggcattcaca gagtcacagg   1800
agcttcccgc actggctgtc catctgacga ggtgactttt gcagctatcc aaggccaact   1860
atctgtcctc ctagatccag gcttgagttg gccaagtccc agtaggctga tggtcccagg   1920
ggcatctcta gggaccactg ttggccactg ggcaggaaaa gtagtggggg agtctgtgtg   1980
ggaagataag tgtattttcc agtccagaca ctgggctgca gccttggtgg ggggtggggg   2040
gatggtcttt ctcacgtctg gctcccatga cagcattcca caacattcag acagtgtccc   2100
tccggggcct gccaggtgct gtctgtgcac aggcccctcc caacctctga cagggggggtg   2160
gcacctgcac ttgcaccctg cccctcagca ttccacaggc acatgggtcc ctgaatatca   2220
gagacaccat agaccatgac cagcaacccc atcctcctgt tccctcctct tctgccaagg   2280
gacaacaggc tgtggactca ggcagccagg accagagttg ccatgtgacc aggctagagt   2340
cattgcaggg tctctcctgg agcatgggag ttgggtcctg agatgataaa gtggcagagg   2400
ctagggctgg aggaacccag gattcagtat agagaagaag gaagcagatg accaggaccc   2460
taatcttaac cctgaggggg catctttcat ttttacaggc cagcggacca agacaccttc   2520
cttcggctct tggtgctggg cagttggagc atcccccaa cacctgatgc atgacagcac   2580
ctcccccgag gtctgggcat tgtcaacatc tttctccatt attgaatgtt gacacctctc   2640
cacgctgggg aagccatgtc tccccaattc tgtgtggtaa cagagcttcc caccctgtct   2700
gcctgtgatg ccacctccct gtgggcttcc atgggtgctt ctctctccag tctccttgga   2760
ccactactct ctggagaggt atgctttgct ctcctgctgg tcacatccag actagtttct   2820
tcttcaccaa aaaaagtccc agctttgaac ctcatcttat taacagatct catcttgtga   2880
agtccactgc aaccctgcgg ggggggggcc tccccatacc ttctgaaggt tcactcctga   2940
ttccctgtca ctttctccag cggctcctgt cacagtcctt gttgacttcc aaattcacac   3000
ggttgatctt ctggacttcc tggcctccat ggggcatcct agtgtagagt tggcaactaa   3060
gcttccaatc ctaagtgctg ggtgtagact gtagccgtaa tattcccatc caccctggag   3120
gacacgccca ccaggaagcc ccgcccacag ggcacaggtc agcatctgca gtacaatatc   3180
ctgctgcttt cccagtgtaa cctggggtcc tgcctcctcc ctccacactc tcagcctctt   3240
gtctcaggtt ctgcctcccg cttctccttg tgcctttcag tcctgtggaa cttggggaac   3300
aagtcttcac tctaatcttt ctatccacac aactggagca ctctctgccc agtggtggag   3360
cctgactgag gcaccagcct cctctgaatc tgactattct cagttctcag accagattct   3420
gccatcgtcc tcgaccctca gagttcactc ccagtgctgc tctggcaggt cctacagtgg   3480
ctctatctcc ctgatgtata caaacaccta cttctgacct attgcttttc caccactggc   3540
```

-continued

```
tgcaagccgc caccagcttc ggcctggaat tttgtagttc tttgccatgg caaggcagcc   3600
agtcttggag ccgagtgctc aatgggggca ggtggacagg agaggagatt agagggtcag   3660
cagagtggtc agaagaacaa gcctaagctc ctatcttctc tcggaagctt atgggaagcc   3720
atgggagaga aggttgtgtg tagatcactc tggcccttgg ctccaccaca gattatgggg   3780
tcaggataga agcacagcca ctcggctgta tccatagcag cctcagtgga cgagggcgca   3840
tagatataag tgaggtcatg gatattcttg ggagtttttt gttgttgcta ctgctgttag   3900
atggctgaag ggcttaaaaa taaaagcaag tgtattaaac gatatagata ctgttttaaa   3960
agttttagga agtttaagtt agtttgtaaa tgaaaccaaa tattaaccaa agaccccttt   4020
ataagtagcc attgtaactt cataaatagg atattcaggt ttttgtctag aacatatgta   4080
ttttgtgatc atgttgttag gtgcatacaa attaaaaata atttcatttt atcagtgagc   4140
tcaacctttt attgttatgc aaccttctgt atctagtaat gctttgacta taaggtttct   4200
ttgttaatct gttagtgaaa ctgttaatac ggtcacatct gcttcccttt agttaacatt   4260
acgcagtagg tttcttttct ccttttactt tcagtttcct gtacctttat atttcatatt   4320
atttatgtct tctgtaagct gtgtaaaatc agattatttt taatcaggct gacaatcctg   4380
gtcatttagt ccccctggat ttcagacctc tgctctttag aactgtgagg gaatacattt   4440
ctgttgtttt aagccaccca gtttgtggtg gcttaaaagc ctccaagaca cagagacatg   4500
cttccagggc tatcgttttg cctgccgaaa gcctttgcat ctagttcctc ttgtccaaag   4560
caggtgatat tcaataaagt aataaaagaa aataaaggtt ctattactat atataccata   4620
tttttgttat ctttttaaaa ttttttatta cttaaaattt ttttgaattg ttgtttcatt   4680
cccttatctt tgtgccatat ttaataatgg tcacctaggg actttcctgg tggtccagtg   4740
gttaagactt agtgcttcca atgcaagggg catgggtttg acccctaatc agggaactaa   4800
gatcctgctg gctgcatgcc atgcccgaaa aaaacaaaac aaaacaaaac aaaaaacaga   4860
atcaaaataa tggtttttg aagaagacag ggattttcac attctgtaat atttgttttg   4920
tttgtggctt tctttttata atactaatat tatttatgca aggaatgagt caagttagaa   4980
atttagaata atataaacaa tatttaaact gttttatgca tgttaacaac tttggtgcct   5040
tatgattatt tggggggaat tgatggaatg attaattcat atgaaaacaa tttggttttc   5100
cccattcctt ttatttattt aaaatttgtt tatttagttt aaaatttatt tttaaaatat   5160
ttaattattt ttaggtattt atttttattt tatttattta ttttggctcc atcttgtggg   5220
atcttagttt cccaaccagg gatggaacct gtgctcctga agtgaaagta tgaagtccta   5280
accactggac tgccagggaa ttccctaagt atttattttt atttttagct aacatatgcc   5340
tgagatgtgc tgtttgtaat agtaaaaatg tgggaacaac caatatttat ttaaaaatat   5400
gagactggtt aactaaatta cactttattc tataatggac tttgttgcta tgggcaacaa   5460
atgcacatat gcagccatta aaacaacttg cataaaaata tgagggctta caaatagctg   5520
agaaaagaag agaagctaaa ggcaaaggag aaaaggaaag atatacccat ctgaatgcag   5580
agttccagcg actatcaagg agagataaga aagccttcct cagtgatcaa tgcaaagaaa   5640
acaatagaat aagaaagact agagatctct tcaagaaaat tagagatatc aagggaatat   5700
gtcatgcaaa gatgggcaca ataaagggca gaaatggtat ggatctaaca gaagcagcaa   5760
aagaggtggc aagaatacag agaagaacta tataaaaaag atcttcatga cccagataac   5820
cacgatgatg gtgtgatcac tcacttagag ccagagatcc tggaatgcaa agtcaagtgg   5880
gccttaggaa gcatcactat gaacaaagct agtgtaggcg atggaattcc agttcagcta   5940
```

-continued

```
tttcaaatcc taagacatga tgctgtgaaa gtgctgcact caatatgcca gcaaatttgg   6000
aaaactcagt agtggccaca aaactggaaa aggtcagttt tcattccaat cccaaagaaa   6060
ggcaatgcca aagaacgctc aaactaccac acatttgcac tcattttctc acacactagc   6120
aaaggaatgg tcaaaattct ccaagccagg catcaacagt acaggaatca agaacttcca   6180
gatgttccag gagttggtga tggacaggga ggcctggcgt ggtgcagtct ttgagtcatg   6240
gggtctcaaa gagtccaaca cgactgagcg actgaactga actgtgaatg aagcagggta   6300
caaaatgttg agagtagcag gaggattttt tttttcaatt ttcttttta ttgaggtgaa   6360
gctcatgtaa cataaactta accattttat agtatataat ccagtggcat ttagtatatt   6420
tagtccaacc atcacctcta tctagttatg aaacattttt attattccca aaggaggcct   6480
tagctccatg aagtgtctct cctcatgcct cctccccgca gctcttggca attactaagg   6540
tattttcagt ctctatggac ttgcctcttg tggacatttc atatcagtcg aatcacatgc   6600
tttgtgtcct gtgtctgtta tttgtcactg agctccattc acaccgcagc ctgtgtcagt   6660
gctccatcct tggttatggc tgaggagcat tctactataa ggaggcacca cactttgtgc   6720
ctccagctgc tgatgggttt ggttccaccc cccatttcaa ccattctatg actagagctg   6780
ctgttaacat ttgggtgtga gcatttgttt gaacacctgt tgtcagttct gtgggcatac   6840
cctagttgtg gaattgctgg gtcatatgaa aattctattt aacctttga ggaatgacta   6900
gactgttttc cgcagtggct acatcatttc acaatcccat cagcaatgta tgaagattcc   6960
attttttga catcttcacc aacacttatt attcactttt taattattat tatattcatg   7020
ctagggggtg tgacacagta catctggttt tgatttgcat ttccctggtt cccatcattt   7080
ccaaagatgt tgaacatctt ttcatgtggc tcttggccat ttatgtattt tctattttaa   7140
aatgtctatt taagtcattt gcccaacttt taattgagtt gcttatcttt tagttgttaa   7200
gttgtaaaag ttccttatat gttgcagata ctagactctt atctgacaca tggattgcaa   7260
atattttccc ccattttgtg tagtattttc actttctcaa gagtgtccat gagttcattt   7320
ttatagaaaa gatacattct ttttcattaa aacaatctga acatatattg tcataaacac   7380
aaagtgatta tctctgaata gattgtcaat gttttgttat tttggaatta accctggcaa   7440
tatttttcaa ggttagtaat ttcacaaatt ggtaaatgga aagtgaaagt ttctaattct   7500
tagctcatgt tattatgatg tgtgtgcatc ttggaaagga cccaaggtgt ggaacatgca   7560
gggatttctg aacactcaat cctagaggtg ggagtgctat cacagtccca gacccagctg   7620
gtcaggtgga aagcccccct gcccagccca cctcagttcc tcgggtcatc atcatcggca   7680
ttgttttgtt tctgtttctc actctggggc tgtcctggga aaaggaaacc gaaactgaag   7740
ctgaattagc ctatgtaact ctgacgtggt ttgctcaggc tattaaaggg ctgagctgcc   7800
agggctgaag agagccgaga gcagagaggc agccgcagcc aaccagtgtc tgcagagagc   7860
ctggcaccag aacccacggc catggtgagt ggtgaggcgg gtttgacagg tggggctctg   7920
tattcccctg cctggtggca tctcccaggg gaagaatgcc tactatgcac aggcaggtag   7980
agctactcaa agcatccggt tccctaagtg tgaggggagg gacagggctc tttctaaaat   8040
cagggtctgg gtcctgaaag gtggcttctg cccagccgcc aactctgaga tcccttggga   8100
tcagcacagg gcaggggggt attttattgg agagttgaca tgaagattgt gggtagtagc   8160
tcttctgctc ccttgcactc tccagtgcct ggggtcccca tctccgtggg tgggaagggt   8220
ggagaggagg gagctgcatc cccggggtct gacactcgtc ccactgccag tgctacacgt   8280
gcagtagtcc caggacttct gaatctgtgt gatgcccaca gggcggggac ctgacggtga   8340
```

agatgctagg gggccaggag atcctggtgc ctctgaggga ctccatgacg gtatccgagc 8400
tgaagcagtt catcgcccag aagatcaatg tgcctgcttt ccagcagcgc ctggcccacc 8460
ttgacagcag ggaggtgctg caggaagggg tgccccttgt cctccagggc ctgagagctg 8520
gcagcaccgt cctgctggtg gtgcagaact gcatctccat cctggtgagg aacgacaagg 8580
gtcgcagcag cccctatgag gtccagctga agcagactgt ggctgagctc aagcagcagg 8640
tgtgccaaaa ggagcgtgta caagcggacc agttctggct gtcttttgaa gggaggccca 8700
tggatgatga gcacccgctg gaggaatacg gcctcatgaa ggggtgcacc gtgttcatga 8760
atctacgtct tcggggtggg tagggaaggg ccaggagggc cttagggagg gctccccatg 8820
cagcgcagtg aataaagttg tagcaaagcc aaatgtgaag tgttcattcc accctggcca 8880
gcaccccatg tcatcagccc tccattcggc acccttctgg tgagattggg ggaagggtgg 8940
aggagggagt gggtgagggg actcagggtc actgagtggt caccaggcta gggtggccaa 9000
gttaagggac aaaccctgtg ggatcaaaat ggtgaccctc tggagaaact gaagatgtgt 9060
ccccacctct ttgggaaatt aacttctaga gaaataaaaa gaggcaggtc tgttgaagcc 9120
catccctgtc ttccggttga gcctcagtca gccctgcaca actggtctcc accttcacag 9180
ctgggtcagc agatagcaga gggagggaaa aggcctggct gggtcccaaa ggccacacag 9240
tgagtgtccc tggaagcggt gaggggctga gtccctaggg cctgccttgg ccagtggtaa 9300
gggaggttcc cccacaccag ctggaggctg agggcctcca ggacccatca gaatacactg 9360
tccagccttc attggtctgg agggaattgg ggactgggcc ttgggcacac acatcaccat 9420
tagggtgagc tgctccttca gagttcacat catggaaggg ccatagccag caggtgaggg 9480
ggcacccagg atgggggttc ctgttgttca catggatggg aggggaacaa actacacctg 9540
cttccacact agatgcttct ttctgtgcca gtttcccaag tgagtcagcc ttggacagaa 9600
tgcggtgggc agggaggggg acacagaacc tatacctctt gggccaaagt ccatgactct 9660
ggggacactc agatctcagc tttcggactc ttcaggggca tttggctgga gacccagacc 9720
ccttctttct gatctgtggg agtttgcatc tgagctgggg gacccccagg tctggcttgc 9780
ctgtgacact tatgtagaca cgcaggtgtg tgtgtgtgtg tgtgtgtgtg tgtgtgtgtg 9840
tgtgtagggg gactcctggc tctagcctca tttcctgggc ccccaccctc acctctttgt 9900
catactgtaa cttaacaagt gtgagcacgc cctctcggtg acaccctcct ttcttgaatc 9960
ccctcagcag ggtctgggcg aggtagggtc cttctccaag atgcctctgg gctgctcacc 10020
cttcatggcc tctggctcag agatctgtgg ttggcttgga tgagggggtg tgcagcagac 10080
tcagccctgg aggaacagaa gggatctcct ctcctcccat tcccaccatc ttcagctaag 10140
tcgggctcta atttgcacac tctggatctc agtttacccc ctggacccag cgggaatggt 10200
tggagaagta gcgggaatgg ttggagaaga gccttggggg agctgggaag ggggcgtggc 10260
tggccgtcca tcgctgctgc tattcccacc tcagtcaaca gggggagccc gcagccctgc 10320
agagggccgg gagccgaccc gggatcgcga ggtgggcggg gctgcgcttc gctgcgacca 10380
atcgccgcag ctcccagccc gcattggtcc ccggtggccg gtggtcccgg gcggccgagc 10440
ttccgtcccc agttcctgtg aggggctagg atcccccgtc aggttcctct cgccggggga 10500
ggggcgcagc cctttagggc gcgaggggcc gcagggcctc ggatctggca gccccttctt 10560
gcggccaggg agcccccgcc gccccagccc tggcgcagcc tggagcccct tggaagtccc 10620
gtcacgtcgt ctccagatta tgcattaacc cgatttcagc cgcatttcct ggcgggggg 10680 cgggggggtg gaacgtccgc gcgaacgggg gaggggcgtc cgtgggagtg cgccacagca 10740

-continued

```
gggagagcac cctcgagccc gccccaaccc cgcccctcgg cctggccagg cccaccaccc  10800
accttggcca aacctagacc ggccccctcc ctcccccagc caggcctccg cccggcgccg  10860
ctttcccggc gctttgttcg cggctgccgc gggtcgcagg acgccgggag ggccgggggc  10920
gggcgggccg ggggggtggg gggtgggggc tggaaggggg tggtgctgcc ccaaggcccg  10980
cccccgcacc gcccgcgctc ccgccacctc ccccgagctg cgtcccgtcc tgtccagtcc  11040
agtccccggc gcggcccggt ccgtgcgctt gctccggccg ccttccgccg tcctctgccc  11100
gcgccatggc cagctttcgg ccgttcagcc gggccctgct gcagcctttg ctgctgctcc  11160
tggtggtggc cgtgcgcgcc ctgcccagcg ccgacgggac gtgccccgaa cgcgcgctgg  11220
agcggcgcga ggaggaggcg aacgtggtgc tcaccggcac cgtggaggag atcctcaacg  11280
tggacccggt gcagcacaca tactcgtgca aggtgggccc cctggggacc cccgggaccc  11340
tgagcccctt cagacccttc tagaagccct ggttgggggc ccttcccccg cgatcccgga  11400
cccctagccc ggaggtcttc ccgtcgcgat gccggccgcg cgctgagacc cccgtcccgg  11460
gacgtgggaa cgagccccag acgttccgca gcaccagctc cggctcctgc tcccttagcg  11520
accgccgacc cccggtggga ggggtggggg gcgggtgcgg gtctgagaaa actcgcgagc  11580
gccggaggga aagttcctgc ggtgccgctg cagtcccgct cgcggtgccc gggccctgga  11640
gacccgatag tgtctgctcc ttcaccccaa acccactccc ttactggaaa caagtgcgcc  11700
ccgccccccg gagaatgttc ggctaccgcg ccccctcccc accggccaaa ggaaagggga  11760
cgaggggagg tgacgctttc tgcttgggat ggaggtggtg atttggcctg tggtcagtgc  11820
tgtcgccctc tccgcagagg tgagaatggg tggtccggag agagaggagg ggtgcacacc  11880
taatctccca accgcggggg tcctggtggg gcttgctgca gtgatgggtg tggggccaga  11940
gcagagaagt gggcggggcc gttgctgagc ctcaagtgcg gggggtgcag ggcaggtgcc  12000
ccatccgctc ctgggagagc tgtatctccc ctggccttag ggagaggggc cttgcctggc  12060
ctctccttca gttgaatctg ggagctcccg gggtaggtct ggtggttttt ttcccacaat  12120
ctgttcctag ggaggactga agggacccag gcccctgccc ctctctggcc cctaaaacca  12180
cctccctgac cagaaatcgg atcattcctc ttccttggag atggggaggg gtggcagctc  12240
ctttcagact ggcctgtgct gactacagct gggatccccc gccaggcccc ctcccctcca  12300
ccacagccag ggcactttgc caagtccctg caggattttc ccgacttcct ccccgctgct  12360
cctgggtgtg gctggggtgg ggggaggcga tgaaagccgc ccagctctcc cctgctggtt  12420
attggccttc cagagcctac tctgtatcta ggcatggggg gcgggggaag agctggcagc  12480
cccaccatcc ctgggccact ggagggtgga gggagtccct gtagattttg cagacccaag  12540
gctcccagca ggggtggcca ggtggacggg ccactgttgt ctttcactcc tctttccaga  12600
agtcccggcc cccatagatc ctgaagaaag gggtgttttt tctcagggac agcattcccg  12660
ggcagtcccc atgggcctat tcctttaggg cagctcattc tgcctgcagt gcctgtggcc  12720
ctcctgcccc cactgccagt agtctgtggg cacccccagg gcttggtttg tctgagcagg  12780
tgccctcagg gccccaagag cagagtgtgg agggtggggc tgccctgtgc tgcccaaact  12840
tgattttgtg gttcacaggc tgccttggca gcactcactg taggagcctt gcaggaggag  12900
gggtctttca cctcctggct ggaccgtgtc ttagcccacc cacagggctg catggagcca  12960
agctggacag gagccttgag ctcagagccc gtcaccttga aacttcatca tccatgttag  13020
ttgctcctga ctctttccag aggtgggccc aagtactggg tgggttgaca gggagagtaa  13080
ggtgtggaag gctgtgaggt gtgacattta gaactggggt ggctggggtc atctaaacct  13140
```

```
gagggttagg gagctgcttc ttgagggaag gggtgtgttc tcaggccagg tatcctggag  13200
tataacaagg gcagtggcgt ctgtcatgtg tgtgtgcttc cctgcagctt cctcctgggg  13260
ggttggggca ctgactccac atatctgccc agggtttggg tatactccgg acatctggcc  13320
tgagcaaatg aggtgggaaa agaaggaaaa gtccaggcac cagtctggtg tctgcctctg  13380
gcctctgtgg ccatctcccc cgctccaccc agttagaaga gaaccgccga caattgaaca  13440
ccccctcatg tccaccctag gttcgggtct ggcggtacct gaagggcaaa gatgtggtgg  13500
cccaggaaag cctgctggac ggaggcaaca aagtggtgat tggcggcttc ggagaccccc  13560
tcatctgtga caaccaggtg tccactggag acaccaggat cttctttgtg aaccctgccc  13620
cgccatacct gtggcccgcc cacaagaatg agctgatgct aaactccagc ctcatgcgca  13680
tcaccctgcg gaacctggag gaggtcgagc actgtgtgga aggtgtgtgt ggggccgagc  13740
agagcaggtg ccttgggggc agaagggagc ttgtcctagg ctagggcaca tggcatcttg  13800
tggtccgacc tccttttctg ggtcctggct ccctggtttc ctggccacct cagctccaga  13860
ctcttaacat aagcagcact ccccaccctg gccctagtgt tgccactatc tgtcatcttg  13920
gagtctcaga cctgcaaagg gataggcctc ccattcttcc ctccgcctcc ccagctctgc  13980
acgccccttc ctggagttcc ctgttctagg aaagaggctg gaaccaggtg aacgaacacc  14040
agttgtttgt gttctgcaga agcccgaaca catgtctaga cggggcccag atgttgagcc  14100
tttggggtgg ggcttaaaga ttgtgctgga ggggaggcta ccctgttatg tgttcccaga  14160
ggcctgccat ttctgggaag ggacagttat gtggagtgag ctgcttctag gagtttgagg  14220
ggttgtggga tcccctgaca gaggtggagc atctttcctt gtctgctgtc cccatgtgtc  14280
tattctgaat ggctcaagag caaccctccc tcacatgatg gctcacccat cccctcacc  14340
ccaggagaat cccagttggg ggctgagatc cttggctgag gaatgtagca gggagaagta  14400
ggaactgcct gtcgccctca catcctgtct gtcccctcat ggctgcctgg ggagggatgt  14460
atgggaggag gtggagagat cgcttcctcc cagggcagca ggaagggtcc ctgacttcct  14520
gtcctgggaa ggcgaccctg tccctgtgac ttgctctgtt ggccggtagg gaagttccat  14580
cttctaccca acttaactcc tgtggtgctg gcttgctttt gtgggatcct ggatggtgga  14640
ctcatctggc ctggggcaga ctgtgtgtgt gtgtggcgag gtgtggaacc tgaagtggag  14700
agccctgtag catcctgctc ggcctgcagt catttgctcc tgggattgca tctatggtcc  14760
tgatgcaaca tcgcacagag atgccagcag ggctgtgtcc ctggtccctt cccagcacta  14820
gcatagctga ggggtcccag catagccctc ccaccaggtg aggactggag accctgactg  14880
tgctttggaa gctttactct aggggaaata tgggagagtg gcatggagag gaggcaggtt  14940
gtagggtgtg atccccagtt ttggaggatg agttggagac taatgagagg tgggaagagg  15000
ggtcaggctg cagaaaatct gtttctgcaa gatcaagaag acaagtcatt aactccatag  15060
ctggaagggt ctagttcgag ggtctgtggg gtcagagggc atgtggcagg ggggccaccc  15120
taggcagaag agggtctgcc atcttgccag gtcctattct acccaggcca ggccctggct  15180
ctggatatgt cagcctgggc acaggacccc tggaaaggag ggtctgcaga gagagccccc  15240
agtgagactt catctgctgt ctgctggcta ccccggatag ggaccagtct aggcccccag  15300
ctccagctgg gccagtgtgg gcatggtggt ggaggggagg cccccaggga gggagggacc  15360
cagaatgaga agcttggggt ccactgtaag gctctgggga gccctggaag ttttgagcca  15420
gtgacacgga tcccttcttt ggaaggaaag cagtgccata aggggcaggg ggccagggag  15480
agggtagatt agatggggtg cctccctcta aggatcccca aagcctgaag gacaaggctc  15540
```

```
ccaggagttg gtgccaggct tgaggaagac acagccctct tcccacctcc cacagcaggg  15600
agcaggcagg agaagggcct gcctcccatt ctgtaagcga tacctcccat tctgtaagag  15660
ataaagacct ctgaccccac cccaggctct ccagggagcc aagcctcacc ttagcatggg  15720
gggtagggtt agggatgggc cgagcttgag ctacaatgac ctctcatctg accctgaccc  15780
ttttctcttc cttggggccc catagctgcc cccgtccctc agggccccga gtgaaggctg  15840
tgaagctact gattgtggag gtcaccccaa gacctgtgtc tctatcacaa atgtcccctg  15900
cccctaaaag gcccacagga gccaaggtca ggggacacat cctggaggcc caccccccta  15960
gatgccccca cctcatcccc acctggaccc tgcttcctgc aggggtacct gttgctggga  16020
ggcatacctg gtccccagct ccactgggct cgccttcctc agtttctccc ttagggcctg  16080
cagggtcttc ctggctctgg gccccttccc caacctccag tccccaggaa gctcctcccc  16140
aatcctctgc ctggggagcc acattccgag cataactgag acaggtatgt gtccctccct  16200
ctgcaccact tgtgggtgaa ggagactgcg ggtttgctcc aggaaggaag gagaccctca  16260
cgccctgctt tgtcagggaa gtggcctggc ctcttccagt gccagctgcc cacgcatcat  16320
gagctgccca ggctggcagc tgagcgggca tctcctccag cctttggcca ctataccctg  16380
gtctggactt gtacacttgt acactcccac caccctcctc tcccccacct aataaagact  16440
ggtccttggg ccccccctgaa ttccctagga gggatgcagg cttggggtcc ttccccaggc  16500
ctttccctcc cgaactccga gccaagagca gagaaaggaa gtgttgtctg ccctctccgg  16560
gcctggcaca ggaacagggt cggagagtct ggcattagtc cagcccagcc ctgcccagtc  16620
ctgaagccgg gggtcctggt ggccacagcc tagactggcc tgcctgattc cagtgagcac  16680
cctcccttcc tccctgccac gctagccttt gggccttcac gccagtcttg ggcctttggg  16740
gaaggtagtc ctaggctata tctcaggcta gagagatgct gggtcccggg ccgccggcct  16800
tggccttggt gcaggccctg tggcctggga gccggatgtg gacacagaca cccccagaca  16860
gggactggct ccgcagagca aagcggggca ggtaggagcc cagggcaggt tccagggctg  16920
gcttcctcag ggctagagct ggctccctct gctgtctggc atttagcttc tgtacccccca  16980
agtcctgagc ccgccctact cccccacatt cctccctgcc gaggggggag gtggcttctt  17040
cctgtccctg tttccctctt ccagacgtaa gttctcaccc cacccccctcc agacccgccc  17100
cagtgccgtc ctcagcccct cccccaggca ggtccttgga gctggggcag gcccaggctg  17160
gaggctgcgc gcctgggctt tctccttcct tccagccact gggggcgggg catctgctca  17220
ggtggagcgt ggcctgctcc tgcactgtcc tctctcacct agggtccccg gtaggaagtc  17280
tccgagagca tgggcttgtg ggaccacagc gggctggctg ataccctcac tggggcggcc  17340
ccaggagctt ggggcgtggt ggggggtggg gagggggttg ctgctgaaat caaagggcat  17400
tggatccatc acttcaaggc agtgcgctcc tttcccgcag gcctgagctg gtggaaacag  17460
ctcctgactt tttccagacc ccaccccatc accctgctcc ccacccagag aagagccccc  17520
gcctccatac tccccagcag attggaaatg gaaaaaaaaa aaagttgttt tgaaactgtc  17580
ctctccccctg ctgtctgtac ctgccttccg cagggctctg gacagagtag attccagtgg  17640
ggcctgcctg tggaaggaag gcagagccat ggaggtgctc gcagcctctc tggggtgctg  17700
ggaagaactg gatcgcctgg tcagggctag ctggtctgga tctggggctc tagccccctg  17760
ccccaccaat cctttcagac tgaggtaggg agagtgcaga gggtgggatg gggctgcccc  17820
aggtaaggtt agcaggggcg tgagcccaga cttcagggtt gtagatctag ccaactgttg  17880
cttgccctgc acagcctcct ccagcctgtt ttgcttcctt cttaaagggt taatccccca  17940
```

-continued atcccctgag aatcaaagcc tgcccccacc ccatcaccac agtggggtgg aagacagctg 18000
ctgaaattga cctctctcct gcccctgccc cccaagtcct ttgccttcac cagaaggccc 18060
aggccagctg ccctccctcc cagcccagag gcctgaactg ctctgctggc cccagcaacc 18120
ccctcagcat tgggataggg gaactgtggc tccccacaca ggcccctgag gcccagccca 18180
gcaagctggg ggctgcaggc acaatccctg aagtagcccc aatagcactt aacactccag 18240
agtcccagga agcgcccacc tctcacaaag agaaaaaggg atctcagaaa tgagagttag 18300
tgacagctac cctgatgaga ttgacccagc tcatcagaga gtactgtgtc cccataggct 18360
acagggggct caggagggat ctgggcccta ttctaggctg tggctgggaa ccggggaggg 18420
gtgacctggc ctctggtgga gcttccaatg gggagggaag ctcccctcaa aggggcctct 18480
ccctccagag cagatcctga gaacttcctc tgaggaaggc cccctgctag ggctgcttta 18540
cagctggacc tgggaagggg aagatggtcc ctcccacctc ccctcccact gaggcatggg 18600
aggggcaagc tctctttcct cacaggcagc cggctgtttc cagctgtgtg gcctgcacat 18660
gtgtgtgtgt gtacatttgt atgcacgtgt gcctgcaacc tcaggtgtac caaccaccac 18720
acaacagttc tggttgaaac tccagctggt ggcctgtggt tcctgccacc cttgtatcgc 18780
aggactcagc ctggggaggg gaccctgcag atgctctgcc aatgggatgg tagccggcaa 18840
ccttggcttg tgtcccagag ttctgggaac agggctgtgg gccctctgtg ggtgccgtct 18900
cctgcctgct gccccagtgt ccagctgtgc tcccctccca ccaccccatc cccggcagag 18960
agctgggccc ctgctcctgt gggctctgcc gctgggtttc tcaatgccag agatggaagg 19020
gctgcattga acaggaagag tccctgggat cacttgggtt ccctgtcccc tcacgcctgc 19080
tggaccctgt gtctggctaa gttagggagc agggcaggtc aggagaggtg ggtctgcctt 19140
tgatgtgagg tgggcctgaa gctccctacc tctcctctta gcaacttcct ctgcactgcc 19200
ccctctgcat accaggccca gaagcaggca acctgttgtg gctccctgag gcacctgtcc 19260
ctctggcaac aggtacatga tttctatgta cattggggag aaataaaggc acaacatctg 19320
ggccagatta tggcctgtcc tgacccacaa gtggggaaag gatgtatgtc cacccctgtt 19380
cctagagggg gggaagtgaa gcttgctaga gtccactcgt gaatccagcc atcagttcct 19440
tcctcaccca cccgtccacg caggacctag cagcaggccc tcacaggacc actagaaggg 19500
ctgctgcagc tacccacgcg gctctctcct gtctggtcgg tctttctgtc cctttgttcc 19560
cagcttctct tggttccaat gttgtagcca tgcgttctgg gaaacacact cactcagaag 19620
cacaatgcaa ataacggagt gcagtttatt acaccggcgg gcccaaggca gagtctcctc 19680
ttagccaagg accccgacca gtttttctga aaaccttata taccctaagt gtacgtgccc 19740
aaacccacct ccccaaattc cctgaaacta gtctgaacag aggaaaagaa agatacagtc 19800
aaagttaacc tgtgattcat atgccttaag cctaggtagt taacagtgga ccattattaa 19860
taggcctgtg atcatacccc aataagcata atagaattta tgattctatg cggttacaca 19920
gataattagg gtattcttta ggtaacagag agtctaggaa cgagccctgg ggctcttcca 19980
tccggagggg tctggttttc cagttggtgt gtcgtttcca tagatactgg gcatatagct 20040
caaagtccac agtccggccc aagatggagt cctgctttca agatggagcc tggtctgtct 20100
gtttcctcct tcatccctcc tcttcatgct cttaactcat agtatgagca tcattcatag 20160
ggatttattg caccctgact ctccgacctc caatttggga gaacgacatc aacctttggg 20220
ttacagagtt cataatacat tgtaaaataa agggtccaca aagcagaact atgaaggcaa 20280
ctataacaat ggtaaatata gttttccacc aatcaccctt cacccaacat aggaccgaag 20340
tccaaaaagg aagatgtatc agacataact tttacctgac ctttcatgtc atctagggta 20400
gctgatctat agccagataa atcaggaata tacacacaac attcaacttt aattatagca 20460
caggtccctc tttgtactga aactgtggtc aatctcaaga tgatagcagc aagtccttgt 20520
agcagcagtt gattgtagag cttcatctct gtttcttctt taagatgatc ttggtttcat 20580
ggggatcaga ggggtccctc tgcacagtcc actcggcgtc ctccgggtct gcatggtatg 20640
ctctcttcag cctcatgtgg aggatccagg gagtgacacc tgcaacttta actgcagtag 20700
ggctggttag aacaacagca tatggaccct tccaatgtgg ggccaaggag tcgtgtttcc 20760
agtccttgac cacacccgat ccctgggcac aaattcgtga atctgttccc caagggggaa 20820
cggcaccttt tcttgtacaa acttagttac ctgatttatt accttaccca gttgttccat 20880
ctgctgtgaa atctcatctc cccttacctg aggcaaattt gttgacacct gttttattat 20940
gggagggggc ctcccataca caattttgta cagagacgat tcatgggact gtggggtcat 21000
cctgagtctg agcagacccg tcagaaacaa gtccacccag gaaccgtcag tctccaagat 21060
ccacttggag agtgtctcta agtgtccggc tggttccttc caccatccca gaactctggg 21120
gcctatatgc tgtatgtaat ttccacttga tgtttaaagt tttgcttact tggttatact 21180
aaaacagcta caaaagccgg gccattgtcc gatccaatgc tggtaggaaa tccaaatctg 21240
ggaactatct ccctaagcag gcaccgggct acttttgatg ctctttcagt gagggtagga 21300
aaagcttcta cccatcctga gaacgtacat actgtgacca gcaggtaatg gtagtgtccg 21360
tgaggtttca tttcagggaa gtccacttcc aggtgttcaa agggcagcgt gccttttacc 21420
tgaatccctg caggtttctg tctgtgccaa caggcagcat tggcctgtaa gcaggcagtg 21480
cagttctgag attttgtcct gcatggggaa gagaggaggg gaacaaagaa atagtttcaa 21540
attatctctt ccagtttatc atggcataga tgggtcgctt ggtgtgtttg gcttaccaga 21600
gtgggtgcca gctcctccgg tacccataat ttgccacttg gcaattccca ctatcccttt 21660
tcagtcttga tggccccttc tgctttggct agttggtttt gagcttcagt gtattttgga 21720
gagtctagtg ttagctcagg tagctccgcc aatatgaaag ctttaacagg ggcttcactt 21780
gtcaccccca agcccttggc tgcttgttta gcggtcttat ctgccagtct gttccctgag 21840
cccggggagt atcctctttt tgacgttctc agcagtgtat gactgcaatc ctttctggtt 21900
cccaggcagc atctaatagg gtcttaattt cttccttatt ttttatcttt ttcactagct 21960
gtcaaaggcc tctctcctta tacagagccc tgtagtgtgg caaaagcata cctggagtct 22020
gtgtcaaggt ttgtcttctt accttttgac agctggaggg cctggattag agcatatagt 22080
tcagcctgtt gaatggagca gtgtggtggc agagagggag cctcaacaat ggtttcttct 22140
gtgaccactg catatcctga cagtcattgt ccttgtttca ccaggctggt gctattggtg 22200
tacacgaccg aatctgggtc cgggattggc tggtctctca agtcaggtct gctggcatat 22260
ttccttgcga tcatgtgagg gcccaccttc tcccacagga aggagagtgg ccagattcag 22320
ggcctgacaa ggctcagtag taacatgggg gttctcacat aacagtccct ggtactgagt 22380
aatctgggat gttgacagcc atttatggag gtccccttgc aggagagtgt tgacctcatg 22440
tgggactttt acaaacaaat cttggcccaa agtcagcttg gttgcatcct ggaccagtaa 22500
ggcaactgcc tgtaagcatc ccagccaccc agtagcaaca ctgtccagct gattagaggt 22560
aagtcacagg tctgtcccat gtccccatag tctgggacaa cactcctata gccaccttgt 22620
ccttttcagt catgtaaaga gtaaatggct tagcaaggtc tggcaggccc aaggcgggtg 22680
ctgatgtaac tgtactgggt ttgagtttta ttaccactgg gacttgtttt gcaagcctgg 22740
gggggttgtc ttctgcccag acctcaggga attgttgagt taactctctc tcttgaccat 22800
tgagcctgtc cggtttccct tctgggagat cgtgcaatct cccttcatct tgaggggtta 22860
ctgagaggaa gagtaaatag gtggttaagc ccactcgaac agtgggtctt tcttggggag 22920
acagtgactt gttcccccaa tttagacagc aagtctcttc ctaacaaagg tactgggcat 22980
tcagggatgt ataaaaactc atgagtcact tggtgtcccc ccatctgaca ttttcagggt 23040
aggctagaga cacaaggctg catttatcac catctgagac ccagcagcct ctggctgggt 23100
ctattggcgt ataaagtcta taggcctcgc atagtctttc gcagaactca gggtgattcg 23160
ctttcccttt gaatcacttc agagggtttt gtgatactta tagcttttcg ggcccccctc 23220
ttgagacctt gtaaaatagc cacccgataa ctctccaggt ggcccctccc ttcctctgtg 23280
ttacagtccc agttgggcct ctcatccggg gtggctagtt ctgcccaccg ctgcgggttt 23340
gcggtaccct caggtgccat ttc 23363

<210> SEQ ID NO 6
<211> LENGTH: 6491
<212> TYPE: DNA
<213> ORGANISM: Bos taurus
<220> FEATURE:
<221> NAME/KEY: misc_feature
<222> LOCATION: (1822)..(1871)
<223> OTHER INFORMATION: n is a, c, g, or t

<400> SEQUENCE: 6
aggaccatgg agcctcccca cacctggagc tgctgagccc tatcccacgt gctagacaga 60
gtaaggggtg ctgggggatc ctagcgaagg gaagtcctcc tcttcaccag cctctggccc 120
acttgtgggt aaagacggga aggcaggaat tggcccccac gtccccacac agacatgcag 180
actttttgtt tgaagcagga gcccaggagg tgagcccaaa gtcaccaggt gggtgtcagg 240
gtcaggcagg acaccaagaa gagacctctg aagcagcatc agccagttgc ctcttggtca 300
ccatggacac caggctgcaa agaaggttga tgtgcccact ggggacaggt cagtgtggcc 360
ctgggggcag gttgcagggt ttgtgctggg aatggcaggg ctgatgggaa caggcctctc 420
tgggcagggc agtcagctct gtggttccca gcacggagca ttgcccatgc ctgtttttgt 480
ttgaaatctg gggccccaga acccccaaca ccatgttctg atacagtgtg ccccctcagt 540
tactgaaaca gaaatggccc taagccctgc ccacaagcca cagggatggg gcctgggctg 600
tggctggtca gcccaggatg ggaatggaag gggacagggg gctggcctgt ccctgcaccc 660
gcagctggca ctcacagggg aactgcttcc caatggacat gagtccagtc tgctctgctc 720
atcaccacca ctgcaagggc tgtttctggg ccttgctcca cccatcctct tccacaaccc 780
catcatcaag tgggcacgtg atgctggagg ccctgggtga ccatgggcac attagttgta 840
tattgctatt gttacttaca ataactttaa ttttacataa aacattgtta attatagctg 900
tacaacaaat taacctacaa tttatccgtt taaaacaaca aacacattat ctcacacaat 960
ttctgaggga taggagtcct ggaactgctc agctgggtgg tcccggctct cagtctcttc 1020
ggattgctac tgagatgtcg gcagcagctg gggtcccagc tgaaggctgg agaccagctt 1080
ataaacccca cactctgttg gccgctccat agcaaaggac agctggcctc ctccaagtgg 1140
aggatgttag agacagagag agacaggcca ggatgcccct gcgacctcat cttctacagg 1200
accttactgc tgatgcaggt caacctcagt acattcagag gtagagtacc aggtcggggc 1260
tcttgggggg gctgcctcct gggaggctgt caaccccagg gcctgtttcc ttgcccagtg 1320
gtgcctccca ggataggtat ggcccctaga gcttcaaggg gcagagagca gccagacacg 1380

-continued

```
gctccagaac cctctgggct cagcttcttt cttgggggaa aggggagcag gtcctggagc   1440
ctagaggagg ctgttggggc ctggagataa tcaggtgatc acaggagctc tggttgggaa   1500
gctaagggct cacctttcaa aagtcaaggc tcccaggagc cccaggtcct accccatttc   1560
aaactcccaa gtacctggag ttttctgggc ctggcgaggc cgactgctgt caccgttagg   1620
accaactctt tctccagatt tcaaacacct atgatttgct gtcattgtta gtccccaagc   1680
cctgacctca caggcaagaa agagggaccc agagtcacag ggttccacag ggcgagacac   1740
ccacagaggc aggcagagca cctgactaca cacaggaatt cagcaaacac tcattgaccc   1800
ttggtcccca ccaggaactg gnnnnnnnnn nnnnnnnnnn nnnnnnnnnn nnnnnnnnnn   1860
nnnnnnnnnn nggattgcgg tgcagaggaa ttccccagag cccctctgag gcaggggagg   1920
gacaggcaat gggtggaaga gtggggaggg tgggaggaag aagagtccac cccagctctc   1980
cacagaccag gcaggggtcc aggctgagtg tggaaagggc catggctcca cccccagcag   2040
acgccaggat actgccctca gctgcccagg ggcagcctgg ggaggggccc agcctcagct   2100
gtgcttcctc agactcccct aatctaatca agggtgacac tcctttcacc caagctaatt   2160
aatgaggcct gtatggcctg agcgtctttc tgttccaagc aggtactggg gataggagtg   2220
agtgacacag acagggccct ggcttccaga gcccttggag cctggggtgg ctatctcagg   2280
tgggaaagtg gggagagaac ctcgggggc agggagggg ctgagtaggg aagggccaaa   2340
gggggcaggg aagggacaga gacacgagga acttgcctgt ctgaggaaca gtgtggttcc   2400
ctcagagccg gagaggtccc tggagggctg acaggggcct cagcacaaac acctctttgg   2460
cgacagcgtc ttgaggacag atgaccagga acaggaagta aggaagtaaa gggaagcaca   2520
gcccaggaac agggggatct ggtttgacac tgtgattgcc ccctccctga ggagtgatga   2580
cccgagctcc atgtgacctt cctgggcagc cctcctccct ctggccacca ggtggggaga   2640
tccctcttat tctttcaggc cacgtggaac ccagctctga ggaggccttg tccacccctc   2700
tacccaccca accacctggc ttcatatccc aaagtccctt gccttcccct cctgcactga   2760
gcctccaccc caaacagctc ccctttccca aaaaagctga acttctggct cctgaaatgg   2820
accctctgca actcttctgc tgggagggct cccaggctgg tcagcagtaa tgcccccaca   2880
gtcctgctgg tgacccagct ctctgagcct ccccagggcc tggaccagtg agtgtgtgca   2940
ggtcccaggg tgtggctccc ggcccacatg gctgccactg ccccaaacca ctggcccaga   3000
ccctggacac ccagggagat gggccaggca gccagagagc aggaggggac tggcttggtg   3060
ggacttggag ggccctgctt ggtgtgcacg gctgagtcct ggagggcaga tgaaccttgg   3120
tcaggaactg ttggggtcat tggaggagga gataagcctc tagcagtgac taaccctcct   3180
cctccctgat gctccctggc caggcaggta gctggcaacc atctgatgaa attggctgtg   3240
ggtgggaaac ccatcttgcc ttgacctcag agggctcagg atgagacact gcagtgtcag   3300
ccacatgact caaccacctc ctcactgccc ctggagcaca gcgtccagca gcagcctgag   3360
gagacctagg accacaggac agtggctccc cggccaatgc cccacgctgg ctaggatcac   3420
tgtattgtgg ggtcagcata aagccagtgt tcaagacagg agcataggcc tgccaatgaa   3480
cccccaattc cttcctactg tcgggggact ccctctcagg ggaggactgg gctctggcgg   3540
gaggtgagcc ccagtacaaa gtgccctttg tcaggccggt tgggggccct gcctctagga   3600
ctcagatgcc ctcttctgct ggcccccatc tgctgggcag agactggctt ggggcaggct   3660
tgacccacag gtgccaagag tagttctgtg ctcccccggg agaaggcagg cggtgcacca   3720
ggccagaacc caagcttcag cccacctcag ccccagagac aacagcgtgc acacgtctct   3780
```

gccttccagg ggcctcagga ggggttgcgg ggagagaact gtgccccagg aggatgcacg 3840
acctcttctc agcactggga gacgctctgg gaaagtggta actgttccag tcctgcctga 3900
gccccccagg gacatctcac acacaccctc ctccctcgag gcggtcggct tcagcgcaga 3960
gggacacagc caaactcaag gccgggcgaa cccctgcgcg gcgcaccggc cggcccaggt 4020
gggagctgaa taaatcccca cggcccggcc cggcccggcc cgccccgccc gttcatgaga 4080
agacatcaac cgaccccggc gctgggcctc ggccaaactg gacccttcac gaagacgaca 4140
aaacaaaatt ccctacccga tctctggaaa taaccatttt ctggcacagt ctcagtcggt 4200
tgtagggccg cggtctcacc gcagccacgg cctccagggc gcgccctggc cctgagcccc 4260
ggccccgggg gcggcgaggg ccagcccggg caggaagatg ggtgccaagg ccgccccggg 4320
gcgcggcaag gggcaagggc cgtcaaaggc tggcggcggc gggcggcctg cgtagatctc 4380
gggctcctgg gcttcagtgg ctggggccag tggaagcggg cggcgcgcgg gccccagccg 4440
ggccaggcag gctgccagat ggcagagcag acgagaccgc acgtccgcag ggacgccctc 4500
gcagccagcc aggaagcgat tcacttcggc cagacactca tggaagccgg cgcgatactt 4560
gcccaggata gcggggtccg agcggagggc agctgcgggg gtggcaggga caggcggtcg 4620
gcgcccgcgg cctcagcccc ggcccctgag ccctcgccgc cgccctcgcc tcacctgtca 4680
cctgcacgcg ccgcaggctc tgcaggtgcc tcacggtcag ctccaggatg tccgccttct 4740
ccagcttcga gcggcgggag ctctgcgggc ggggccggtg agggcggcgg gccgcccagg 4800
aaggccggga ttccagactc cccagtcttg tccctacccc caactcacct ctttcctgag 4860
ggcgtccagg aggaggctct gcagctgagc cagactctcg ttgatgcgcg ctcggcgccg 4920
cttctccatg accggcttgg aggactgtgg agccggcagc cactgagtcc tgcaggcatc 4980
atctcccctc tccccttcgc gccccccccc cccccccgc cccgctcctg ccaacccacg 5040
cccggccagg tccccacctt ccggtgctcg gccacgctcc ggggctggtc tggggtccgg 5100
ctggcgccgg ccgccgctcc cgcccgcggc gaggccctcg gcttccccgg gatgtccgca 5160
ggcatggtgc gccccttcgc cacccccagc cgagggcagg ctgggcgcgc ggtttcccag 5220
gcacttctcc cgcgggtccc aggctcagct accaagcgcg tgtctgcagc agcccggcta 5280
tttaaggcag cgcggctgcg gggcgtggga atccctctcc gcgttctttc ccacactcga 5340
gccagccaat gagccgccgg cgccgggcag cccgcccccg gccgctgccc ccgccggctg 5400
tcagtcacga gtcagctccc ggcccacaga ccccgctggc aacaaaggct agccggggca 5460
ccccgcccgc gcctgcctcg gaccacgccg gccaggcggg aaaatcgccg cgccccggtc 5520
cccagttccg agcgatgcgc cgggaggggg cctctccggg agggcggagg cgcgaggctc 5580
accttcaggc cgagcggaga ccgcgagaag tctgaaagga aaattcgcga ggggccctta 5640
tgcgctcacg aagaaccggc gagcctccgc cttccgcgga tcccgcgggg gccttggacc 5700
tccgcgcagc ctgcgcatct gaccctcgcc gccagcagca cctgcacgat gccggggaca 5760
cagtgaacat ggaacaccag ccgctggaca ggagagaagc tgactggcca aggtcgtgag 5820
ggaagcaggg tggcatcaca gggccaaaga aagtaatgcc gcagagcaga tagtgacgtc 5880
atcacaggca ggatgttgtc atggtatgga atgtaaggat gttactggtc aggctggtga 5940
tgtctccaag caatcatagg tgatatctca gggttaaggt agatgatgac acaagccaga 6000
tgtaatgatg tatggtcact ggtgatgtca ctctcttctg gattacccaa aagtgatgag 6060
ccaagcagca gccaagaaag tagaactcac aaaaaatgaa ggataattgt tacatttctg 6120
tttgttattt caaagaagca cgtggaggaa agagggctaa gcttattttc gtgtttgatg 6180

-continued ttgttttcac tttgaattcc cttgtggggc acaatcatgt tttgagtttt ggggatgcca 6240
gcccatggtg gcctgggcag tcttgtctgc atcccacaaa cctctctgga ggctcactgt 6300
aggcctgact gttcttgggg ctggggaggc ctctcctgaa ctctgaactg atgtgggagg 6360
aaaaggcaaa tgagcaaaat aaataatgac atggtttcca gagacagaaa gaaatgtgta 6420
ggttttgggg ggagccgaaa gccttctttc cactgagtgg tctggatggt atttttgcag 6480
tgagctctgc t 6491

<210> SEQ ID NO 7
<211> LENGTH: 6507
<212> TYPE: DNA
<213> ORGANISM: Bos taurus
<220> FEATURE:
<221> NAME/KEY: misc_feature
<222> LOCATION: (1822)..(1871)
<223> OTHER INFORMATION: n is a, c, g, or t

<400> SEQUENCE: 7
aggaccatgg agcctcccca cacctggagc tgctgagccc tatcccacgt gctagacaga 60
gtaaggggtg ctgggggatc ctagcgaagg gaagtcctcc tcttcaccag cctctggccc 120
acttgtgggt aaagacggga aggcaggaat tggcccccac gtccccacac agacatgcag 180
actttttgtt tgaagcagga gcccaggagg tgagcccaaa gtcaccaggt gggtgtcagg 240
gtcaggcagg acaccaagaa gagacctctg aagcagcatc agccagttgc ctcttggtca 300
ccatggacac caggctgcaa agaaggttga tgtgcccact ggggacaggt cagtgtggcc 360
ctgggggcag gttgcagggt ttgtgctggg aatggcaggg ctgatgggaa caggcctctc 420
tgggcagggc agtcagctct gtggttccca gcacggagca ttgcccatgc ctgtttttgt 480
ttgaaatctg gggccccaga acccccaaca ccatgttctg atacagtgtg ccccctcagt 540
tactgaaaca gaaatggccc taagccctgc ccacaagcca cagggatggg gcctgggctg 600
tggctggtca gcccaggatg ggaatggaag gggacagggg gctggcctgt ccctgcaccc 660
gcagctggca ctcacagggg aactgcttcc caatggacat gagtccagtc tgctctgctc 720
atcaccacca ctgcaagggc tgtttctggg ccttgctcca cccatcctct tccacaaccc 780
catcatcaag tgggcacgtg atgctggagg ccctgggtga ccatgggcac attagttgta 840
tattgctatt gttacttaca ataactttaa ttttacataa aacattgtta attatagctg 900
tacaacaaat taacctacaa tttatccgtt taaaacaaca aacacattat ctcacacaat 960
ttctgaggga taggagtcct ggaactgctc agctgggtgg tcccggctct cagtctcttc 1020
ggattgctac tgagatgtcg gcagcagctg gggtcccagc tgaaggctgg agaccagctt 1080
ataaacccca cactctgttg gccgctccat agcaaaggac agctggcctc ctccaagtgg 1140
aggatgttag agacagagag agacaggcca ggatgcccct gcgacctcat cttctacagg 1200
accttactgc tgatgcaggt caacctcagt acattcagag gtagagtacc aggtcggggc 1260
tcttgggggg gctgcctcct gggaggctgt caaccccagg gcctgtttcc ttgcccagtg 1320
gtgcctccca ggataggtat ggcccctaga gcttcaaggg gcagagagca gccagacacg 1380
gctccagaac cctctgggct cagcttcttt cttgggggaa aggggagcag gtcctggagc 1440
ctagaggagg ctgttggggc ctggagataa tcaggtgatc acaggagctc tggttgggaa 1500
gctaagggct cacctttcaa aagtcaaggc tcccaggagc cccaggtcct accccatttc 1560
aaactcccaa gtacctggag ttttctgggc ctggcgaggc cgactgctgt caccgttagg 1620
accaactctt tctccagatt tcaaacacct atgatttgct gtcattgtta gtccccaagc 1680

-continued

```
cctgacctca caggcaagaa agagggaccc agagtcacag ggttccacag ggcgagacac   1740
ccacagaggc aggcagagca cctgactaca cacaggaatt cagcaaacac tcattgaccc   1800
ttggtcccca ccaggaactg gnnnnnnnnn nnnnnnnnnn nnnnnnnnnn nnnnnnnnnn   1860
nnnnnnnnnn nggattgcgg tgcagaggaa ttccccagag cccctctgag gcaggggagg   1920
gacaggcaat gggtggaaga gtggggaggg tgggaggaag aagagtccac cccagctctc   1980
cacagaccag gcaggggtcc aggctgagtg tggaaagggc catggctcca cccccagcag   2040
acgccaggat actgccctca gctgcccagg ggcagcctgg ggaggggccc agcctcagct   2100
gtgcttcctc agactcccct aatctaatca agggtgacac tcctttcacc caagctaatt   2160
aatgaggcct gtatggcctg agcgtctttc tgttccaagc aggtactggg gataggagtg   2220
agtgacacag acagggccct ggcttccaga gcccttggag cctggggtgg ctatctcagg   2280
tgggaaagtg gggagagaac ctcggggggc agggaggggg ctgagtaggg aagggccaaa   2340
gggggcaggg aagggacaga gacacgagga acttgcctgt ctgaggaaca gtgtggttcc   2400
ctcagagccg gagaggtccc tggagggctg acaggggcct cagcacaaac acctctttgg   2460
cgacagcgtc ttgaggacag atgaccagga acaggaagta aggaagtaaa gggaagcaca   2520
gcccaggaac agggggatct ggtttgacac tgtgattgcc ccctccctga ggagtgatga   2580
cccgagctcc atgtgacctt cctgggcagc cctcctccct ctggccacca ggtggggaga   2640
tccctcttat tctttcaggc cacgtggaac ccagctctga ggaggccttg tccacccctc   2700
tacccaccca accacctggc ttcatatccc aaagtccctt gccttcccct cctgcactga   2760
gcctccaccc caaacagctc ccctttccca aaaaagctga acttctggct cctgaaatgg   2820
accctctgca actcttctgc tgggagggct cccaggctgg tcagcagtaa tgcccccaca   2880
gtcctgctgg tgacccagct ctctgagcct ccccagggcc tggaccagtg agtgtgtgca   2940
ggtcccaggg tgtggctccc ggcccacatg gctgccactg ccccaaacca ctggcccaga   3000
ccctggacac ccagggagat gggccaggca gccagagagc aggaggggac tggcttggtg   3060
ggacttggag ggccctgctt ggtgtgcacg gctgagtcct ggagggcaga tgaaccttgg   3120
tcaggaactg ttggggtcat tggaggagga gataagcctc tagcagtgac taaccctcct   3180
cctccctgat gctccctggc caggcaggta gctggcaacc atctgatgaa attggctgtg   3240
ggtgggaaac ccatcttgcc ttgacctcag agggctcagg atgagacact gcagtgtcag   3300
ccacatgact caaccacctc ctcactgccc ctggagcaca gcgtccagca gcagcctgag   3360
gagacctagg accacaggac agtggctccc cggccaatgc cccacgctgg ctaggatcac   3420
tgtattgtgg ggtcagcata aagccagtgt tcaagacagg agcataggcc tgccaatgaa   3480
cccccaattc cttcctactg tcgggggact ccctctcagg ggaggactgg gctctggcgg   3540
gaggtgagcc ccagtacaaa gtgccctttg tcaggccggt tgggggccct gcctctagga   3600
ctcagatgcc ctcttctgct ggcccccatc tgctgggcag agactggctt ggggcaggct   3660
tgacccacag gtgccaagag tagttctgtg ctcccccggg agaaggcagg cggtgcacca   3720
ggccagaacc caagcttcag cccacctcag ccccagagac aacagcgtgc acacgtctct   3780
gccttccagg ggcctcagga ggggttgcgg ggagagaact gtgccccagg aggatgcacg   3840
acctcttctc agcactggga gacgctctgg gaaagtggta actgttccag tcctgcctga   3900
gccccccagg gacatctcac acacaccctc ctccctcgag gcggtcggct tcagcgcaga   3960
gggacacagc caaactcaag gccgggcgaa cccctgcgcg gcgcaccggc cggcccaggt   4020
gggagctgaa taaatcccca cggcccggcc cggcccggcc cgccccgccc gttcatgaga   4080
```

-continued

```
agacatcaac cgaccccggc gctgggcctc ggccaaactg gacccttcac gaagacgaca   4140
aaacaaaatt ccctacccga tctctggaaa taaccatttt ctggcacagt ctcagtcggt   4200
tgtagggccg cggtctcacc gcagccacgg cctccagggc gcgccctggc cctgagcccc   4260
ggccccgggg gcggcgaggg ccagcccggg caggaagatg ggtgccaagg ccgccccggg   4320
gcgcggcaag gggcaagggc cgtcaaaggc tggcggcggc gggcggcctg cgtagatctc   4380
gggctcctgg gcttcagtgg ctggggccag tggaagcggg cggcgcgcgg gccccagccg   4440
ggccaggcag gctgccagat ggcagagcag acgagaccgc acgtccgcag ggacgccctc   4500
gcagccagcc aggaagcgat tcacttcggc cagacactca tggaagccgg cgcgatactt   4560
gcccaggata gcggggtccg agcggagggc agctgcgggg gtggcaggga caggcggtcg   4620
gcgcccgcgg cctcagcccc ggcccctgag ccctcgccgc cgccctcgcc tcacctgtca   4680
cctgcacgcg ccgcaggctc tgcaggtgcc tcacggtcag ctccaggatg tccgccttct   4740
ccagcttcga gcggcgggag ctctgcgggc ggggccggtg agggcggcgg gccgcccagg   4800
aaggccggga ttccagactc cccagtcttg tccctacccc caactcacct ctttcctgag   4860
ggcgtccagg aggaggctct gcagctgagc cagactctcg ttgatgcgcg ctcggcgccg   4920
cttctccatg accggcttgg aggactgtgg agccggcagc cactgagtcc tgcaggcatc   4980
atctcccctc tccccttcgc gccccccccc cccccccgc cccgctcctg ccaacccacg   5040
cccggccagg tccccacctt ccggtgctcg gccacgctcc ggggctggtc tggggtccgg   5100
ctggcgccgg ccgccgctcc cgcccgcggc gaggccctcg gcttccccgg gatgtccgca   5160
ggcatggtgc gccccttcgc cacccccagc cgagggcagg ctgggcgcgc ggtttcccag   5220
gcacttctcc cgcgggtccc aggctcagct accaagcgcg tgtctgcagc agcccggcta   5280
tttaaggcag cgcggctgcg gggcgtggga atccctctcc gcgttctttc ccacactcga   5340
gccagccaat gagccgccgg cgccgggcag cccgcccccg gccgctgccc ccgccggctg   5400
tcagtcacga gtcagctccc ggcccacaga ccccgctggc aacaaaggct agccggggca   5460
ccccgcccgc gcctgcctcg gaccacgccg gccaggcggg aaaatcgccg cgcccggtc   5520
cccagttccg agcgatgcgc cgggaggggg cctctccggg agggcggagg cgcgaggctc   5580
accttcaggc cgagcggaga ccgcgagaag tctgaaagga aaattcgcga ggggccctta   5640
tgcgctcacg aagaaccggc gagcctccgc cttccgcgga tcccgcgggg gccttggacc   5700
tccgcgcagc ctgcgcatct gaccctcgcc gccagcagca cctgcacgat gccggggaca   5760
cagtgaacat ggaacaccag ccgctggaca ggagagaagc tgactggcca aggtcgtgag   5820
ggaagcaggg tggcatcaca gggccaaaga aagtaatgcc gcagagcaga tagtgacgtc   5880
atcacaggca ggatgttgtc atggtatgga atgtaaggat gttactggtc aggctggtga   5940
tgtctccaag caatcatagg tgatatctca gggttaaggt agatgatgac acaagccaga   6000
tgtaatgatg tatggtcact ggtgatgtca ctctcttctg gattacccaa aagtgatgag   6060
ccaagcagca gccaagaaag tagaactcac aaaaaatgaa ggataattgt tacatttctg   6120
tttgttattt caaagaagca cgtggaggaa agagggctaa gcttattttc gtgtttgatg   6180
ttgttttcac tttgaattcc cttgtggggc acaatcatgt tttgagtttt ggggatgcca   6240
gcccatggtg gcctgggcag tcttgtctgc atcccacaaa cctctctgga ggctcactgt   6300
aggcctgact gttcttgggg ctggggaggc ctctcctgaa ctctgaactg atgtgggagg   6360
aaaaggcaaa tgagcaaaat aaataatgac atggtttcca gagacagaaa gaaatgtgta   6420
ggttttgggg ggagccgaaa gccttctttc cactgagtgg tctggatggt atttttgcag   6480
```

tgagctctgc tggagaaggc aatggca 6507

<210> SEQ ID NO 8
<211> LENGTH: 5165
<212> TYPE: DNA
<213> ORGANISM: Bos taurus

<400> SEQUENCE: 8
ccccactcca gtactcttgc ctggaaaatc ccatggacgg aggagcctgg tgggctacag 60
tccatggggt cgctaagagt cggacacgac tgagcgactt cactttcact tttcactttc 120
atgcattgga gaaggaaatg gcaacccact ccagtgttct tgcctgcaga atcccaggga 180
cgggggagcc tggtgggctg ccgtctctgg ggtcgcacag agttggacac gactgaagcg 240
acttagcagc agtagcagca gcagcaggtg ctatttttct taaccatttt ctggcctcag 300
ttaggatcct gtgtctttcc tcagtgctga aaagggagac tagtagttgg attatgtcat 360
cctatgtagg gcggtgggtt cgaaaaatag tctctaatag cctaatcacg gcttgtgctc 420
cccggagtat ggtggagtgt gtctctgcca gtttaatata ttcgtagagg aaaatggcta 480
gtaataatag gctacagggg ctgatggtag tgccccatgt gtcctgaact ggaggctgtt 540
gtagctttct aaggggcatc tgtagtgggg ttctttcccc ctgttccttg gtggagtgca 600
gcctctgtct aattgctgtg ttttgttccc ccttcccatc agtactcacc gggagaggtg 660
gatacaatct aggaggtcca gctgaggtgg aattctgggg acattgacca gaggtctcca 720
ttgctgggat tggagcctgc cgaaacggca gctctacgaa ctccgggaga gctggtggaa 780
gagcagtggc tgctgcagga acttcacctg gccctggatg ggcagtaag gtggcctccg 840 gtcctggtgg agcactggga ggcaggcgtg tcattatcca gtatggggga ggggtcaggt 900
catttccgtc caaatcctgt aaaatttcct tttttatcat cagtcaattt ttgtgccatt 960
aatattttcc cctttccctt ctggatacag aaccttgtcc aagtaggagg gtcttgagct 1020
aaccctagcc atgagtcaat atatggatat tgatccaggt gtccgggctc tcctgtgatt 1080
actgtataga cggcttccac tatttttaag ttcatggtgt tctctggtgg ccatcctact 1140
cccatagggg gccattcgac ctcacagagt atgtggaggc ggttaggctt catcttcacc 1200
ccgttcagtt cagttcagtt gctcagtcgt gtccaactct ttgcgacccc atgaattgca 1260
gcatgccagg cctccctgtc catcaccaac tcctggagtt cactcaaact cacctccatc 1320
aagttggtga tgccatccag ccatctcatc ctctgtcatc cccttctcct cctgccccca 1380
gtccctccca gcatcagagt cttttccagt gagtgaactc tttgcatgag gtggccagtc 1440
tcctccaaat cccttcttta aatttttaat catgcactcc aatacagttg ccttagattc 1500
acttcccctc atcttgctta ccttctcgga ccttctactt ttcctttcgt tctgtctacg 1560
aagttctcag taccctatgt acttctgata tttccactca atgacactta aattgccatt 1620
ctgccacctt cctaataggg gtgagaaaag ccttacctgc cagatcccag agggagaagg 1680
gggattggca tgtcttcacc tgccggtcag cacaaccaaa ccagaccacc acgtgatcca 1740
agattgtttc tcccttaact tttaaagtcc attctgcctc ggtgggcttg atcaggtgcg 1800
gatgaaaata cagatgggtt aaatatccca tgtcccaggc catctctgga aaagccaatt 1860
cgtactcact tatgtatccc cctcctatcc tgagaattcc gagggggtca agaatttcat 1920
agcagatggg acatctcctt ggggagggca gaatacgagc acacagaaac caagtttctt 1980
ctcctaaaaa tcccctggca attgcttggt aataattttc cccaagatgg catggacacc 2040
acctcctaaa tgaccttcac aagtttcctt cctaagccct aacacactca tcaacctgtg 2100

-continued

```
taccaagcaa tcgttgccac ctgcctattc caggctcctg tgggtctgtg ccccttctag   2160
tccctcccag ggcggtgatc aggccccctc ttccaccttg ctgggtgggt tcctcctcac   2220
ctgagcactc agttcccctg ctgccatcca ctacctgcta acatgaaagg tccgggcatt   2280
gagaagcaga atccttccag aagggcgagg tgccttcccc cctctagaag atttgagcca   2340
caaggcctca gagtagtccc aaatgggact tgtctcctca aagtgaggag tttcccggcc   2400
aacgcaccaa atgttgtagc cacacgttct gggaaacaaa ctcactcaga aggacaatgc   2460
agatagtgga gtgcagttta ttacaccagc gggcccaagg cagagtctcc tcttagccaa   2520
ggaccccgac cagtttttct gaaaacctta tataccctgg gtcgggaaga tcccctggag   2580
aaggaaatgg caacccactc cagtactctt gcctggagaa ttccatggag ggaggatcct   2640
ggtaggctac agtccatagg gtcgcaaaga gtcagacaca actgagcgac ttcactatat   2700
accctaagtg tatgtgccca aacccacctc ctcaaattcc ctgaaactag tctgaacaaa   2760
ggaaaagaaa gatacaatca aagttaaccc ttgattcata tgccttaagc ctaggtagtt   2820
aacagtggac aattatcaat agccctgtgg cataccccaa taagcataat agaatttatg   2880
attttatttg gttacacaga taattagggt attttaggta acagagagtc taggaacgag   2940
ccctgggact cttccatccg gggggtctgg ttttccagtt ggtgtgtcgt ttccatagat   3000
actgggcata tagctcagag tccacagtcc agcccaagat ggagtcctgc tttcaagatg   3060
gagcctggtc tgtctgtttc ctccttcacc aataggtgtc tgtctgccac tcctcttcat   3120
cttgacatcc agctggtcaa tacctccaag aagcaccgcc ccccaactca gacctttgtg   3180
ctggactgtg catctctctt ggcctggcca tggccctcag caggaataca gggtctcctg   3240
actcaccggc actgaccaca cctgggtgcc accctggctc ctccagcttt ctgtttcctc   3300
ctagacatgg gcaggacctg gccgaaagag atggatttgg ggctgtccta gaggggaggg   3360
acagaaggta tggatcagct agctccaccc catcccctac ctcaggggtc cccaaccctg   3420
aggccatgga ccgctactgg tcagtggcct gttaggattc agaccacaca gcaagaggtg   3480
aggggtcgga gtgctggtga acaagcgaaa tttcatctgt gtttacagct gctccccatt   3540
ttggcattac cagctgagct ttgcctcctg tgagatcagt ggcggcataa tgaacgtaat   3600
gcgtctgaat catccccaag cctctcccca cccaactcca aattcgtgga aaaactgtct   3660
tccacaaaac tggtctctgg taccaaaaag gttggggaca gctgccctac ctttgatttc   3720
cctggtggct cagacgtatc tgcctacaat gtggcagtcc tgggttcgat ccctgggtcg   3780
ggaagatccc ctggagaagg aaatggcaac ccattccagt acccttgcct ggagaatccc   3840
atggatggag gagcctggtg ggctctacct tttctccagg tgtctactac cccctcctct   3900
gttcggctgg cgccccctgg tggctgaagc ctgtcttggc aggcgtcccg gccctgggtt   3960
ccccaggcct gcgggtctgg ccttggccct tgtttccctg agacctcacc aggctggctt   4020
ctcctggtct cgtgcagtct cctgagcttg tttttactgg gcctctgtag ttggctctgc   4080
ctggatgtgc aaatccctcg accccatcct tcgggtctct gtacagtcat ccccccacgta   4140
gatgctgcga tctagggcaa tctctgctac agggtaacct tccaggggca aagagctcac   4200
ccgactcggc acctgcctcc tgcactgagc ccaccccccgg aggagtttgg ccggggccgg   4260
gcaggatgaa tgctgagtaa tgaaggagga ggggtgccgg ggtcagcggc cgctgccctg   4320
cgacccagcc ccaattcttc cacaagctct cacttaatgc cacctcccga cagcgcgggc   4380
taaccagcag tgtgggccct gcccggggct cgtgggtggg catacagccc gcggactcaa   4440
gtgggcccct cccggcctta gcctcacctg agggggcgat cggggccggg ctgcacgccg   4500
```

```
cctccttccc agcggttggc cccagtccaa cagcgacgtc ccgctgtgaa acgcccattg   4560

tctgctgagg ccgaggggga ggggatggcc ctgagacccg actctaggag gctgggggag   4620

ggggccgccc tgccccatcc tcttcccctc ccccgccagg gcggccagac acctgtggct   4680

ggaggccgcc tggcactcga ctgttggata cactttacac actagcgggg taccctcgag   4740

ggcccaggag tggagactgg cggaggtccc cacagcaaag gtgtgtgcgc atgcgtagag   4800

tgtgtctgct gccgggaggg cggtgccacc ccactcccac cccatccttt tggagcgcgc   4860

cggcccctcc cctacagagc gaaagggatc agagggaggc cagtaggtgg gacttcatat   4920

tctctgtgga cttcgttccc ggtcttcctc gcagggcaag ggaagcgtct ggaggggccc   4980

aaccacacgc gtgtatgtgg gggtacaccc gatgtgtgct gtgtggatga ggggcaaatt   5040

ttgcattgca tgaaggtgtg cagtgtgtat gcacacaggt gtgtgtgtga ctgcacagtg   5100

cctgtgcaga cttgagtgag tggttgtacg tatgtccgca tatgggagac ctggaacatg   5160

gagtg                                                               5165


<210> SEQ ID NO 9
<211> LENGTH: 5181
<212> TYPE: DNA
<213> ORGANISM: Bos taurus

<400> SEQUENCE: 9

ggagaaggca atggcacccc actccagtac tcttgcctgg aaaatcccat ggacggagga     60

gcctggtggg ctacagtcca tggggtcgct aagagtcgga cacgactgag cgacttcact    120

ttcacttttc actttcatgc attggagaag gaaatggcaa cccactccag tgttcttgcc    180

tgcagaatcc cagggacggg ggagcctggt gggctgccgt ctctggggtc gcacagagtt    240

ggacacgact gaagcgactt agcagcagta gcagcagcag caggtgctat ttttcttaac    300

cattttctgg cctcagttag gatcctgtgt ctttcctcag tgctgaaaag ggagactagt    360

agttggatta tgtcatccta tgtagggcgg tgggttcgaa aaatagtctc taatagccta    420

atcacggctt gtgctccccg gagtatggtg gagtgtgtct ctgccagttt aatatattcg    480

tagaggaaaa tggctagtaa taataggcta caggggctga tggtagtgcc ccatgtgtcc    540

tgaactggag gctgttgtag ctttctaagg ggcatctgta gtggggttct ttccccctgt    600

tccttggtgg agtgcagcct ctgtctaatt gctgtgtttt gttccccctt cccatcagta    660

ctcaccggga gaggtggata caatctagga ggtccagctg aggtggaatt ctggggacat    720

tgaccagagg tctccattgc tgggattgga gcctgccgaa acggcagctc tacgaactcc    780

gggagagctg gtggaagagc agtggctgct gcaggaactt cacctggccc tggatggggc    840

agtaaggtgg cctccggtcc tggtggagca ctgggaggca ggcgtgtcat tatccagtat    900

gggggagggg tcaggtcatt tccgtccaaa tcctgtaaaa tttccttttt tatcatcagt    960

caatttttgt gccattaata ttttcccctt tcccttctgg atacagaacc ttgtccaagt   1020

aggagggtct tgagctaacc ctagccatga gtcaatatat ggatattgat ccaggtgtcc   1080

gggctctcct gtgattactg tatagacggc ttccactatt tttaagttca tggtgttctc   1140

tggtggccat cctactccca tagggggcca ttcgacctca cagagtatgt ggaggcggtt   1200

aggcttcatc ttcaccccgt tcagttcagt tcagttgctc agtcgtgtcc aactctttgc   1260

gaccccatga attgcagcat gccaggcctc cctgtccatc accaactcct ggagttcact   1320

caaactcacc tccatcaagt tggtgatgcc atccagccat ctcatcctct gtcatcccct   1380

tctcctcctg cccccagtcc ctcccagcat cagagtcttt tccagtgagt gaactctttg   1440
```

-continued

```
catgaggtgg ccagtctcct ccaaatccct tctttaaatt tttaatcatg cactccaata   1500
cagttgcctt agattcactt cccctcatct tgcttacctt ctcggacctt ctacttttcc   1560
tttcgttctg tctacgaagt tctcagtacc ctatgtactt ctgatatttc cactcaatga   1620
cacttaaatt gccattctgc caccttccta ataggggtga gaaaagcctt acctgccaga   1680
tcccagaggg agaaggggga ttggcatgtc ttcacctgcc ggtcagcaca accaaaccag   1740
accaccacgt gatccaagat tgtttctccc ttaactttta aagtccattc tgcctcggtg   1800
ggcttgatca ggtgcggatg aaaatacaga tgggttaaat atcccatgtc ccaggccatc   1860
tctggaaaag ccaattcgta ctcacttatg tatccccctc ctatcctgag aattccgagg   1920
gggtcaagaa tttcatagca gatgggacat ctccttgggg agggcagaat acgagcacac   1980
agaaaccaag tttcttctcc taaaaatccc ctggcaattg cttggtaata attttcccca   2040
agatggcatg gacaccacct cctaaatgac cttcacaagt ttccttccta agccctaaca   2100
cactcatcaa cctgtgtacc aagcaatcgt tgccacctgc ctattccagg ctcctgtggg   2160
tctgtgcccc ttctagtccc tcccagggcg gtgatcaggc cccctcttcc accttgctgg   2220
gtgggttcct cctcacctga gcactcagtt cccctgctgc catccactac ctgctaacat   2280
gaaaggtccg ggcattgaga agcagaatcc ttccagaagg gcgaggtgcc ttccccccctc   2340
tagaagattt gagccacaag gcctcagagt agtcccaaat gggacttgtc tcctcaaagt   2400
gaggagtttc ccggccaacg caccaaatgt tgtagccaca cgttctggga aacaaactca   2460
ctcagaagga caatgcagat agtggagtgc agtttattac accagcgggc ccaaggcaga   2520
gtctcctctt agccaaggac cccgaccagt ttttctgaaa accttatata ccctgggtcg   2580
ggaagatccc ctggagaagg aaatggcaac ccactccagt actcttgcct ggagaattcc   2640
atggagggag gatcctggta ggctacagtc catagggtcg caaagagtca gacacaactg   2700
agcgacttca ctatataccc taagtgtatg tgcccaaacc cacctcctca aattccctga   2760
aactagtctg aacaaaggaa aagaaagata caatcaaagt taacccttga ttcatatgcc   2820
ttaagcctag gtagttaaca gtggacaatt atcaatagcc ctgtggcata ccccaataag   2880
cataatagaa tttatgattt tatttggtta cacagataat tagggtattt taggtaacag   2940
agagtctagg aacgagccct gggactcttc catccggggg gtctggtttt ccagttggtg   3000
tgtcgtttcc atagatactg ggcatatagc tcagagtcca cagtccagcc caagatggag   3060
tcctgctttc aagatggagc ctggtctgtc tgtttcctcc ttcaccaata ggtgtctgtc   3120
tgccactcct cttcatcttg acatccagct ggtcaatacc tccaagaagc accgcccccc   3180
aactcagacc tttgtgctgg actgtgcatc tctcttggcc tggccatggc cctcagcagg   3240
aatacagggt ctcctgactc accggcactg accacacctg ggtgccaccc tggctcctcc   3300
agctttctgt ttcctcctag acatgggcag gacctggccg aaagagatgg atttggggct   3360
gtcctagagg ggagggacag aaggtatgga tcagctagct ccacccccatc ccctacctca   3420
ggggtcccca accctgaggc catggaccgc tactggtcag tggcctgtta ggattcagac   3480
cacacagcaa gaggtgaggg gtcggagtgc tggtgaacaa gcgaaatttc atctgtgttt   3540
acagctgctc cccattttgg cattaccagc tgagctttgc ctcctgtgag atcagtggcg   3600
gcataatgaa cgtaatgcgt ctgaatcatc cccaagcctc tccccaccca actccaaatt   3660
cgtggaaaaa ctgtcttcca caaaactggt ctctggtacc aaaaaggttg gggacagctg   3720
ccctaccttt gatttccctg gtggctcaga cgtatctgcc tacaatgtgg cagtcctggg   3780
ttcgatccct gggtcgggaa gatcccctgg agaaggaaat ggcaacccat tccagtaccc   3840
```

```
ttgcctggag aatcccatgg atggaggagc ctggtgggct ctaccttttc tccaggtgtc   3900

tactaccccc tcctctgttc ggctggcgcc ccctggtggc tgaagcctgt cttggcaggc   3960

gtcccggccc tgggttcccc aggcctgcgg gtctggcctt ggcccttgtt tccctgagac   4020

ctcaccaggc tggcttctcc tggtctcgtg cagtctcctg agcttgtttt tactgggcct   4080

ctgtagttgg ctctgcctgg atgtgcaaat ccctcgaccc catccttcgg gtctctgtac   4140

agtcatcccc cacgtagatg ctgcgatcta gggcaatctc tgctacaggg taaccttcca   4200

ggggcaaaga gctcacccga ctcggcacct gcctcctgca ctgagcccac ccccggagga   4260

gtttggccgg ggccgggcag gatgaatgct gagtaatgaa ggaggagggg tgccggggtc   4320

agcggccgct gccctgcgac ccagccccaa ttcttccaca agctctcact taatgccacc   4380

tcccgacagc gcgggctaac cagcagtgtg ggccctgccc ggggctcgtg ggtgggcata   4440

cagcccgcgg actcaagtgg gcccctcccg gccttagcct cacctgaggg ggcgatcggg   4500

gccgggctgc acgccgcctc cttcccagcg gttggcccca gtccaacagc gacgtcccgc   4560

tgtgaaacgc ccattgtctg ctgaggccga gggggagggg atggccctga gacccgactc   4620

taggaggctg gggggagggg ccgccctgcc ccatcctctt cccctccccc gccagggcgg   4680

ccagacacct gtggctggag gccgcctggc actcgactgt tggatacact ttacacacta   4740

gcggggtacc ctcgagggcc caggagtgga gactggcgga ggtccccaca gcaaaggtgt   4800

gtgcgcatgc gtagagtgtg tctgctgccg ggagggcggt gccaccccac tcccacccca   4860

tccttttgga gcgcgccggc ccctccccta cagagcgaaa gggatcagag ggaggccagt   4920

aggtgggact tcatattctc tgtggacttc gttcccggtc ttcctcgcag ggcaagggaa   4980

gcgtctggag gggcccaacc acacgcgtgt atgtgggggt acacccgatg tgtgctgtgt   5040

ggatgagggg caaattttgc attgcatgaa ggtgtgcagt gtgtatgcac acaggtgtgt   5100

gtgtgactgc acagtgcctg tgcagacttg agtgagtggt tgtacgtatg tccgcatatg   5160

ggagacctgg aacatggagt g                                              5181
```

<210> SEQ ID NO 10
<211> LENGTH: 16
<212> TYPE: DNA
<213> ORGANISM: Bos taurus

<400> SEQUENCE: 10

```
ggagaaggca atggca                                                      16
```

<210> SEQ ID NO 11
<211> LENGTH: 22
<212> TYPE: DNA
<213> ORGANISM: Bos taurus

<400> SEQUENCE: 11

```
ggcctctcct gaactctgaa ct                                               22
```

<210> SEQ ID NO 12
<211> LENGTH: 22
<212> TYPE: DNA
<213> ORGANISM: Bos taurus

<400> SEQUENCE: 12

```
atcctgtgtc tttcctcagt gc                                               22
```

<210> SEQ ID NO 13
<211> LENGTH: 22

<212> TYPE: DNA
<213> ORGANISM: Bos taurus

<400> SEQUENCE: 13
gcactgagga aagacacagg at 22

<210> SEQ ID NO 14
<211> LENGTH: 22
<212> TYPE: DNA
<213> ORGANISM: Bos taurus

<400> SEQUENCE: 14
ctaagagagt catgcttggc tt 22

<210> SEQ ID NO 15
<211> LENGTH: 22
<212> TYPE: DNA
<213> ORGANISM: Bos taurus

<400> SEQUENCE: 15
aagccaagca tgactctctt ag 22

<210> SEQ ID NO 16
<211> LENGTH: 4620
<212> TYPE: DNA
<213> ORGANISM: Bos taurus

<400> SEQUENCE: 16
ggattgcggt gcagaggaat tccccagagc ccctctgagg caggggaggg acaggcaatg 60
ggtggaagag tggggagggt gggaggaaga agagtccacc ccagctctcc acagaccagg 120
caggggtcca ggctgagtgt ggaaagggcc atggctccac ccccagcaga cgccaggata 180
ctgccctcag ctgcccaggg gcagcctggg gaggggccca gcctcagctg tgcttcctca 240
gactccccta atctaatcaa gggtgacact cctttcaccc aagctaatta atgaggcctg 300
tatggcctga gcgtctttct gttccaagca ggtactgggg ataggagtga gtgacacaga 360
cagggccctg gcttccagag cccttggagc ctggggtggc tatctcaggt gggaaagtgg 420
ggagagaacc tcgggggca gggaggggc tgagtaggga agggccaaag ggggcaggga 480
agggacagag acacgaggaa cttgcctgtc tgaggaacag tgtggttccc tcagagccgg 540
agaggtccct ggagggctga caggggcctc agcacaaaca cctctttggc gacagcgtct 600
tgaggacaga tgaccaggaa caggaagtaa ggaagtaaag ggaagcacag cccaggaaca 660
gggggatctg gtttgacact gtgattgccc cctccctgag gagtgatgac ccgagctcca 720
tgtgaccttc ctgggcagcc ctcctccctc tggccaccag gtggggagat ccctcttatt 780
ctttcaggcc acgtggaacc cagctctgag gaggccttgt ccacccctct acccacccaa 840
ccacctggct tcatatccca aagtcccttg ccttcccctc ctgcactgag cctccacccc 900
aaacagctcc cctttcccaa aaaagctgaa cttctggctc ctgaaatgga ccctctgcaa 960
ctcttctgct gggagggctc ccaggctggt cagcagtaat gcccccacag tcctgctggt 1020
gacccagctc tctgagcctc cccagggcct ggaccagtga gtgtgtgcag gtcccagggt 1080
gtggctcccg gcccacatgg ctgccactgc cccaaaccac tggcccagac cctggacacc 1140
cagggagatg ggccaggcag ccagagagca ggaggggact ggcttggtgg gacttggagg 1200
gccctgcttg gtgtgcacgg ctgagtcctg gagggcagat gaaccttggt caggaactgt 1260
tggggtcatt ggaggaggag ataagcctct agcagtgact aaccctcctc ctccctgatg 1320
ctccctggcc aggcaggtag ctggcaacca tctgatgaaa ttggctgtgg gtgggaaacc 1380

-continued

```
catcttgcct tgacctcaga gggctcagga tgagacactg cagtgtcagc cacatgactc   1440
aaccacctcc tcactgcccc tggagcacag cgtccagcag cagcctgagg agacctagga   1500
ccacaggaca gtggctcccc ggccaatgcc ccacgctggc taggatcact gtattgtggg   1560
gtcagcataa agccagtgtt caagacagga gcataggcct gccaatgaac cccaattcc    1620
ttcctactgt cgggggactc cctctcaggg gaggactggg ctctggcggg aggtgagccc   1680
cagtacaaag tgccctttgt caggccggtt gggggccctg cctctaggac tcagatgccc   1740
tcttctgctg gcccccatct gctgggcaga gactggcttg gggcaggctt gacccacagg   1800
tgccaagagt agttctgtgc tcccccggga gaaggcaggc ggtgcaccag gccagaaccc   1860
aagcttcagc ccacctcagc cccagagaca acagcgtgca cacgtctctg ccttccaggg   1920
gcctcaggag gggttgcggg gagagaactg tgccccagga ggatgcacga cctcttctca   1980
gcactgggag acgctctggg aaagtggtaa ctgttccagt cctgcctgag ccccccaggg   2040
acatctcaca cacaccctcc tccctcgagg cggtcggctt cagcgcagag ggacacagcc   2100
aaactcaagg ccgggcgaac ccctgcgcgg cgcaccggcc ggcccaggtg ggagctgaat   2160
aaatccccac ggcccggccc ggcccggccc gccccgcccg ttcatgagaa gacatcaacc   2220
gaccccggcg ctgggcctcg gccaaactgg acccttcacg aagacgacaa aacaaaattc   2280
cctacccgat ctctggaaat aaccattttc tggcacagtc tcagtcggtt gtagggccgc   2340
ggtctcaccg cagccacggc ctccagggcg cgccctggcc ctgagccccg gccccggggg   2400
cggcgagggc cagcccgggc aggaagatgg gtgccaaggc cgccccgggg cgcggcaagg   2460
ggcaagggcc gtcaaaggct ggcggcggcg ggcggcctgc gtagatctcg ggctcctggg   2520
cttcagtggc tggggccagt ggaagcgggc ggcgcgcggg ccccagccgg gccaggcagg   2580
ctgccagatg gcagagcaga cgagaccgca cgtccgcagg gacgccctcg cagccagcca   2640
ggaagcgatt cacttcggcc agacactcat ggaagccggc gcgatacttg cccaggatag   2700
cggggtccga gcggagggca gctgcggggg tggcagggac aggcggtcgg cgcccgcggc   2760
ctcagccccg gcccctgagc cctcgccgcc gccctcgcct cacctgtcac ctgcacgcgc   2820
cgcaggctct gcaggtgcct cacggtcagc tccaggatgt ccgccttctc cagcttcgag   2880
cggcgggagc tctgcgggcg gggccggtga gggcggcggg ccgcccagga aggccgggat   2940
tccagactcc ccagtcttgt ccctaccccc aactcacctc tttcctgagg gcgtccagga   3000
ggaggctctg cagctgagcc agactctcgt tgatgcgcgc tcggcgccgc ttctccatga   3060
ccggcttgga ggactgtgga gccggcagcc actgagtcct gcaggcatca tctcccctct   3120
ccccttcgcg cccccccccc ccccccgcc ccgctcctgc caacccacgc ccggccaggt    3180
ccccaccttc cggtgctcgg ccacgctccg gggctggtct ggggtccggc tggcgccggc   3240
cgccgctccc gcccgcggcg aggccctcgg cttccccggg atgtccgcag gcatggtgcg   3300
ccccttcgcc acccccagcc gagggcaggc tgggcgcgcg gtttcccagg cacttctccc   3360
gcgggtccca ggctcagcta ccaagcgcgt gtctgcagca gcccggctat ttaaggcagc   3420
gcggctgcgg ggcgtgggaa tccctctccg cgttctttcc cacactcgag ccagccaatg   3480
agccgccggc gccgggcagc ccgcccccgg ccgctgcccc cgccggctgt cagtcacgag   3540
tcagctcccg gcccacagac cccgctggca acaaaggcta gccggggcac cccgcccgcg   3600
cctgcctcgg accacgccgg ccaggcggga aaatcgccgc gccccggtcc ccagttccga   3660
gcgatgcgcc gggagggggc ctctccggga gggcggaggc gcgaggctca ccttcaggcc   3720
gagcggagac cgcgagaagt ctgaaaggaa aattcgcgag ggcccttat gcgctcacga    3780
```

-continued agaaccggcg agcctccgcc ttccgcggat cccgcggggg ccttggacct ccgcgcagcc 3840
tgcgcatctg accctcgccg ccagcagcac ctgcacgatg ccggggacac agtgaacatg 3900
gaacaccagc cgctggacag gagagaagct gactggccaa ggtcgtgagg gaagcagggt 3960
ggcatcacag ggccaaagaa agtaatgccg cagagcagat agtgacgtca tcacaggcag 4020
gatgttgtca tggtatggaa tgtaaggatg ttactggtca ggctggtgat gtctccaagc 4080
aatcataggt gatatctcag ggttaaggta gatgatgaca caagccagat gtaatgatgt 4140
atggtcactg gtgatgtcac tctcttctgg attacccaaa agtgatgagc caagcagcag 4200
ccaagaaagt agaactcaca aaaaatgaag gataattgtt acatttctgt ttgttatttc 4260
aaagaagcac gtggaggaaa gagggctaag cttattttcg tgtttgatgt tgttttcact 4320
ttgaattccc ttgtggggca caatcatgtt ttgagttttg gggatgccag cccatggtgg 4380
cctgggcagt cttgtctgca tcccacaaac ctctctggag gctcactgta ggcctgactg 4440
ttcttggggc tggggaggcc tctcctgaac tctgaactga tgtgggagga aaaggcaaat 4500
gagcaaaata aataatgaca tggtttccag agacagaaag aaatgtgtag gttttggggg 4560
gagccgaaag ccttctttcc actgagtggt ctggatggta tttttgcagt gagctctgct 4620

<210> SEQ ID NO 17
<211> LENGTH: 4636
<212> TYPE: DNA
<213> ORGANISM: Bos taurus

<400> SEQUENCE: 17
ggattgcggt gcagaggaat tccccagagc ccctctgagg caggggaggg acaggcaatg 60
ggtggaagag tggggagggt gggaggaaga agagtccacc ccagctctcc acagaccagg 120
caggggtcca ggctgagtgt ggaaagggcc atggctccac ccccagcaga cgccaggata 180
ctgccctcag ctgcccaggg gcagcctggg gaggggccca gcctcagctg tgcttcctca 240
gactccccta atctaatcaa gggtgacact cctttcaccc aagctaatta atgaggcctg 300
tatggcctga gcgtctttct gttccaagca ggtactgggg ataggagtga gtgacacaga 360
cagggccctg gcttccagag cccttggagc ctggggtggc tatctcaggt gggaaagtgg 420
ggagagaacc tcgggggca gggagggggc tgagtaggga agggccaaag ggggcaggga 480
agggacagag acacgaggaa cttgcctgtc tgaggaacag tgtggttccc tcagagccgg 540
agaggtccct ggagggctga caggggcctc agcacaaaca cctctttggc gacagcgtct 600
tgaggacaga tgaccaggaa caggaagtaa ggaagtaaag ggaagcacag cccaggaaca 660
gggggatctg gtttgacact gtgattgccc cctccctgag gagtgatgac ccgagctcca 720
tgtgaccttc ctgggcagcc ctcctccctc tggccaccag gtggggagat ccctcttatt 780
ctttcaggcc acgtggaacc cagctctgag gaggccttgt ccacccctct acccacccaa 840
ccacctggct tcatatccca aagtcccttg ccttcccctc ctgcactgag cctccacccc 900
aaacagctcc cctttcccaa aaaagctgaa cttctggctc ctgaaatgga ccctctgcaa 960
ctcttctgct gggagggctc ccaggctggt cagcagtaat gcccccacag tcctgctggt 1020
gacccagctc tctgagcctc cccagggcct ggaccagtga gtgtgtgcag gtcccagggt 1080
gtggctcccg gcccacatgg ctgccactgc cccaaaccac tggcccagac cctggacacc 1140
cagggagatg ggccaggcag ccagagagca ggaggggact ggcttggtgg gacttggagg 1200
gccctgcttg gtgtgcacgg ctgagtcctg gagggcagat gaaccttggt caggaactgt 1260
tggggtcatt ggaggaggag ataagcctct agcagtgact aaccctcctc ctccctgatg 1320

-continued

```
ctccctggcc aggcaggtag ctggcaacca tctgatgaaa ttggctgtgg gtgggaaacc   1380
catcttgcct tgacctcaga gggctcagga tgagacactg cagtgtcagc cacatgactc   1440
aaccacctcc tcactgcccc tggagcacag cgtccagcag cagcctgagg agacctagga   1500
ccacaggaca gtggctcccc ggccaatgcc ccacgctggc taggatcact gtattgtggg   1560
gtcagcataa agccagtgtt caagacagga gcataggcct gccaatgaac ccccaattcc   1620
ttcctactgt cgggggactc cctctcaggg gaggactggg ctctggcggg aggtgagccc   1680
cagtacaaag tgccctttgt caggccggtt gggggccctg cctctaggac tcagatgccc   1740
tcttctgctg gcccccatct gctgggcaga gactggcttg gggcaggctt gacccacagg   1800
tgccaagagt agttctgtgc tcccccggga gaaggcaggc ggtgcaccag gccagaaccc   1860
aagcttcagc ccacctcagc cccagagaca acagcgtgca cacgtctctg ccttccaggg   1920
gcctcaggag gggttgcggg gagagaactg tgccccagga ggatgcacga cctcttctca   1980
gcactgggag acgctctggg aaagtggtaa ctgttccagt cctgcctgag ccccccaggg   2040
acatctcaca cacaccctcc tccctcgagg cggtcggctt cagcgcagag ggacacagcc   2100
aaactcaagg ccgggcgaac ccctgcgcgg cgcaccggcc ggcccaggtg ggagctgaat   2160
aaatccccac ggcccggccc ggcccggccc gccccgcccg ttcatgagaa gacatcaacc   2220
gaccccggcg ctgggcctcg gccaaactgg acccttcacg aagacgacaa aacaaaattc   2280
cctacccgat ctctggaaat aaccattttc tggcacagtc tcagtcggtt gtagggccgc   2340
ggtctcaccg cagccacggc ctccagggcg cgccctggcc ctgagccccg gccccggggg   2400
cggcgagggc cagcccgggc aggaagatgg gtgccaaggc cgccccgggg cgcggcaagg   2460
ggcaagggcc gtcaaaggct ggcggcggcg ggcggcctgc gtagatctcg ggctcctggg   2520
cttcagtggc tggggccagt ggaagcgggc ggcgcgcggg ccccagccgg gccaggcagg   2580
ctgccagatg gcagagcaga cgagaccgca cgtccgcagg gacgccctcg cagccagcca   2640
ggaagcgatt cacttcggcc agacactcat ggaagccggc gcgatacttg cccaggatag   2700
cggggtccga gcggagggca gctgcggggg tggcagggac aggcggtcgg cgcccgcggc   2760
ctcagccccg gcccctgagc cctcgccgcc gccctcgcct cacctgtcac ctgcacgcgc   2820
cgcaggctct gcaggtgcct cacggtcagc tccaggatgt ccgccttctc cagcttcgag   2880
cggcgggagc tctgcgggcg gggccggtga gggcggcggg ccgcccagga aggccgggat   2940
tccagactcc ccagtcttgt ccctaccccc aactcacctc tttcctgagg gcgtccagga   3000
ggaggctctg cagctgagcc agactctcgt tgatgcgcgc tcggcgccgc ttctccatga   3060
ccggcttgga ggactgtgga gccggcagcc actgagtcct gcaggcatca tctcccctct   3120
ccccttcgcg cccccccccc cccccccgcc ccgctcctgc caacccacgc ccggccaggt   3180
ccccaccttc cggtgctcgg ccacgctccg gggctggtct ggggtccggc tggcgccggc   3240
cgccgctccc gcccgcggcg aggccctcgg cttccccggg atgtccgcag gcatggtgcg   3300
ccccttcgcc acccccagcc gagggcaggc tgggcgcgcg gtttcccagg cacttctccc   3360
gcgggtccca ggctcagcta ccaagcgcgt gtctgcagca gcccggctat ttaaggcagc   3420
gcggctgcgg ggcgtgggaa tccctctccg cgttctttcc cacactcgag ccagccaatg   3480
agccgccggc gccgggcagc ccgcccccgg ccgctgcccc cgccggctgt cagtcacgag   3540
tcagctcccg gcccacagac cccgctggca acaaaggcta gccggggcac cccgcccgcg   3600
cctgcctcgg accacgccgg ccaggcggga aaatcgccgc gccccggtcc ccagttccga   3660
gcgatgcgcc gggagggggc ctctccggga gggcggaggc gcgaggctca ccttcaggcc   3720
```

-continued

```
gagcggagac cgcgagaagt ctgaaaggaa aattcgcgag gggcccttat gcgctcacga   3780

agaaccggcg agcctccgcc ttccgcggat cccgcggggg ccttggacct ccgcgcagcc   3840

tgcgcatctg accctcgccg ccagcagcac ctgcacgatg ccggggacac agtgaacatg   3900

gaacaccagc cgctggacag gagagaagct gactggccaa ggtcgtgagg gaagcagggt   3960

ggcatcacag ggccaaagaa agtaatgccg cagagcagat agtgacgtca tcacaggcag   4020

gatgttgtca tggtatggaa tgtaaggatg ttactggtca ggctggtgat gtctccaagc   4080

aatcataggt gatatctcag ggttaaggta gatgatgaca caagccagat gtaatgatgt   4140

atggtcactg gtgatgtcac tctcttctgg attacccaaa agtgatgagc caagcagcag   4200

ccaagaaagt agaactcaca aaaaatgaag gataattgtt acatttctgt ttgttatttc   4260

aaagaagcac gtggaggaaa gagggctaag cttattttcg tgtttgatgt tgttttcact   4320

ttgaattccc ttgtggggca caatcatgtt ttgagttttg gggatgccag cccatggtgg   4380

cctgggcagt cttgtctgca tcccacaaac ctctctggag gctcactgta ggcctgactg   4440

ttcttggggc tggggaggcc tctcctgaac tctgaactga tgtgggagga aaaggcaaat   4500

gagcaaaata aataatgaca tggtttccag agacagaaag aaatgtgtag gttttggggg   4560

gagccgaaag ccttctttcc actgagtggt ctggatggta tttttgcagt gagctctgct   4620

ggagaaggca atggca                                                   4636
```

<210> SEQ ID NO 18
<211> LENGTH: 429
<212> TYPE: DNA
<213> ORGANISM: Bos taurus

<400> SEQUENCE: 18

```
aagcagcagc caagaaagta gaactcacaa aaaatgaagg ataattgtta catttctgtt     60

tgttatttca aagaagcacg tggaggaaag agggctaagc ttattttcgt gtttgatgtt    120

gttttcactt tgaattccct tgtggggcac aatcatgttt tgagttttgg ggatgccagc    180

ccatggtggc ctgggcagtc ttgtctgcat cccacaaacc tctctggagg ctcactgtag    240

gcctgactgt tcttggggct ggggaggcct ctcctgaact ctgaactgat gtgggaggaa    300

aaggcaaatg agcaaaataa ataatgacat ggtttccaga gacagaaaga aatgtgtagg    360

ttttgggggg agccgaaagc cttctttcca ctgagtggtc tggatggtat ttttgcagtg    420

agctctgct                                                            429
```

<210> SEQ ID NO 19
<211> LENGTH: 364
<212> TYPE: DNA
<213> ORGANISM: Bos taurus

<400> SEQUENCE: 19

```
ccccactcca gtactcttgc ctggaaaatc ccatggacgg aggagcctgg tgggctacag     60

tccatggggt cgctaagagt cggacacgac tgagcgactt cactttcact tttcactttc    120

atgcattgga gaaggaaatg gcaacccact ccagtgttct tgcctgcaga atcccaggga    180

cgggggagcc tggtgggctg ccgtctctgg ggtcgcacag agttggacac gactgaagcg    240

acttagcagc agtagcagca gcagcaggtg ctatttttct taaccatttt ctggcctcag    300

ttaggatcct gtgtctttcc tcagtgctga aaagggagac tagtagttgg attatgtcat    360

ccta                                                                 364
```